United States Patent
Rozwadowski et al.

(10) Patent No.: US 9,309,525 B2
(45) Date of Patent: *Apr. 12, 2016

(54) MODULATION OF MEIOTIC RECOMBINATION

(71) Applicant: HER MAJESTY THE QUEEN IN RIGHT OF CANADA, AS REPRESENTED BY THE MINISTER OF AGRICULTURE AND AGRI-FOOD, Saskatoon, Saskatchewan (CA)

(72) Inventors: Kevin L. Rozwadowski, Saskatoon (CA); Derek J. Lydiate, Saskatoon (CA)

(73) Assignee: Her Majesty the Queen in Right of Canada, as Represented by the Minister of Agriculture and Agri-Food, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,907

(22) Filed: Mar. 17, 2014

(65) Prior Publication Data

US 2014/0193917 A1 Jul. 10, 2014

Related U.S. Application Data

(63) Continuation of application No. 10/380,687, filed as application No. PCT/CA01/01306 on Sep. 12, 2001, now Pat. No. 8,716,022.

(60) Provisional application No. 60/256,490, filed on Dec. 20, 2000, provisional application No. 60/249,296, filed on Nov. 17, 2000.

(30) Foreign Application Priority Data

Sep. 15, 2000 (CA) ..................................... 2319247

(51) Int. Cl.
| | |
|---|---|
| C12N 15/63 | (2006.01) |
| C12N 15/81 | (2006.01) |
| C12N 15/82 | (2006.01) |
| C12N 15/52 | (2006.01) |
| C12N 15/873 | (2010.01) |
| C12N 15/90 | (2006.01) |

(52) U.S. Cl.
CPC ............ *C12N 15/81* (2013.01); *C12N 15/8213* (2013.01); *C12N 15/873* (2013.01); *C12N 15/905* (2013.01); *C12N 15/907* (2013.01)

(58) Field of Classification Search
CPC ........... C12N 15/8201; C12N 15/8241; C12N 15/81; C07K 14/415; C07K 14/395
See application file for complete search history.

(56) References Cited

U.S. PATENT DOCUMENTS

| | | | |
|---|---|---|---|
| 4,684,611 A | 8/1987 | Schilperoort et al. | |
| 4,743,548 A | 5/1988 | Crossway et al. | |
| 4,801,540 A | 1/1989 | Hiatt et al. | |
| 4,940,838 A | 7/1990 | Schilperoort et al. | |
| 4,945,050 A | 7/1990 | Sanford et al. | |
| 5,015,580 A | 5/1991 | Christou et al. | |
| 5,149,655 A | 9/1992 | McCabe et al. | |
| 5,231,019 A | 7/1993 | Paszkowski et al. | |
| 5,464,763 A | 11/1995 | Schilperoort et al. | |
| 5,466,587 A | 11/1995 | Fitzpatrick-McElligott et al. | |
| 5,599,701 A | 2/1997 | Henry et al. | |
| 5,780,296 A | 7/1998 | Holloman et al. | |
| 5,945,339 A | 8/1999 | Holloman et al. | |
| 6,734,019 B1 * | 5/2004 | Doutriaux et al. ............ | 435/419 |
| 7,947,874 B2 | 5/2011 | Rozwadowski et al. | |

FOREIGN PATENT DOCUMENTS

| | | |
|---|---|---|
| EP | 0 506 289 A1 | 9/1992 |
| WO | WO 97/08331 A1 | 3/1997 |
| WO | WO 99/19492 A2 | 4/1999 |
| WO | WO 00/31268 A1 | 6/2000 |
| WO | WO 00/36109 A1 | 6/2000 |
| WO | WO 02/08432 A2 | 1/2002 |

OTHER PUBLICATIONS

Marsh et al RAD51 Is Required for Propagation of the Germinal Nucleus in Tetrahymena thermophila, Genetics 154: 1587-1596 (Apr. 2000).*
Adams, A. et al. (1997) "Methods in Yeast Genetics" *Cold Spring Harbor Laboratory Press*, pp. 19-157.
Ainley, W.M. et al., "Development of a heat shock inducible expression cassette for plants: characterization of parameters for its use in transient expression assays", Plant Mol. Biol. 14: 949-967 (1990).
Ajimura, M. et al., "Identification of new genes required for meiotic recombination in *Saccharomyces cerevisiae*", Genetics 133: 51-66 (1993).
Alani, E. et al., "The yeast RAD50 gene encodes a predicted 153-kD protein containing a purine nucleotide-binding domain and two large heptad-repeat regions", Genetics 122: 47-57 (1989).
Alani, E. et al., "Characterization of DNA-binding and strand-exchange stimulation properties of y-RPA, a yeast single-strand-DNA-binding protein", J. Mol. Biol. 227: 54-71 (1992).
Altschul, S.F. et al., "Basic local alignment search tool", J. Mol. Biol. 215: 403-410 (1990).

(Continued)

*Primary Examiner* — Maria Marvich
(74) *Attorney, Agent, or Firm* — Knobbe, Martens, Olson & Bear, LLP

(57) ABSTRACT

The invention provides methods of modifying the level of expression or functional activity of factors such as enzymes or other catalytic proteins or structural proteins, alone or in concert, to modify the frequency of meiotic homologous recombination involving the exchange of genetic information between non-sister chromatids from homologous maternal and paternal chromosomes. The steps at which modulation may occur include: homologous chromosome pairing, double-strand break formation; resection; strand invasion; branch migration; and resolution. Methods of plant and animal breeding are also provided that utilize the modulation of meiotic homologous recombination.

15 Claims, No Drawings

(56) References Cited

OTHER PUBLICATIONS

Arbel, A. et al., "Sister chromatid-based DNA repair is mediated by RAD54, not by DMC1 or TID1", EMBO J. 18: 2648-2658 (1999).
Arnaudeau, C. et al., "The RAD51 protein supports homologous recombination by an exchange mechanism in mammalian cells", J. Mol. Biol. 289: 1231-1238 (1999).
Asleson, E.N. et al., "A core activity associated with the N terminus of the yeast RAD52 protein is revealed by RAD51 overexpression suppression of C-terminal rad52 truncation alleles", Genetics 153: 681-692 (1999).
Atcheson, C.L. et al. 1987 "Isolation, DNA sequence, and regulation of a meiosis-specific eukaryotic recombination gene" *Proc Natl Acad Sci USA* 84: 8035-8039.
Ausubel, et al. (eds.) (1993) "Hybridization Analysis of DNA Blots" *Current Protocols n Molecular Biology* vol. 1, Green Publishing Associates, Inc., and John Wiley & Sons, Inc., New York, pp. 2.10.1-2.10.6.
Bai, Y. et al., "A Rad52 homolog is required for RAD51-independent mitotic recombination in *Saccharomyces cerevisiae*", Genes Dev. 10: 2025-2037 (1996).
Basile, G. et al., "Nucleotide sequence and transcriptional regulation of the yeast recombinational repair gene RAD51", Mol. Cell Biol. 12: 3235-3246 (1992).
Bass, H.W. et al., "Telomeres cluster de novo before the initiation of synapsis: a three-dimensional spatial analysis of telomere positions before and during meiotic prophase", J. Cell Biol. 137: 5-18 (1997).
Baumann, P. et al. (1997) "Purification of Human Rad51 Protein by Selective Spermidine Precipitation" *Mutat. Res.* 384:65-72.
Baumann, P. et al., "Heteroduplex formation by human Rad51 protein: effects of DNA end-structure, hRP-A and hRad52", J. Mol. Biol. 291: 363-374 (1999).
Benson, F.E. et al., "Synergistic actions of Rad51 and Rad52 in recombination and DNA repair", Nature 391: 401-404 (1998).
Benton, B.M. et al., "Signal-mediated import of bacteriophage T7 RNA polymerase into the *Saccharomyces cerevisiae* nucleus and specific transcription of target genes", Mol. Cell Biol. 10: 353-360 (1990).
Bergerat, A. et al., "An atypical topoisomerase II from Archaea with implications for meiotic recombination", Nature 386: 414-417 (1997).
Bishop, D.K. et al., "DMC1: a meiosis-specific yeast homolog of *E. coli* recA required for recombination, synaptonemal complex formation, and cell cycle progression", Cell 69: 439-456 (1992).
Bishop, D.K. "RecA homologs Dmc1 and Rad51 interact to form multiple nuclear complexes prior to meiotic chromosome synapsis", Cell 79: 1081-1092 (1994).
Biswas, E.E. et al., "Stimulation of RTH1 nuclease of the yeast *Saccharomyces cerevisiae* by replication protein A", Biochemistry 36: 5955-5962 (1997).
Bohner, S. et al., "Technical advance: transcriptional activator TGV mediates dexamethasone-inducible and tetracycline-inactivatable gene expression", Plant J. 19: 87-95 (1999).
Bressan, D.A. et al., "Alteration of N-terminal phosphoesterase signature motifs inactivates *Saccharomyces cerevisiae* Mre11", Genetics 150: 591-600 (1998).
Broverman, S. et al., "Alteration of Caenorhabditis elegans gene expression by targeted transformation", Proc. Natl. Acad. Sci. U.S.A 90: 4359-4363 (1993).
Carney, J.P. et al., "The hMre11/hRad50 protein complex and Nijmegen breakage syndrome: linkage of double-strand break repair to the cellular DNA damage response", Cell 93: 477-486 (1998).
Cha, R.S. et al., "Progression of meiotic DNA replication is modulated by interchromosomal interaction proteins, negatively by Spo11p and positively by Rec8p", Genes Dev. 14: 493-503 (2000).
Chamankhah, M. et al., "Isolation of hMRE11B: failure to complement yeast mre11 defects due to species-specific protein interactions", Gene 225: 107-116 (1998).
Chanet, R. et al., "Semidominant mutations in the yeast Rad51 protein and their relationships with the Srs2 helicase", Mol. Cell Biol. 16: 4782-4789 (1996).

Chedin, F. et al., "Novel homologs of replication protein A in archaea: implications for the evolution of ssDNA-binding proteins", Trends Biochem. Sci. 23: 273-277 (1998).
Chen, Q. et al., "Isolation and characterization of a cDNA encoding a synaptonemal complex protein", Biochem Cell Biol. 70: 1030-1038 (1992).
Chu, S. et al., "The transcriptional program of sporulation in budding yeast", Science 282: 699-705 (1998).
Church, G.M. et al., "Genomic sequencing", Proc. Natl. Acad. Sci. U.S.A 81: 1991-1995 (1984).151.
Ohta K, Shibata T, Nicolas A.: Changes in chromatin structure at recombination initiation sites during yeast meiosis. EMBO J. 13:5754-63 (1994).
Citovsky, V. et al., "The P30 movement protein of tobacco mosaic virus is a single-strand nucleic acid binding protein", Cell 60: 637-647 (1990).
Citovsky, V. et al., "Cooperative interaction of Agrobacterium VirE2 protein with single-stranded DNA: implications for the T-DNA transfer process", Proc. Natl. Acad. Sci. U.S.A 86: 1193-1197 (1989).
Clever, B. et al., "Recombinational repair in yeast: functional interactions between Rad51 and Rad54 proteins", EMBO J. 16: 2535-2544 (1997).
Couteau, F. et al., "Random chromosome segregation without meiotic arrest in both male and female meiocytes of a dmc1 mutant of Arabidopsis", Plant Cell 11: 1623-1634 (1999).
Cress, W.D., et al., "Histone deacetylases, transcriptional control, and cancer", J. Cell Physiol. 184:1-16 (2000).
Critchlow, S.E. et al., "DNA end joining: from yeast to man", Trends Biochem. Sci. 23: 394-398 (1998).
Cupples, C.G. et al., "A set of lacZ mutations in *Escherichia coli* that allow rapid detection of each of the six base substitutions", Proc. Natl. Acad. Sci. U.S.A 86: 5345-5349 (1989).
Dean, R.B. et al., "Simplified statistics for small numbers of observations", Anal. Chem. 23: 636-638 (1951).
Devore, J.L. "Probability and Statistics" *Duxbury Press*, pp. 89-196, 420-473, 622-657.
Dolganov, G.M. et al., "Human Rad50 is physically associated with human Mre11: identification of a conserved multiprotein complex implicated in recombinational DNA repair", Mol. Cell Biol. 16: 4832-4841 (1996).
Dosanjh, M.K et al., "Isolation and characterization of RAD51C, a new human member of the RAD51 family of related genes", Nucleic Acids Res. 26: 1179-1184 (1998).
Doutriaux, M.P. et al., "Isolation and characterisation of the RAD51 and DMC1 homologs from Arabidopsis thaliana", Mol. Gen. Genet. 257: 283-291 (1998).
Dresser, M.E. et al., "DMC1 functions in a *Saccharomyces cerevisiae* meiotic pathway that is largely independent of the RAD51 pathway", Genetics 147: 533-544 (1997).
Emery, H.S. et al., "Sequence of RAD54, a *Saccharomyces cerevisiae* gene involved in recombination and repair", Gene 104: 103-106 (1991).
Evans, D.A. et al. (1983) "Protoplasts Isolation and Culture" Handbook of Plant Cell Culture, Macmillian Publishing Company, New York, pp. 124-176.
Fraley et al., Proc. Nat'l Acad. Sci. USA 80:4803 (1983), Expression of bacterial genes in plant cells.
Fromm et al., Proc. Natl. Acad. Sci. USA 82:5824 (1985), Expression of genes transferred into monocot and dicot plant cells by electroporation.
Furuse, M. et al., "Distinct roles of two separable in vitro activities of yeast Mre11 in mitotic and meiotic recombination", EMBO J. 17: 6412-6425 (1998).
Gari, E. et al., "A set of vectors with a tetracycline-regulatable promoter system for modulated gene expression in *Saccharomyces cerevisiae*", Yeast 13: 837-848 (1997).
Gasior, S.L. et al "Rad52 associates with RPA and functions with rad55 and rad57 to assemble meiotic recombination complexes", Genes Dev. 12: 2208-2221 (1998).
Gatz, C. et al., "Regulation of a modified CaMV 35S promoter by the Tn10-encoded Tet repressor in transgenic tobacco", Mol. Gen. Genet. 227: 229-237 (1991).

(56) References Cited

OTHER PUBLICATIONS

Gietz, R.D. et al., "Studies on the transformation of intact yeast cells by the LiAc/SS-DNA/PEG procedure", Yeast 11: 355-360 (1995).
Guo et al. 2004 "Protein tolerance to random amino acid change" *Proc Natl Acad Sci USA* 101: 9205-9201.
Golub, E.I. et al., "Interaction of human rad51 recombination protein with single-stranded DNA binding protein, RPA", Nucleic Acids Res. 26: 5388-5393 (1998).
Gordon-Kamm, et al., The Plant Cell 2:603 (1990).
Gupta, R.C. et al.,"Activities of human recombination protein Rad51", Proc. Natl. Acad. Sci. U.S.A 94: 463-468 (1997).
Gutierrez, C, et al., "Mechanism of stimulation of DNA replication by bacteriophage phi 29 single-stranded DNA-binding protein p5", J. Biol. Chem. 266: 2104-2111 (1991).
Guyer, D. et al., "Activation of latent transgenes in Arabidopsis using a hybrid transcription factor", Genetics 149: 633-639 (1998).
Haber, J.E., "DNA recombination: the replication connection", Trends Biochem. Sci. 24: 271-275 (1999).
Habu, T., et al., "The mouse and human homologs of DMC1, the yeast meiosis-specific homologous recombination gene, have a common unique form of exon-skipped transcript in meiosis", Nucleic Acids Res. 24: 470-477 (1996).
Hall, R.M. et al., "Mobile gene cassettes and integrons: capture and spread of genes by site-specific recombination", Mol. Microbiol. 15: 593-600 (1995).
Hartung, F. et al., "Isolation of the complete cDNA of the Mre11 homologue of Arabidopsis indicates conservation of DNA recombination mechanisms between plants and other eukaryotes", Plant Physiol. 121: 312 (1999).
Hartung, F. et al., "Molecular characterisation of two paralogous SPO11 homologues in Arabidopsis thaliana", Nucleic Acids Res. 28: 1548-1554 (2000).
Havre, P.A. et al., "The human REC2/RAD51B gene acts as a DNA damage sensor by inducing G1 delay and hypersensitivity to ultraviolet irradiation", Cancer Res. 58: 4733-4739 (1998).
Hebsgaard, S.M. et al.,"Splice site prediction in Arabidopsis thaliana pre-mRNA by combining local and global sequence information", Nucleic Acids Res. 24: 3439-3452 (1996).
Henikoff and Henikoff, 1992, Proc. Natl. Acad. Sci. USA 89: 10915-10919.
Hollingsworth, N.M. et al., "The HOP1 gene encodes a meiosis-specific component of yeast chromosomes", Cell 61: 73-84 (1990).
Hollingsworth, N.M. et al., "MSH5, a novel MutS homolog, facilitates meiotic reciprocal recombination between homologs in *Saccharomyces cerevisiae* but not mismatch repair", Genes Dev. 9: 1728-1739 (1995).
Horsch et al. Science 233: 496 (1984).
Hunter, N. et al., "Mlh1 is unique among mismatch repair proteins in its ability to promote crossing-over during meiosis", Genes Dev. 11: 1573-1582 (1997).
Hyde, H. et al., "Resolution of recombination intermediates by a mammalian activity functionally analogous to *Escherichia coli* RuvC resolvase", J. Biol. Chem. 269: 5202-5209 (1994).
Ivanov, E.L. et al., "Mutations in XRS2 and RAD50 delay but do not prevent mating-type switching in *Saccharomyces cerevisiae*", Mol. Cell Biol. 14: 3414-3425 (1994).
Jean, M. et al., "Isolation and characterization of AtMLH1, a MutL homologue from Arabidopsis thaliana", Mol. Gen. Genet. 262: 633-642 (1999).
Jiang, H. et al., "Direct association between the yeast Rad51 and Rad54 recombination proteins", J. Biol. Chem. 271: 33181-33186 (1996).
Johnson, R.D. et al., "Functional differences and interactions among the putative RecA homologs Rad51, Rad55, and Rad57", Mol. Cell Biol. 15: 4843-4850 (1995).
Johzuka, K. et al., "Interaction of Mre11 and Rad50: two proteins required for DNA repair and meiosis-specific double-strand break formation in *Saccharomyces cerevisiae*", Genetics 139: 1521-1532 (1995).
Junghans, H. et al., "A simple and rapid method for the preparation of total plant DNA", Biotechniques 8: 176 (1990).
Kalderon, D. et al., "A short amino acid sequence able to specify nuclear location", Cell 39: 499-509 (1984).
Kanaar, R. et al.,"Human and mouse homologs of the *Saccharomyces cerevisiae* RAD54 DNA repair gene: evidence for functional conservation", Curr. Biol. 6: 828-838 (1996).
Kans, J.A. et al., "Nucleotide sequence of the RAD57 gene of *Saccharomyces cerevisiae*", Gene 105: 139-140 (1991).
Keeney, S. et al., "Meiosis-specific DNA double-strand breaks are catalysed by Spo11, a member of a widely conserved protein family", Cell 88: 375-384 (1997).
Kleckner, N., "Meiosis: how could it work?", Proc. Natl. Acad. Sci. U.S.A 93: 8167-8174 (1996).
Klee et al., Ann. Rev. of Plant Phys. 38:467 (1987), Agrobacterium-mediated plant transformation and its further application to plant biology.
Kleff, S. et al., "Identification and characterization of yeast mutants and the gene for a cruciform cutting endonuclease". EMBO J. 11: 699-704 (1992), High velocity microprojectiles for delivering nucleic acids into living cells.
Klein, et al., Nature 327: 70 (1987).
Klimyuk,V.I. et al., "AtDMC1, the Arabidopsis homologue of the yeast DMC1 gene: characterization, transposon-induced allelic variation and meiosis-associated expression", Plant J. 11: 1-14 (1997).
Kobayashi, T. et al., "Characterization of cDNAs induced in meiotic prophase in lily microsporocytes", DNA Res. 1: 15-26 (1994).
Kolodner, R.D. et al., "Structure of the human MLH1 locus and analysis of a large hereditary nonpolyposis colorectal carcinoma kindred for mlh1 mutations", Cancer Res. 55: 242-248 (1995).
Kowalczykowski, S.C. et al., "Biochemistry of homologous recombination in *Escherichia coli*.", Microbiol. Rev. 58: 401-465 (1994).
Kumar, L.S., "DNA markers in plant improvement: An overview", Biotechnol. Adv. 17: 143-182 (1999).
Kupfer, C., et al., "Reactions of mitochondrial cruciform cutting endonuclease 1 (CCE1) of yeast *Saccharomyces cerevisiae* with branched DNAs in vitro", Eur. J. Biochem. 238: 77-87 (1996).
Labow, M.A. et al., "Conversion of the lac repressor into an allosterically regulated transcriptional activator for mammalian cells", Mol. Cell Biol. 10: 3343-3356 (1990).
Lesk et al. 2007 "Prediction of protein function from protein sequence and structure" pp. 27 and 28, downloaded on Sep. 16, 2007.
Li, Z. et al., "Recombination activities of HsDmc1 protein, the meiotic human homolog of RecA protein", Proc. Natl. Acad. Sci. U.S.A 94: 11221-11226 (1997).
Lindahl, T. et al., "Quality control by DNA repair", Science 286: 1897-1905 (1999).
Link, A.J. et al., "Physical map of the *Saccharomyces cerevisiae* genome at 110-kilobase resolution", Genetics 127: 681-698 (1991).
Lovett, S.T., "Sequence of the RAD55 gene of *Saccharomyces cerevisiae*: similarity of RAD55 to prokaryotic RecA and other RecA-like proteins", Gene 142: 103-106 (1994).
Martinez, A., et al., "Ecdysone agonist inducible transcription in transgenic tobacco plants", Plant J. 19: 97-106 (1999).
Mazin, A.V. et al., "Tailed duplex DNA is the preferred substrate for Rad51 protein-mediated homologous pairing", EMBO J. 19: 1148-1156 (2000).
Mett, V.L. et al., "Copper-controllable gene expression system for whole plants", Proc. Natl. Acad. Sci. U.S.A. 90: 4567-4571 (1993).
Mett, V.L. et al., "A system for tissue-specific copper-controllable gene expression in transgenic plants: nodule-specific antisense of aspartate aminotransferase-P2", Transgenic Res. 5: 105-113 (1996).
Meyer, R.R. et al., "The single-stranded DNA-binding protein of *Escherichia coli*", Microbiol. Rev. 54: 342-380 (1990).
Miao, Z.H. et al., "Targeted disruption of the TGA3 locus in Arabidopsis thaliana", Plant J. 7: 359-365 (1995).
Milne, G.T. et al., "Dominant negative alleles of RAD52 reveal a DNA repair/recombination complex including Rad51 and Rad52", Genes Dev. 7: 1755-1765 (1993).
Monaghan, A. et al., "Adenovirus DNA binding protein: helix destabilising properties", Nucleic Acids Res. 22: 742-748 (1994).

(56) References Cited

OTHER PUBLICATIONS

Moore, S.P. et al. 1991 "The human homologous pairing protein HPP-1 is specifically stimulated by the cognate single-stranded binding protein hRP-A" Proc Natl Acad Sci USA 88:9067-9071.
Moore, I. et al., "A transcription activation system for regulated gene expression in transgenic plants", Proc. Natl. Acad. Sci. U.S.A 95: 376-381 (1998).
Muris, D.F. et al., "Cloning of human and mouse genes homologous to RAD52, a yeast gene involved in DNA repair and recombination", Mutat. Res. 315: 295-305 (1994).
Needleman and Wunsch, 1970, J. Mol. Biol. 48:443, A general method applicable to the search for similarities in the amino acid sequence of two proteins.
Offringa, R, et al., "Extrachromosomal homologous recombination and gene targeting in plant cells after Agrobacterium mediated transformation", EMBO J. 9: 3077-3084 (1990).
Ogawa, T. et al., "Similarity of the yeast RAD51 filament to the bacterial RecA filament", Science 259: 1896-1899 (1993).
Ohta, K. et al., "Changes in chromatin structure at recombination initiation sites during yeast meiosis", EMBO J. 13:5754-63 (1994).
Paques, F. et al., "Multiple pathways of recombination induced by double-strand breaks in *Saccharomyces cerevisiae*", Microbiol. Mol. Biol. Rev. 63: 349-404 (1999).
Paquis-Flucklinger, V. et al., "Cloning and expression analysis of a meiosis-specific MutS homolog: the human MSH4 gene", Genomics 44: 188-194 (1997).
Passy, S.I. et al., "Human Dmc1 protein binds DNA as an octameric ring", Proc. Natl. Acad. Sci. U.S.A 96: 10684-10688 (1999).
Paszkowski et al., EMBO J. 3:2717 (1984), Direct gene transfer to plants.
Paterson, A.H. et al., "DNA markers in plant improvement", Advances in Agronomy 46: 39-90 (1997).
Pearson and Lipman, 1988, Proc. Natl. Acad. Sci. USA 85: 2444, Improved tools for biological sequence comparison.
Peterson, C.L., "ATP-dependent chromatin remodeling: going mobile", FEBS Lett. 476:68-72 (2000).
Peterson, C.L. et al., "Recruitment of chromatin remodeling machines", J. Cell Biochem. 78:179-85 (2000).
Petrini, J.H. et al., "Isolation and characterization of the human MRE11 homologue", Genomics 29: 80-86 (1995).
Petukhova, G. et al., "Catalysis of homologous DNA pairing by yeast Rad51 and Rad54 proteins", Nature 393: 91-94 (1998).
Philipova, D. et al., "A hierarchy of SSB protomers in replication protein A", Genes Dev. 10: 2222-2233 (1996).
Pittman, D.L. et al., "Meiotic prophase arrest with failure of chromosome synapsis in mice deficient for Dmc1, a germline-specific RecA homolog", Mol. Cell 1: 697-705 (1998).
Reiss, B. et al., "RecA protein stimulates homologous recombination in plants", Proc. Natl. Acad. Sci. U.S.A 93: 3094-3098 (1996).
Reiss, B. et al., "RecA stimulates sister chromatid exchange and the fidelity of double-strand break repair, but not gene targeting, in plants transformed by Agrobacterium", Proc. Natl. Acad. Sci. U.S.A 97: 3358-3363 (2000).
Rockmill, B. et al., "A meiosis-specific protein kinase homolog required for chromosome synapsis and recombination", Genes Dev. 5: 2392-2404 (1991).
Rockmill, B. et al., "RED1: a yeast gene required for the segregation of chromosomes during the reductional division of meiosis", Proc. Natl. Acad. Sci. U.S.A. 85: 6057-6061 (1988).
Rockmill, B. et al., "Roles for two RecA homologs in promoting meiotic chromosome synapsis", Genes Dev. 9: 2684-2695 (1995).
Roeder, G.S., "Chromosome synapsis and genetic recombination: their roles in meiotic chromosome segregation", Trends Genet. 6: 385-389 (1990).
Roeder, G.S., "Meiotic chromosomes: it takes two to tango", Genes Dev. 11: 2600-2621 (1997).
Roeder,G.S., "Sex and the single cell: meiosis in yeast", Proc. Natl. Acad. Sci. U.S.A. 92: 10450-10456 (1995).

Rogers, S. et al. (1986) "Gene Transfer in Plants: Production of Transformed Plants Using Ti Plasmid Vectors" *Methods, Enzymol.* 118:627-640.
Rong,Y. S. et al.,"Gene targeting by homologous recombination in drosophila", Science 288: 2013-2018 (2000).
Ross-Macdonald, P. et al., "Mutation of a meiosis-specific MutS homolog decreases crossing over but not mismatch correction", Cell 79: 1069-1080 (1994).
Rothstein, R., "Targeting, disruption, replacement, and allele rescue: integrative DNA transformation in yeast", Methods Enzymol. 194: 281-301 (1991).
Rozwadowsky, K. et al. "AtMRE11: a component of meiotic recombination and DNA repair in plants," 10$^{th}$ International Conference on Arabidopsis Research, Melbourne, Australia, Jul. 4-8, 1999, Abstract.
Rubin, B.P., et al., "Structure of REC2, a recombinational repair gene of Ustilago maydis, and its function in homologous recombination between plasmid and chromosomal sequences", Mol. Cell Biol. 14: 6287-6296 (1994).
Scherthan, H. et al., "Centromere and telomere movements during early meiotic prophase of mouse and man are associated with the onset of chromosome pairing", J. Cell Biol. 134: 1109-1125 (1996).
Schild, D., "Suppression of a new allele of the yeast RAD52 gene by overexpression of RAD51, mutations in srs2 and ccr4, or mating-type heterozygosity", Genetics 140: 115-127 (1995).
Schmekel, K. et al.,"Organization of SCP1 protein molecules within synaptonemal complexes of the rat", Exp Cell Res 226: 20-30 (1996).
Schneider, J.C. et al., "Vectors for expression of cloned genes in yeast: regulation, overproduction, and underproduction", Methods Enzymol. 194: 373-388 (1991).
Shalev, G. et al., "Stimulation of homologous recombination in plants by expression of the bacterial resolvase ruvC", Proc. Natl. Acad. Sci.U.S.A 96: 7398-7402 (1999).
Shao, R.G. et al., "Replication-mediated DNA damage by camptothecin induces phosphorylation of RPA by DNA-dependent protein kinase and dissociates RPA:DNA-PK complexes", EMBO J. 18: 1397-1406 (1999).
Shcherbakova, O.G. et al., "Overexpression of bacterial RecA protein stimulates homologous recombination in somatic mammalian cells", Mutat. Res. 459: 65-71 (2000).
Shinohara, A. et al., "Cloning of human, mouse and fission yeast recombination genes homologous to RAD51 and recA", Nat. Genet. 4: 239-243 (1993).
Shinohara, A. et al., "Rad51 protein involved in repair and recombination in *S. cerevisiae* is a RecA-like protein", Cell 69: 457-470 (1992).
Smith and Waterman, 1981, Adv. Appl. Math 2: 482, Comparison of Biosequences.
Smith et al. 1998 "Recombination at work for meiosis" *Curr Opin Genet Develop* 8: 200-211.
Sonoda, E. et al.,"Rad51-deficient vertebrate cells accumulate chromosomal breaks prior to cell death", EMBO J. 17: 598-608 (1998).
Sterner, D.E. et al., "Acetylation of histones and transcription-related factors", Microbiol. Mol. Biol. Rev. 64:435-59 (2000).
Story, R.M. et al., "Structure of the recA protein-ADP complex", Nature 355: 374-376 (1992).
Story, R.M. et al., "The structure of the *E. coli* recA protein monomer and polymer", Nature 355: 318-325 (1992).
Sugawara, N. et al., "DNA structure-dependent requirements for yeast RAD genes in gene conversion", Nature 373: 84-86 (1995).
Sugiyama, T. et al., "A single-stranded DNA-binding protein is needed for efficient presynaptic complex formation by the *Saccharomyces cerevisiae* Rad51 protein", J. Biol. Chem. 272: 7940-7945 (1997).
Sung, P. et al., "DNA strand exchange mediated by a RAD51-ssDNA nucleoprotein filament with polarity opposite to that of RecA", Cell 82: 453-461 (1995).
Sung, P. et al., "Yeast Rad51 recombinase mediates polar DNA strand exchange in the absence of ATP hydrolysis", J. Biol. Chem. 271: 27983-27986 (1996).
Sym, M. et al., "Zip1-induced changes in synaptonemal complex structure and polycomplex assembly", J. Cell Biol. 128: 455-466 (1995).

(56) References Cited

OTHER PUBLICATIONS

Takanami, T. et al., "Characterization of a Caenorhabditis elegans recA-like gene Ce-rdh-1 involved in meiotic recombination", DNA Res. 5: 373-377 (1998).
Thompson, D. et al., "Genetic Control of Recombination Partner Preference in Yeast Meiosis: Isolation and Characterization of Mutants Elevated for Meiotic Unequal Sister-Chromatid Recombination", Genetics 153: 621-641, Oct. 1999.
Thompson, S. et al., "Germ line transmission and expression of a corrected HPRT gene produced by gene targeting in embryonic stem cells", Cell 56: 313-321 (1989).
Tijssen, (1993) "Overview of Principles of Hybridization and the strategy of Nucleic Acid Probe Assays" *Laboratory Techniques in Biochemistry and Molecular Biology—Hybridization with Nucleic Acid Probes* Part 1, Chapter 2 Elsevier, New York, pp. 19-78.
Tishkoff, D.X. et al., "Molecular and genetic analysis of the gene encoding the *Saccharomyces cerevisiae* strand exchange protein Sep1", Mol. Cell Biol. 11: 2593-2608 (1991).
Trelles-Sticken, E. et al., "Bouquet formation in budding yeast: initiation of recombination is not required for meiotic telomere clustering", J. Cell Sci. 112 ( Pt 5): 651-658 (1999).
Tsubouchi, H. et al., "A novel mre11 mutation impairs processing of double-strand breaks of DNA during both mitosis and meiosis", Mol. Cell Biol. 18: 260-268 (1998).
Tsuzuki, T. et al., "Targeted disruption of the Rad51 gene leads to lethality in embryonic mice", Proc. Natl. Acad. Sci. U.S.A 93: 6236-6240 (1996).
Vispe, S. et al., "Overexpression of Rad51 protein stimulates homologous recombination and increases resistance of mammalian cells to ionizing radiation", Nucleic Acids Res. 26: 2859-2864 (1998).
Walker, J.E. et al., "Distantly related sequences in the alpha- and beta-subunits of ATP synthase, myosin, kinases and other ATP-requiring enzymes and a common nucleotide binding fold", EMBO J. 1: 945-951 (1982).
Weinmann, P. et al., "A chimeric transactivator allows tetracycline-responsive gene expression in whole plants", Plant J. 5: 559-569 (1994).
Williams, K.R. et al., "Primary structure of the bacteriophage T4 DNA helix-destabilizing protein", J. Biol. Chem. 256: 1754-1762 (1981).
Winand, N.J. et al., "Cloning and characterization of the human and Caenorhabditis elegans homologs of the *Saccharomyces cerevisiae* MSH5 gene", Genomics 53: 69-80 (1998).
Wold, M.S., "Replication protein A: a heterotrimeric, single-stranded DNA-binding protein required for eukaryotic DNA metabolism", Annu. Rev. Biochem. 66: 61-92 (1997).
Xu, Y. et al., "Targeted disruption of ATM leads to growth retardation, chromosomal fragmentation during meiosis, immune defects, and thymic lymphoma", Genes Dev. 10: 2411-2422 (1996).
Yanez, R.J. et al., "Gene targeting is enhanced in human cells overexpressing hRAD51", Gene Ther. 6: 1282-1290 (1999).
Yu, X. et al., "The RecA hexamer is a structural homologue of ring helicases", Nat. Struct. Biol. 4: 101-104 (1997).
Zaitseva, E.M. et al., "The DNA binding properties of *Saccharomyces cerevisiae* Rad51 protein", J. Biol. Chem. 274: 2907-2915 (1999).
Zhu, T. et al., "Engineering herbicide-resistant maize using chimeric RNA/DNA oligonucleotides", Nat. Biotechnol. 18: 555-558 (2000).

\* cited by examiner

SEQUENCE LISTING

```
<160> NUMBER OF SEQ ID NOS: 40

<210> SEQ ID NO 1
<211> LENGTH: 54
<212> TYPE: DNA
<213> ORGANISM: Artificial Sequence
<220> FEATURE:
<221> NAME/KEY: misc_binding
<222> LOCATION: (1)..(6)
<223> OTHER INFORMATION: BamHI restriction site
<220> FEATURE:
<221> NAME/KEY: misc_feature
<222> LOCATION: (13)..(15)
<223> OTHER INFORMATION: in-frame start codon
<220> FEATURE:
<221> NAME/KEY: misc_binding
<222> LOCATION: (49)..(54)
<223> OTHER INFORMATION: SmaI restriction site
<220> FEATURE:
<223> OTHER INFORMATION: Nuclear localization sequence (NLS)
      corresponding to that found in simian virus 40 T-antigen

<400> SEQUENCE: 1
ggatccaaaa aaatggctcc taagaagaag agaaaggttg gaggaggacc cggg          54

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide (OL11434) for amplifying and
      modifying target gene (AtDMC1)

<400> SEQUENCE: 2
catatgatgg cttctcttaa ggctg                                          25

<210> SEQ ID NO 3
<211> LENGTH: 22
<212> TYPE: DNA
<213> ORGANISM: Artificial Sequence
<220> FEATURE:
```

<223> OTHER INFORMATION: Oligonucleotide (OL11433) for amplifying and
      modifying target gene (AtDMC1)

<400> SEQUENCE: 3
gacatataaa agagttcgct cc                                              22

<210> SEQ ID NO 4
<211> LENGTH: 31
<212> TYPE: DNA
<213> ORGANISM: Artificial Sequence
<220> FEATURE:
<223> OTHER INFORMATION: Oligonucleotide (OL11435) for amplifying and
      modifying target gene (AtDMC1)

<400> SEQUENCE: 4
aaactcgagc taatccttcg cgtcagcaat g                                    31

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide (AtSPO-5'Sma) for amplifying
      and modifying target gene (AtSPO11)

<400> SEQUENCE: 5
gggtatggag ggaaaattcg ctag                                            24

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide (AtSPO-3'X) for amplifying and
      modifying target gene (AtSPO11)

<400> SEQUENCE: 6
ccttgagttg gagactagtt atc                                             23

<210> SEQ ID NO 7
<211> LENGTH: 41
<212> TYPE: DNA
<213> ORGANISM: Artificial Sequence
<220> FEATURE:
<223> OTHER INFORMATION: Oligonucleotide (AtSPO-3'PstNot) for amplifying
      and modifying target gene (AtSPO11)

<400> SEQUENCE: 7
atcctgcagg cggccgctca tcaaggagag cttacttcac g                         41

<210> SEQ ID NO 8
<211> LENGTH: 35
<212> TYPE: DNA
<213> ORGANISM: Artificial Sequence
<220> FEATURE:
<223> OTHER INFORMATION: Oligonucleotide (AtRAD51-5'Bam) for amplifying
      and modifying target gene (AtRAD51)

<400> SEQUENCE: 8
gggggatcca aaaaaatgac gacgatggag cagcg                                35

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide (AtRAD51-3'X) for amplifying and modifying target gene (AtRAD51)

<400> SEQUENCE: 9
gaagcaaggc attgttgtgg                                                    20

<210> SEQ ID NO 10
<211> LENGTH: 34
<212> TYPE: DNA
<213> ORGANISM: Artificial Sequence
<220> FEATURE:
<223> OTHER INFORMATION: Oligonucleotide (AtRAD51-3'Pst) for amplifying
      and modifying target gene (AtRAD51)

<400> SEQUENCE: 10
aactgcagtt atcaatcctt gcaatctgtt acac                                    34

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide (OL12414) for amplifying and
      modifying target gene (AtMRE11)

<400> SEQUENCE: 11
cggaattcat gattgtaaaa cttgacaggg                                         30

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide (OL12413) for amplifying and
      modifying target gene (AtMRE11)

<400> SEQUENCE: 12
ggtcgctgac tacttgaaac                                                    20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide (OL12415) for amplifying and
      modifying target gene (AtMRE11)

<400> SEQUENCE: 13
tcattcagac agtggcgacg                                                    20

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide (OL12779) for amplifying and
      modifying target gene (AtMRE11)

<400> SEQUENCE: 14
ggcctgaagt tcaagaag                                                      18

<210> SEQ ID NO 15
<211> LENGTH: 18
<212> TYPE: DNA
<213> ORGANISM: Artificial Sequence
<220> FEATURE:
<223> OTHER INFORMATION: Oligonucleotide (OL12780) for amplifying and
      modifying target gene (AtMRE11)

```
<400> SEQUENCE: 15
gctcgacttc ttcgcttg                                                     18

<210> SEQ ID NO 16
<211> LENGTH: 57
<212> TYPE: DNA
<213> ORGANISM: Artificial Sequence
<220> FEATURE:
<223> OTHER INFORMATION: Oligonucleotide (MRE-F1) for amplifying and
      modifying target gene (AtMRE11)

<400> SEQUENCE: 16
gcgctgcagc atatgcccgg ggaattcatg tctagggagg attttagtga tacactt         57

<210> SEQ ID NO 17
<211> LENGTH: 93
<212> TYPE: DNA
<213> ORGANISM: Artificial Sequence
<220> FEATURE:
<223> OTHER INFORMATION: Oligonucleotide (MRE-F2) for amplifying and
      modifying target gene (AtMRE11)

<400> SEQUENCE: 17
gcgctgcagc atatgcccgg ggaattcatg tctagggagg attttagtga tacacttcga     60
gtacttgttg caactgcttg ccacttgggc tac                                    93

<210> SEQ ID NO 18
<211> LENGTH: 46
<212> TYPE: DNA
<213> ORGANISM: Artificial Sequence
<220> FEATURE:
<223> OTHER INFORMATION: Oligonucleotide (MRE-R1) for amplifying and
      modifying target gene (AtMRE11)

<400> SEQUENCE: 18
cgcgtcgacc ccgggttaag gcgcgcctct tcttagagct ccatag                     46

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide (MRE-AVA) for amplifying and
      modifying target gene (AtMRE11)

<400> SEQUENCE: 19
gataggtcca ctcgacccac tgg                                               23

<210> SEQ ID NO 20
<211> LENGTH: 36
<212> TYPE: DNA
<213> ORGANISM: Artificial Sequence
<220> FEATURE:
<223> OTHER INFORMATION: Oligonucleotide (YDMC-5'Bam) for amplifying and
      modifying target gene (ScDMC1)

<400> SEQUENCE: 20
gggggatcca aaaaaatgtc tgttacagga actgag                                36

<210> SEQ ID NO 21
<211> LENGTH: 35
<212> TYPE: DNA
<213> ORGANISM: Artificial Sequence
<220> FEATURE:
<223> OTHER INFORMATION: Oligonucleotide (YDMC-3'Pst) for amplifying and
``` modifying target gene (ScDMC1)

<400> SEQUENCE: 21
aactgcagct actagtcact tgaatcggta atacc         35

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide (YDMC-G126D-sense) for
      amplifying and modifying target gene (ScDMC1)

<400> SEQUENCE: 22
ggtgaattta ggtgtgataa gacacagatg tctc         34

<210> SEQ ID NO 23
<211> LENGTH: 34
<212> TYPE: DNA
<213> ORGANISM: Artificial Sequence
<220> FEATURE:
<223> OTHER INFORMATION: Oligonucleotide (YDMC-G126D-antisense) for
      amplifying and modifying target gene (ScDMC1)

<400> SEQUENCE: 23
gagacatctg tgtcttatca cacctaaatt cacc         34

<210> SEQ ID NO 24
<211> LENGTH: 33
<212> TYPE: DNA
<213> ORGANISM: Artificial Sequence
<220> FEATURE:
<223> OTHER INFORMATION: Oligonucleotide (YDMC-N263Y-sense) for
      amplifying and modifying target gene (ScDMC1)

<400> SEQUENCE: 24
gcagtatttc tgacatacca agttcaatca gac          33

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide (YDMC-N263Y-antisense) for
      amplifying and modifying target gene (ScDMC1)

<400> SEQUENCE: 25
gtctgattga acttggtatg tcagaaatac tgc          33

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide (YDMC-A288T-sense) for
      amplifying and modifying target gene (ScDMC1)

<400> SEQUENCE: 26
gagggcacgt tctgacacat gcgtcagc               28

<210> SEQ ID NO 27
<211> LENGTH: 28
<212> TYPE: DNA
<213> ORGANISM: Artificial Sequence
<220> FEATURE:
<223> OTHER INFORMATION: Oligonucleotide (YDMC-A288T-antisense) for
      amplifying and modifying target gene (ScDMC1)

```
<400> SEQUENCE: 27
gctgacgcat gtgtcagaac gtgccctc                                             28

<210> SEQ ID NO 28
<211> LENGTH: 37
<212> TYPE: DNA
<213> ORGANISM: Artificial Sequence
<220> FEATURE:
<223> OTHER INFORMATION: Oligonucleotide (YR51-5'Bam) for amplifying
      and modifying target gene (ScRAD51)

<400> SEQUENCE: 28
gggggatcca aaaaaatgtc tcaagttcaa gaacaac                                   37

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide (YR51-3'Pst) for amplifying and
      modifying target gene (ScRAD51)

<400> SEQUENCE: 29
aactgcagtt actactcgtc ttcttctctg ggg                                       33

<210> SEQ ID NO 30
<211> LENGTH: 35
<212> TYPE: DNA
<213> ORGANISM: Artificial Sequence
<220> FEATURE:
<223> OTHER INFORMATION: Oligonucleotide (YRAD51-G190D-sense) for
      amplifying and modifying target gene (ScRAD51)

<400> SEQUENCE: 30
cggtgaattc aggacagata agtcccagct atgtc                                     35

<210> SEQ ID NO 31
<211> LENGTH: 39
<212> TYPE: DNA
<213> ORGANISM: Artificial Sequence
<220> FEATURE:
<223> OTHER INFORMATION: Oligonucleotide (YR52-5'Pme) for amplifying and
      modifying target gene (ScRAD52)

<400> SEQUENCE: 31
aaagaattcg tttaaacatg gcgttttttaa gctattttg                                39

<210> SEQ ID NO 32
<211> LENGTH: 33
<212> TYPE: DNA
<213> ORGANISM: Artificial Sequence
<220> FEATURE:
<223> OTHER INFORMATION: Oligonucleotide (YR52-3'Not) for amplifying and
      modifying target gene (ScRAD52)

<400> SEQUENCE: 32
atcgcggccg ctcatcaagt aggcttgcgt gca                                       33

<210> SEQ ID NO 33
<211> LENGTH: 34
<212> TYPE: DNA
<213> ORGANISM: Artificial Sequence
<220> FEATURE:
<223> OTHER INFORMATION: Oligonucleotide (YR54-5'RI) for amplifying and
      modifying target gene (ScRAD54)
```

```
<400> SEQUENCE: 33
ggggaattca aaaaaatggc aagacgcaga ttac                          34

<210> SEQ ID NO 34
<211> LENGTH: 36
<212> TYPE: DNA
<213> ORGANISM: Artificial Sequence
<220> FEATURE:
<223> OTHER INFORMATION: Oligonucleotide (YR54-3'Pst) for amplifying and
      modifying target gene (ScRAD54)

<400> SEQUENCE: 34
aaactgcagt catcaatgtg aaatatattg aaatgc                        36

<210> SEQ ID NO 35
<211> LENGTH: 33
<212> TYPE: DNA
<213> ORGANISM: Artificial Sequence
<220> FEATURE:
<223> OTHER INFORMATION: Oligonucleotide (YSPO-5'Bam) for amplifying and
      modifying target gene (ScSPO11)

<400> SEQUENCE: 35
atcggatcca aaaaatggc tttggaggga ttg                            33

<210> SEQ ID NO 36
<211> LENGTH: 35
<212> TYPE: DNA
<213> ORGANISM: Artificial Sequence
<220> FEATURE:
<223> OTHER INFORMATION: Oligonucleotide (YSPO-3'Pst) for amplifying and
      modifying target gene (ScSPO11)

<400> SEQUENCE: 36
gggctgcagt catcatttgt attcaaaaat tctgg                         35

<210> SEQ ID NO 37
<211> LENGTH: 33
<212> TYPE: DNA
<213> ORGANISM: Artificial Sequence
<220> FEATURE:
<223> OTHER INFORMATION: Oligonucleotide (YSPO-Y135F-sense) for
      amplifying and modifying target gene (ScSPO11)

<400> SEQUENCE: 37
gtgagagata tcttcttctc caacgtggaa ttg                           33

<210> SEQ ID NO 38
<211> LENGTH: 33
<212> TYPE: DNA
<213> ORGANISM: Artificial Sequence
<220> FEATURE:
<223> OTHER INFORMATION: Oligonucleotide (YSPO-Y135F-antisense) for
      amplifying and modifying target gene (ScSPO11)

<400> SEQUENCE: 38
caattccacg ttggagaaga agatatctct cac                           33

<210> SEQ ID NO 39
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 39
```

```
ggatccaaaa aaatggctcc taagaagaag agaaaggttg gaggaggacc cggg          54
```

<210> SEQ ID NO 40
<211> LENGTH: 362
<212> TYPE: PRT
<213> ORGANISM: Arabidopsis thaliana

<400> SEQUENCE: 40

```
Met Glu Gly Lys Phe Ala Ile Ser Glu Ser Thr Asn Leu Leu Gln Arg
 1               5                  10                  15

Ile Lys Asp Phe Thr Gln Ser Val Val Asp Leu Ala Glu Gly Arg
                20                  25                  30

Ser Pro Lys Ile Ser Ile Asn Gln Phe Arg Asn Tyr Cys Met Asn Pro
            35                  40                  45

Glu Ala Asp Cys Leu Cys Ser Ser Asp Lys Pro Lys Gly Gln Glu Ile
 50                  55                  60

Phe Thr Leu Lys Lys Glu Pro Gln Thr Tyr Arg Ile Asp Met Leu Leu
 65                  70                  75                  80

Arg Val Leu Leu Ile Val Gln Gln Leu Leu Gln Glu Asn Arg His Ala
                    85                  90                  95

Ser Lys Arg Asp Ile Tyr Tyr Met His Pro Ser Ala Phe Lys Ala Gln
                100                 105                 110

Ser Ile Val Asp Arg Ala Ile Gly Asp Ile Cys Ile Leu Phe Gln Cys
            115                 120                 125

Ser Arg Tyr Asn Leu Asn Val Val Ser Val Gly Asn Gly Leu Val Met
130                 135                 140

Gly Trp Leu Lys Phe Arg Glu Ala Gly Arg Lys Phe Asp Cys Leu Asn
145                 150                 155                 160

Ser Leu Asn Thr Ala Tyr Pro Val Pro Val Leu Val Glu Glu Val Glu
                165                 170                 175

Asp Ile Val Ser Leu Ala Glu Tyr Ile Leu Val Val Glu Lys Glu Thr
                180                 185                 190

Val Phe Gln Arg Leu Ala Asn Asp Met Phe Cys Lys Thr Asn Arg Cys
            195                 200                 205

Ile Val Ile Thr Gly Arg Gly Tyr Pro Asp Val Ser Thr Arg Arg Phe
        210                 215                 220

Leu Arg Leu Leu Met Glu Lys Leu His Leu Pro Val His Cys Leu Val
225                 230                 235                 240

Asp Cys Asp Pro Tyr Gly Phe Glu Ile Leu Ala Thr Tyr Arg Phe Gly
                245                 250                 255

Ser Met Gln Met Ala Tyr Asp Ile Glu Ser Leu Arg Ala Pro Asp Met
                260                 265                 270

Lys Trp Leu Gly Ala Phe Pro Ser Asp Ser Glu Val Tyr Ser Val Pro
            275                 280                 285

Lys Gln Cys Leu Leu Pro Leu Thr Glu Glu Asp Lys Lys Arg Thr Glu
        290                 295                 300

Ala Met Leu Leu Arg Cys Tyr Leu Lys Arg Glu Met Pro Gln Trp Arg
305                 310                 315                 320

Leu Glu Leu Glu Thr Met Leu Lys Arg Gly Val Lys Phe Glu Ile Glu
                325                 330                 335

Ala Leu Ser Val His Ser Leu Ser Phe Leu Ser Glu Val Tyr Ile Pro
                340                 345                 350

Ser Lys Ile Arg Arg Glu Val Ser Ser Pro
            355                 360
```

MODULATION OF MEIOTIC RECOMBINATION

CROSS REFERENCE TO RELATED APPLICATIONS

The present application is a divisional U.S. application Ser. No. 10/380,687, filed Aug. 11, 2003, now U.S. Pat. No. 8,716, 022, which claims priority to PCT/CA01/01306 filed Sep. 12, 2001 which claims priority to U.S. Provisional Patent Application Ser. No. 60/256,490 filed Dec. 20, 2000 and 60/249, 296 filed Nov. 17, 2000.

FIELD OF THE INVENTION

The invention is in the field of genetic manipulation of eukaryotic cells and organisms, particularly the modulation of homologous recombination between non-sister chromatids in meiosis.

REFERENCE TO SEQUENCE LISTING

The present application is filed along with a Sequence Listing in electronic format. The Sequence Listing is provided as a file entitled 17501863_1. TXT, created Mar. 17, 2014, which is approximately 43.1 Kb in size. The information in the electronic format of the Sequence Listing is incorporated herein by reference in its entirety.

BACKGROUND OF THE INVENTION

Mitosis and meiosis are in many ways opposite processes. A principal role of DNA recombination in mitotic cells is to preserve the fidelity of genetic information and ensure that it is faithfully reproduced and passed on to daughter cells. In contrast, DNA recombination during meiosis acts to create new permutations of genetic information by facilitating reshuffling or intermixing of the maternal and paternal genomes during gamete formation to enable production of offspring with novel genomes as compared to either parent. The different purposes of DNA recombination in meiotic versus mitotic cells are reflected in the very different rolls and mechanisms of homologous recombination in each cell type [1-5; 7; 8].

There is a fundamental mechanistic distinction between the primary processes of homologous recombination in meiotic (germ-line) cells compared to mitotic (vegetative/somatic) cells. In meiotic cells, homologous recombination occurs primarily between non-sister chromatids (to shuffle the genome), whereas in mitotic cells homologous recombination occurs primarily between sister chromatids (to correct genomic errors). Sister chromatids are replicated copies of a particular maternal or paternal chromosome. Recombination between non-sister chromatids (i.e. between a paternal chromatid and a maternal chromatid) occurs 500-1000 fold more frequently in meiotic cells versus mitotic cells [48;50]. The meiotic process of non-sister chromatid exchange (NSCE) facilitates novel recombination of the genetic information from two parents of the organism. In contrast, the mitotic process of sister-chromatid exchange (SCE) resulting from recombination-mediated repair is a primary mechanism for maintaining genome fidelity throughout a multi-cellular organism.

There are a significant number of mechanical distinctions between mitotic SCE and meiotic NSCE, as these processes are currently understood. Physical interactions and recombination between meiotic chromosomes is associated with formation and function of the synaptonemal complex which is a unique proteinaceous structure that assembles during meiosis and participates in enabling pairing and exchange between non-sister chromatids [156; 157; 158; 159; 160]. Double-strand breaks in meiotic recombination are understood to be catalysed by a conserved, specific enzyme, SPO11 [4;9-11], whereas in mitotic cells double-strand breaks generally result from spontaneous lesions [3;7]. Upon formation of double strand breaks in either SCE or NSCE, the exposed double-stranded ends are understood to be resected by an exonuclease activity that degrades the DNA to generate single-stranded DNA (ssDNA) ends which have a 3'-hydroxyl group. This resection process is understood to be catalysed by a protein complex composed of at least three known proteins, MRE11, RAD50 and XRS2/NBS1 which are conserved from yeast to plants and humans [12-19]. The ssDNA ends may then be acted upon by another set of proteins so that the ends invade the sister chromatid in mitotic cells or, uniquely, the chromatid of the paired homologous chromosome from the other parent in meiotic cells.

Strand invasion may be catalysed by a group of proteins which are known as RecA homologues as a consequence of their sequence and functional similarity to the *Escherichia coli* RecA protein. RecA has been extensively studied and has been demonstrated in vitro to catalyse pairing between homologous DNA molecules and strand invasion [6]. Yeast are reported to have at least four proteins with homology to RecA: RAD51; RAD55; RAD57; and DMC1 [5]. These proteins are also highly conserved in plants and humans [21;22; 24;25;39]. Eukaryotic RecA homologues also catalyse pairing between homologous DNA molecules and strand invasion [51;52]. Genetic studies illustrate the primacy of this group of proteins in mitotic and meiotic homologous recombination [13;20;23;53-57]. These biochemical and genetic studies demonstrate the high conservation of function of RecA homologues from lower to higher eukaryotes. Whereas RAD51, RAD55 and RAD57 play a role in both mitotic and meiotic homologous recombination [23;56], DMC1 functions in a meiosis-specific manner [20;54;55]. Biochemical and genetic evidence points to RAD51, RAD55 and RAD57 interacting in a common pathway whereas DMC1 acts in a unique but overlapping pathway [53;56]. The existence of two unique pathways of RecA homologues acting during meiosis is also supported by cytological studies whereby DMC1 and RAD51 are found at different nodes along the chromosome undergoing recombination [53]. RAD51, RAD55 and RAD57 may only facilitate homologous recombination on DNA molecules with a specific structure and topology unique to this group of proteins [59]. It has been proposed that DMC1 may act on specific DNA structures, potentially not recognized by RAD51, RAD55 or RAD57, to promote pairing and recombination between homologous maternal and paternal chromosomes and catalyse NSCE [53; 60]. These DNA structures may be meiosis-specific, again illustrating the unique attributes of homologous recombination involving NSCE during meiosis versus SCE in mitotic cells.

While RAD51 and DMC1 can apparently catalyse pairing and strand invasion alone, they also act in concert with other proteins that enhance homologous recombination. For example, RAD51 physically interacts with RAD54 [61;62] and RAD52 [42] and both of these proteins are conserved from yeast to humans [64;65]. Inclusion of RAD54 or RAD52 in in vitro assays demonstrate these proteins can stimulate the pairing and strand invasion activity of RAD51 [23;66]. DMC1 does not physically interact with RAD54 [53] but does interact with a RAD54 homologue, known as TID1

[53], which acts in NSCE during meiosis [49]. This again illustrates the uniqueness of the homologous recombination pathways catalysed by DMC1 versus RAD51. In addition to the promoting effects of RAD54 and RAD52, homologous recombination is enhanced by a complex of proteins which bind ssDNA. In eukaryotes, this protein complex is a heterotrimer known as RPA [26]. ssDNA-binding proteins function in DNA recombination and repair by reducing secondary structure in ssDNA thereby increasing the ability of RecA-like proteins to bind and act upon the ssDNA [67]. RPA is conserved from yeast to humans [26]. RPA has been demonstrated to physically interact with RAD51 and DMC1 [68], as well as associating with RAD52 [69], and may thereby act in recruiting RecA-homologues and/or other recombination proteins to recombinogenic ends, or assist in forming recombinogenic DNA-protein complexes.

Other participants in the pairing and strand exchange processes leading to homologous recombination in meiotic cells include MSH4, MSH5 and MLH1[27;29;31]. These proteins are also conserved from yeast to plants and humans [28;30; 32;33]. MLH1 functions principally in mismatch repair to ensure fidelity of DNA replication in vegetative cells but also plays a role in homologous recombination in meiotic cells [31]. MSH4 and MSH5 are meiosis-specific homologues of a set of proteins, unique from MLH1, which function in mismatch repair in vegetative cells [27; 29]. The biochemical role of MSH4 and MSH5 during meiosis is unclear as yet but evidence points to these proteins participating in DNA exchange between homologous chromosomes [27; 29]. The specificity of MSH4 and MSH5 to homologous recombination in meiotic cells again points to the uniqueness of this homologous recombination process versus that which occurs in vegetative cells.

Strand invasion and formation of the initial crossover or chiasma between the sister chromatids in vegetative cells and non-sister chromatids in meiotic cells is followed by branch migration, DNA replication and strand displacement. This increases the length of genetic information exchanged between the two chromatids. A second chiasma then occurs. The chiasma are acted upon by an enzyme known as a resolvase. This family of enzymes recognize and bind the cruciform structure created by the chiasma between the paired chromatids. Resolvases have been well characterized in microorganisms, including lower eukaryotes[43; 44], and the activity has been detected in humans [161].

It has been suggested that recombinases may be used to stimulate mitotic homologous recombination between sister chromatids in eukaryotes, which has been proposed as a mechanism to promote gene targeting in vegetative/somatic cells [63;82;85;86]. Gene targeting generally involves the directed alteration of a specific DNA sequence in its genomic locus in vivo. Problems have however been reported with mitotic gene targeting. It has for example been found that overexpression of RecA-homologues in mitotic cells may cause cell cycle arrest [92]. International Patent Publication WO 97/08331 dated 6 Mar. 1997 summarizes a range of difficulties with earlier suggestions that the *E. coli* RecA recombinase would be useful for stimulating homologous mitotic recombination (as for example had been suggested in International Patent Publications WO 93/22443, WO 94/04032 and WO 93/06221). Utilization of *E. coli* RecA in eukaryotic cells is potentially problematic because the direction of strand transfer catalysed by RecA is the opposite to the direction of strand transfer catalysed by eukaryotic RecA homologues [52]. Nevertheless, overexpression of *E. coli* RecA has been reported to promote gene targeting approximately 10-fold in mouse cells [63] and less than two-fold in plants [82]. However, this latter result in plants also demonstrated a very low overall frequency of gene targeting, which would tend to cast doubt on the statistical significance of the result.

In the face of difficulties associated with the use of *E. coli* RecA in mitotic gene targeting, alternative enzymes have been used to catalyse homologous sister chromatid exchange in mitotic cells. For example, U.S. Pat. Nos. 5,780,296 and 5,945,339 disclose methods to promote homologous recombination using Rec2 as an alternative recombinase to overcome problems with the use of RecA [86]. It has been reported that overexpression of human RAD51 (hRAD51) can increase gene targeting frequency by 2-3 fold [85].

In applications other than gene targeting in mitotic cells, other studies have suggested that increased expression of *E. coli* RecA or RAD51 may increase the resistance of cells to radiation or other DNA damaging agents [82; 85; 87-89; 91], and enhance the frequency of intrachromosomal recombination [88;90;91] and sister-chromatid exchange [82]. It has also been suggested that increased RAD51 activity during meiosis has no effect on the viability of gametes, although no evaluation of homologous recombination in these cells was conducted [87]. Identification of mechanistic steps in meiotic homologous recombination has utilized genetic analysis of mutants to identify genes involved in homologous recombination and DNA repair, and mutants with reduced meiotic homologous recombination have been identified [9;20;23; 93]. Null-mutations typically have a severe effect on the whole meiotic process, and can affect viability of gametes [9;20;54;55;93-95] and have pleiotropic effects on the organism at different developmental stages or in different tissues or in response to environmental conditions. For example, rad51 null mutants may have decreased meiotic homologous recombination frequency but they also reportedly have poor DNA repair and resistance to environmental stresses and DNA damaging agents [96;97], as well as a lethal phenotype in embryos [95].

SUMMARY OF THE INVENTION

The present invention recognizes the need in the art for methods of modifying the frequency of non-sister chromatid exchange in meiosis to facilitate heritable genomic changes during gamete formation, for example to facilitate breeding of plants and animals and for gene targeting in meiotic cells. The invention provides methods of modifying the level of expression or functional activity of factors such as enzymes or other catalytic proteins or structural proteins alone or in concert, to modify the frequency of meiotic homologous recombination involving the exchange of genetic information between non-sister chromatids from homologous maternal and paternal chromosomes. The steps at which modulation may occur include: homologous chromosome pairing, doublestrand break formation; resection; strand invasion; branch migration; and resolution.

In one aspect, the invention provides methods of increasing meiotic homologous recombination in a eukaryote, comprising transforming a eukaryotic cell with a nucleic acid encoding an activator of meiotic homologous recombination. The nucleic acid encoding the activator of meiotic homologous recombination may be operably linked to a promoter, so that the transformed eukaryotic cell is capable of expressing the activator of meiotic homologous recombination. The transformed eukaryotic cell, or its progeny, may then be allowed to undergo meiosis to produce viable gametes under conditions wherein the activator of meiotic homologous recombination is active during meiosis to increase the frequency of homologous non-sister chromatid exchange (NSCE). In alternative embodiments, the activator of meiotic homologous recombination may be an enzyme or other catalytic protein or structural protein, or transcription factor controlling the expression thereof, involved in meiotic homologous recombination, such as a eukaryotic homologue of SPO11 [9-11], MRE11 [12-15], RAD50 [16;17], XRS2/NBS1 [18;19], DMC1 [20-22], RAD51 [21;23-25], RPA [26], MSH4 [27;28], MSH5 [29;30], MLH1 [31-33], RAD52 [34;35], RAD54 [36;37], TID1 [53], RAD55 [38;39], RAD57 [39;40], Rad59 [41;42] or Resolvase[43;44;161] or chromatin remodeling proteins [152-155] or synaptomemal complex proteins (proteins associated with assembly and function of the synaptonemal complex) [156; 157; 158; 163]. In some embodiments, the frequency of mitotic homologous sister chromatid exchange in the eukaryote may not be altered to a level detrimental to cell viability, growth or reproduction, while the frequency of meiotic homologous recombination is increased or decreased. The promoter may be regulatable by induction or repression or may be a meiosis-specific promoter or a promoter with enhanced expression during meiosis, i.e. a preferentially-meiotic promoter, or a promoter capable of expressing the activator at a level sub-inhibitory to vegetative cells. The invention includes non-human eukaryotes produced by such processes.

In alternative aspects, the invention provides methods of selectively inhibiting meiotic homologous recombination in a eukaryote. Such methods may involve transforming a eukaryotic cell with a nucleic acid encoding an inhibitor of meiotic recombination. The nucleic acid encoding the inhibitor of meiotic recombination may be operably linked to a promoter, such as a promoter regulated by induction or repression, meiosis-specific or preferentially-meiotic promoter, or a promoter capable of expressing the activator at a level sub-inhibitory to vegetative cells, so that the transformed eukaryotic cell may be capable of expressing the inhibitor of meiotic recombination. The transformed eukaryotic cell, or a descendant of the transformed eukaryotic cell, may then be allowed to undergo meiosis to produce viable gametes under conditions wherein the inhibitor of meiotic recombination is active during meiosis to decrease the level of homologous non-sister chromatid exchange. The inhibitor of meiotic recombination may be a dominant-negative form (such as a mutant endogenous protein or a mutant or wild-type heterologous protein) of an enzyme or other catalytic protein or a structural protein, or transcription factor controlling the expression thereof, involved in meiotic homologous recombination. In some embodiments, the frequency of mitotic homologous sister chromatid exchange in the eukaryote may not be altered to a level detrimental to cell viability, growth or reproduction, while meiotic homologous recombination is increased or decreased. The invention includes non-human eukaryotes produced by such processes.

In alternative aspects, the invention provides methods of plant and animal breeding, in which the frequency of non-sister chromatid exchange in meiotic homologous recombination is modulated, prior to crossing a gamete from the parent organism with a second gamete to obtain progeny. The invention includes non-human eukaryotes produced by such processes.

The invention also provides methods of genomic mapping and map-based gene cloning comprising modulating the frequency of non-sister chromatid exchange in meiotic homologous recombination in a first cell, crossing the first cell with a second cell, and measuring the genetic linkage between markers in a progeny cell.

DETAILED DESCRIPTION OF THE INVENTION

In one aspect of the invention, the frequency of homologous recombination between non-sister chromatids during meiosis is increased or decreased by specifically changing the activity level of one or more activators or inhibitors of meiotic homologous recombination, such as proteins involved in homologous recombination, to affect one or more steps of the homologous recombination process.

Taking advantage of the fact that meiotic homologous recombination between homologous non-sister chromatids first requires a double-strand break in one of the paired homologues, one aspect of the present invention facilitates an increase in the potential for homologous recombination events by increasing the number of double-strand breaks. Local chromatin structure plays an important role in the positioning and frequency of meiotic double-strand breaks leading to meiotic homologous recombination [151]. Chromatin structure remodeling may be a result of the action of two groups of enzymes highly conserved among eukaryotes: 1) ATP-dependent remodeling complexes, and 2) histone acetyltransferases and histone deacetylases [152-155]. Thus one may increase the frequency of double-strand breaks by modifying the activity level of chromatin remodeling enzymes to create chromatin structure that facilitates a greater incidence of double-strand break formation. This may be achieved, for example, by enhancing histone acetyl transferase activity. Conversely one may decrease the frequency of double-strand breaks by modifying the activity level of chromatin remodeling enzymes to create chromatin structure that is less amenable to double-strand break formation. This may be achieved, for example, by enhancing histone deacetylase activity. In addition to the manipulation of chromatin structure, the frequency of double-strand break formation may be achieved, for example, by increasing the level of SPO11 activity during appropriate stages in meiosis or other appropriate stages in the cell cycle. Conversely, one may reduce the frequency of homologous recombination during meiosis by suppressing the function or expression of SPO11 at appropriate stages in meiosis, to decrease the number of double-strand breaks available and, therefore, decrease the frequency of initiating DNA exchange between homologous chromosomes during meiosis.

In alternative embodiments, meiotic homologous recombination frequency may be modified by modifying the activity level of enzymes involved in resection of double-stranded DNA (dsDNA) to create ssDNA ends required for strand invasion of the paired homologous chromosome. Thus, activity of MRE11, RAD50 and/or XRS2/NBS1 could be increased to promote creation of recombinogenic ssDNA by increasing the number of double-strand breaks created by SPO11 being converted into recombinogenic ssDNA, to increase the frequency of meiotic homologous recombination. Conversely, frequency of meiotic homologous recombination may be decreased by reducing the activity of MRE11, RAD50 and/or XRS2/NBS1 so as to decrease the conversion of double-strand breaks created by SPO11 into recombinogenic ends. In addition, modifying the resection process may be used to increase gene targeting frequency by promoting conversion of gene targeting substrates to DNAs having recombinogenic ends, for example by increased activity of SPO11, MRE11, RAD50 and/or XRS2/NBS1.

In alternative embodiments, meiotic homologous recombination frequency may be modulated by modifying the activity of enzymes and structural proteins involved in pairing of homologous DNA and strand invasion. Thus, activity of RecA homologues such as RAD51 and DMC1 may be increased in meiosis to promote homologous DNA pairing of non-sister chromatids and initiation of crossovers by strand invasion. Increased activity levels of these proteins may increase conversion of recombinogenic ends created by MRE11, RAD50 and XRS2/NBS1 into functional crossover events thereby increasing homologous recombination frequency. Because RAD51 and DMC1 act in unique but overlapping pathways [53], one may modulate the homologous recombination frequency and frequency of NSCE by increasing the activity of DMC1 and RAD51 individually or in concert. Conversely, the activity level of DMC1 and RAD51 alone or in concert may be decreased to decrease the frequency of NSCE. Other RecA homologues such as RAD55 and RAD57 may also be used in this way in meiosis. In addition, other proteins participating in homologous DNA pairing and strand-invasion, such as MSH4, MSH5 and MLH1, may be used to increase or decrease meiotic homologous recombination frequency through modulating their activity levels at appropriate stages of meiosis. ssDNA-binding proteins such as EcSSB or RPA which may function coordinately with RecA homologues may also be used to modulate homologous recombination frequency. For example, during meiosis, reducing the level of RPA in the nucleus or the activity of RPA within the nucleus may affect the activity of RecA homologues during meiosis and change the homologous recombination frequency.

In alternative embodiments, meiotic homologous recombination frequency may be modulated by modifying the activity of proteins that act in conjunction with RecA homologues to promote DNA pairing and crossing-over. For example, meiotic homologous recombination may be increased by increasing activity level of RAD54 and TID1, alone or in concert, independently or coordinately with RAD51 and/or DMC1 (RAD51 activity is stimulated in vitro by inclusion of RAD54 [66] and TID1 is a homologue of RAD54 that physically interacts with DMC1 [53]). Conversely, meiotic homologous recombination frequency may be decreased by reduction of expression or activity level of RAD54 and/or TID1. In some embodiments, homologous recombination frequency may be modulated by regulating the expression and functional activity of these four proteins independently or in different permutations. This approach of modulating recombination frequency may also be used with other proteins that physically interact directly or indirectly and modify the activity of RecA homologues functioning during meiosis.

In alternative embodiments, meiotic homologous recombination frequency may be modulated by modifying the activity level of resolvase. Thus, activity of resolvase may be increased to promote resolution of crossovers thereby increasing the frequency of exchange of genetic information between non-sister chromatids. It has been reported that, of the total number of crossovers initiated between homologous chromosomes during meiosis, only a fraction are resolved to result in actual exchange of genetic information between the homologous chromosomes, with the rest dissolving without causing exchange of genetic information [72]. In another aspect of the invention, meiotic homologous recombination frequency may be decreased by reducing the level or functional activity of resolvase during meiosis.

In alternative embodiments, meiotic homologous recombination frequency may be modulated by modifying the assembly or function of the synaptonemal complex. Thus the action of proteins important in assembly and function of the synaptonemal complex such as potential regulatory proteins, like ATM [163] or MEK1 [157], or structural proteins, like HOP1 [156], RED1 [164], or ZIP1 [165], or functional homologues thereof, may be inhibited so as to impair formation of the synaptonemal complex and reduce homologous chromosome pairing by decreasing the frequency of non-sister chromatid exchange. In another aspect of the invention, assembly and function of the synaptonemal complex may be promoted to increase recombination frequency during meiosis.

In alternative embodiments, the activator or inhibitor of meiotic homologous recombination may be an anti-sense molecule or a co-suppressive nucleic acid. A co-suppressive nucleic acid is a nucleic acid that suppresses the expression of another nucleic acid by means of co-suppression. Anti-sense oligonucleotides, including anti-sense RNA molecules and anti-sense DNA molecules, generally act to block the translation of mRNA by binding to targeted mRNA and inhibiting protein translation from the bound mRNA. For example, anti-sense oligonucleotides complementary to regions of a DNA sequence encoding an enzyme involved in meiotic homologous recombination, such as DMC1, may be expressed in transformed plant cells during the appropriate developmental stage to down-regulate the enzyme. Alternative methods of down-regulating protein expression may include the use of ribozymes or other enzymatic RNA molecules (such as hammerhead RNA structures) that are capable of catalysing the cleavage of RNA (as disclosed in U.S. Pat. Nos. 4,987,071 and 5,591,610, incorporated herein by reference). The mechanism of ribozyme action generally involves sequence specific hybridization of the ribozyme molecule to complementary target RNA, followed by endonucleolytic cleavage. Additionally, antibodies or peptides which inhibit the activity of the target protein may be introduced or expressed in meiotic cells to suppress activity of the target protein.

It is well known in the art that some modifications and changes can be made in the structure of a polypeptide without substantially altering the biological function of that peptide, to obtain a biologically equivalent polypeptide. In one aspect of the invention, proteins that modulate meiotic recombination may differ from a portion of the corresponding native sequence by conservative amino acid substitutions. As used herein, the term "conserved amino acid substitutions" refers to the substitution of one amino acid for another at a given location in the peptide, where the substitution can be made without loss of function. In making such changes, substitutions of like amino acid residues can be made, for example, on the basis of relative similarity of side-chain substituents, for example, their size, charge, hydrophobicity, hydrophilicity, and the like, and such substitutions may be assayed for their effect on the function of the peptide by routine testing. In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Various aspects of the present invention encompass nucleic acid or amino acid sequences that are homologous to other sequences. As the term is used herein, an amino acid or nucleic acid sequence is "homologous" to another sequence if the two sequences are substantially identical and the functional activity of the sequences is conserved (for example, both sequences function as or encode a selected enzyme or promoter function; as used herein, the term 'homologous' does not infer evolutionary relatedness). Nucleic acid sequences may also be homologous if they encode substantially identical amino acid sequences, even if the nucleic acid sequences are not themselves substantially identical, a circumstance that may for example arise as a result of the degeneracy of the genetic code.

Two nucleic acid or protein sequences are considered substantially identical if, when optimally aligned, they share at least about 25% sequence identity in protein domains essential for conserved function. In alternative embodiments, sequence identity may for example be at least 50%, 70%, 75%, 90% or 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, J. Mol. Biol. 215:403-10 (using the published default settings). Software for performing BLAST analysis may be available through the National Center for Biotechnology Information (on the world-wide-web at www.ncbi.nlm.nih.gov). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs). The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9,1,0.87); PAM70 (10,1,0.87) BLOSUM80 (10,1,0.87); BLOSUM62 (11,1,0.82) and BLOSUM45 (14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In some embodiments, the invention provides methods of increasing meiotic homologous recombination in the context of methods for breeding agricultural species, and plants and animals produced by such processes. Increased recombination frequency may be desirable to facilitate breeding of agricultural species, for example by facilitating the exchange of alleles at tightly linked genetic loci. Where breeding stock are modified to increase the level of meiotic homologous recombination, for example, the effort required to identify progeny which have lost an undesirable allele at a genetic locus of interest may be reduced.

One aspect of the invention involves the modulation of meiotic homologous recombination frequency in plant breeding, for example of *Brassica* sp. In a prophetic example of such an embodiment, the following conditions may apply:

a) Locus 1:
controls a quality trait such as saturated fatty acid content in seed oil.
allele "A" confers high saturate content, which is undesirable in the context of this example.
allele "a" confers low saturate content, which is desirable in the context of this example.

b) Locus 2:
controls the agronomic trait of lodging which is related to stem rigidity.
allele "B" confers a weak stem which results in lodging of the crop causing it to be difficult to harvest.
allele "b" confers a rigid stem resulting in an upright plant at maturity that increases harvestability with reduced seed loss which is desirable because it may increase yield.

c) Variety X under development has the genotype "aB/aB" conferring desirable oil properties but poor harvestiblity because of susceptibility to lodging.

d) Accession line Z has the genotype "Ab/Ab" giving it the properties of poor oil quality but lodging resistance.

e) Locus 1 and 2 have tight genetic linkage to each other.

f) Goal: To remove the deleterious "B" allele at Locus 2 from Variety X and transfer into Variety X the lodging resistance trait conferred by the "b" allele at Locus 2 in Accession Line Z using sexual crosses between Variety X and Accession Z.

In such an example, with natural levels of meiotic recombination frequency, a large population may be required to represent a gamete with the desired "ab" genotype in the progeny resulting from the F1 plant. This is because Locus 1 and 2 are tightly linked resulting in few crossover events between the two loci carried by homologous chromosomes from Variety X and Accession Z in the F1 hybrid. Using the present invention to provide an increased meiotic homologous recombination frequency, the representation of the "ab" gamete in the progeny from the F1 may be increased. This is because increased homologous recombination potential results in more crossover events in the genome of the F1 hybrid. As a result, there is an increased chance for crossovers to occur between Locus 1 and 2 leading to a greater frequency of breaking the linkage between the desirable "a" allele for low saturate content and the undesirable "B" allele for increase lodging at the closely linked loci 1 and 2 to produce the highly desirable hybrid chromosome carrying the "a" allele for reduced saturate content and the "b" allele for reduced lodging. Thus the frequency of the "ab" gamete in the progeny will be increased versus that found under conditions of natural recombination frequency.

In one aspect of the invention, the 'enhanced recombination factor' is introduced into Variety X so that Variety X has increased meiotic homologous recombination potential. The 'enhanced recombination factor' conferring the increased homologous recombination potential may be detectable by a molecular marker. Variety X may then be sexually crossed with Accession Z and the resulting hybrid will have increased recombination potential. During gamete formation by this F1, frequency of crossovers and exchange of genetic information between homologous chromosomes from Variety X and Accession Z will be increased versus the wild-type situation. As a result, there will be increased chance of exchange between Locus 1 and 2 resulting in increased frequency of gametes with the desired "ab" genotype. Representation of the "ab" genotype in the F1 progeny will thus be increased versus the wild-type situation. When plants of interest carrying the "ab" genotype are found in the progeny, the factor conferring increased recombination frequency can be removed by backcrossing to Variety X. During gamete formation in this new plant meiotic homologous recombination and/or independent assortment of chromosomes during meiosis will cause the 'enhanced recombination factor' to segregate from Loci 1 and 2. By using molecular markers, the resultant progeny can be screened to identify plants which retain the "ab" genotype but no longer carry the 'enhanced recombination factor' and, thus, these plants will be restored to wild-type levels of meiotic homologous recombination. In alternative aspects of the invention, the 'enhanced recombination factor' may be removed from the genome of a particular plant line by flanking the 'enhanced recombination factor' with recognition sites for a site-specific recombinase. Exposing the plant line to the action of the site-specific recombinase will thus excise the 'enhanced recombination factor' from the genome of the plant line.

If meiotic homologous recombination frequency is increased during this breeding procedure, in accordance with the present invention, recombinants between the two loci would be at a higher frequency in the progeny, and the breeder may develop a new variety in a less expensive and more efficient manner.

An alternative aspect of the invention involves increasing meiotic homologous recombination to enhance efficiency of genetic mapping and map-based cloning, for example in agricultural species. Genetic distance between chromosomal loci is governed by meiotic recombination frequency between homologous chromosomes on which the loci under consideration are located. By monitoring the frequency of co-inheritance of phenotypic or molecular markers corresponding to the loci under consideration, the genetic distance and order of the loci can be established. If two loci, 1 and 2, are on the same chromosome but are physically separated by a large region of the chromosome, numerous opportunities exist for recombination events to occur along this long stretch of DNA to combine alleles carried by the maternal and paternal chromosomes at these loci. The loci are considered linked if the frequency of new combinations of maternal and paternal alleles at Loci 1 and 2 observed in the progeny is less than 50%. The genetic distance between the two loci corresponds to this frequency. If Loci 1 and 3 are physically closer to one another along the chromosome than Loci 1 and 2, then there is generally less chance of recombination to occur between these loci to make new combinations of maternal and paternal alleles at Loci 1 and 3. Again, this is determined by observing the frequency of coinheritance of allelic combinations in the progeny. By determining the frequency of combinations of alleles at Loci 1, 2 and 3 in the progeny, genetic distance and order of the loci can be determined. For example, if combinations of maternal and paternal alleles at locus 1 and 2 are found in the progeny at a frequency of 40%, and combinations between locus 2 and 3 are found to be 25%, but combinations between 1 and 3 are found to be 15%, then the order of the loci is 1-3-2 with map distances between the ordered loci being 15 and 25 units. This type of information can be compiled for loci conferring phenotypic effects as well as loci corresponding to molecular markers such as RFLP's, RAPD's, AFLP's, SNP's, and microsatellites [98-100]. Detailed genetic maps can be determined for agricultural organisms. In this manner, for example, molecular markers can be linked to desirable traits. The markers can then be used to assist breeders in transferring desirable traits to varieties that are released to producers.

Reliance on natural levels of meiotic homologous recombination frequency to determine the distance between markers may present difficulties with existing mapping techniques. For example, two markers may be deemed to be very tightly linked genetically but could still be physically separated by very long stretches of DNA. Thus the invention enabling enhanced meiotic recombination frequency will enable markers with tighter linkage to the target loci to be defined while reducing the population size required to do so versus what is possible when relying on natural levels of recombination frequency. Such markers with tighter linkage to the target locus will enable more reliable monitoring of the segregation of the desired locus in a breeding program.

Genetic maps defined with molecular markers may also be used to clone genes responsible for traits of interest. This process of map-based gene cloning involves linking molecular markers to the desired trait by determining the frequency of co-inheritance of molecular markers with the trait [98-100]. Once a marker has been found which is inherited at high frequency with the target trait, it can be used as a molecular probe to screen a DNA library of the organism to identify a fragment of DNA which encodes the cognate gene. One major difficulty with map-based gene cloning is that the relationship between genetic distance and physical distance can vary between species and even between different regions of the genome in a given species. Therefore a molecular marker may show absolute linkage to the target trait locus but it may be physically hundreds of kilobases away from the actual gene of interest. This makes identifying and cloning the actual gene responsible for the trait difficult because there may be vast stretches of DNA to evaluate in order to identify the gene. In addition, one might map more than one molecular marker showing absolute linkage to the target trait locus. However, using a reasonable population size, it may not be possible to identify which marker is physically closer to the target gene. Thus, while one marker may be 10 kilobases from the target gene and the other is 400 kilobases from the target gene, with conventional methods relying on natural levels of recombination frequency there may be no way of differentiating which of the two markers should be used to most efficiently clone the target gene. It would therefore be beneficial to map-based cloning projects to utilize the present invention to provide elevated meiotic homologous recombination levels so as to increase precision in determining genetic distance between molecular markers and target trait loci.

In an alternative aspect, the invention provides methods of decreasing meiotic homologous recombination, for example to enhance efficiency of breeding agricultural species. Decreased recombination frequency may be desirable in directed breeding of agricultural species to promote linkage drag, thereby maintaining genotypic integrity during sexual crosses conducted to introgress desirable traits. This may, for example, reduce the number of plants per backcross generation required to restore the genotype of the recurrent parent. For example, in plant breeding of *Brassica* sp., the following conditions may apply:

a) Variety X:—has favourable quality and agronomic characteristics and is an established variety in the industry but is susceptible to a disease due to allele "A" at Locus 1.
b) Accession Z:—has poor quality and agronomic characteristics but is resistant to the same disease due to allele "a" at Locus 1.
c) Goal: To transfer disease resistance trait from Accession Z to Variety X and maintain all of the favourable quality and agronomic characteristics of Variety X.

A conventional approach might involve a sexual cross between Variety X and Accession Z in an attempt to transfer the disease resistance trait to Variety X. During meiosis in the F1 plant, natural levels of recombination between Variety X and Accession Z homologous chromosomes may result in extensive mixing of the two genomes. This may indeed combine the favourable disease resistance allele "a" from Accession Z with a Variety X chromosome. However, many detrimental alleles responsible for poor quality and agronomic characteristics in Accession Z become intermixed with the favourable alleles from the Variety X genome. This may necessitate several rounds of backcrossing the hybrid plant to Variety X, the recurrent parent, to restore the favourable characteristics of Variety X while selecting for the disease resistance allele introduced from Accession Z. To restore the original genotype of Variety X might require in excess of seven backcross generations. Using the present invention, it may be desirable to expedite the process of variety development through the use of plants with modified meiotic homologous recombination frequency. An engineered decrease in meiotic homologous recombination frequency may be used to reduce the mixing of genomes and genetic information between Variety X and Accession Z, to provide a higher frequency of progeny from the initial hybrid which have the "a" allele conferring disease resistance transferred to the Variety X chromosome with the rest of the Variety X genome largely intact.

In alternative embodiments, variety X may be modified to have decreased meiotic homologous recombination potential by introduction of a 'suppressed-recombination factor'. The 'suppressed-recombination factor' conferring the decreased homologous recombination potential may be detectable by a molecular marker. Variety X may then be sexually crossed with Accession Z, so that the resulting hybrid will have decreased recombination potential. During gamete formation by this F1 plant, the frequency of meiotic crossovers and exchange of genetic information between homologous chromosomes from Variety X and Accession Z will be decreased compared to the wild-type frequency. Thus the frequency of F1 progeny plants containing high proportions of the Variety X genome and its favourable characteristics plus disease resistance may be increased versus that possible with wild-type levels of meiotic homologous recombination. When such plants are identified, they may be backcrossed to Variety X to remove vestiges of the Accession Z genome. During gamete formation in such a plant, meiotic homologous recombination and/or independent assortment of chromosomes during meiosis may cause the inhibitor of meiotic recombination, such as a 'suppressed-recombination factor', to segregate from the disease resistance gene. By using molecular markers, the resultant progeny may be screened to identify plants which retain the disease resistance gene in the favourable Variety X genome but no longer carry the 'suppressed-recombination factor' so that these plants may be restored to wild-type levels of meiotic homologous recombination. In alternative aspects of the invention, the 'suppressed-recombination factor' may be removed from the genome of a particular plant line by flanking the 'suppressed-recombination factor' with recognition sites for a site-specific recombinase. Exposing the plant line to the action of the site-specific recombinase will thus excise the the 'suppressed-recombination factor' from the genome of the plant line.

In an alternative aspect, the invention provides methods to increase meiotic homologous recombination leading to enhanced efficiency of gene targeting. Homologous recombination activities are at an elevated state in meiotic cells compared to mitotic cells in which recombination activities must generally be induced by DNA damage. Thus supplying gene targeting substrates to meiotic cells, in accordance with one aspect of the present invention, takes advantage of endogenous meiotic enzymes and DNA states to promote recombination with the target locus. The present invention may also be used to increase recombination potential in meiotic cells to further enhance meiotic gene targeting frequency. In one aspect of the present invention, increasing one or more meiotic homologous recombination functions by providing an activator of meiotic homologous recombination can increase meiotic homologous recombination frequency. Thus, in accordance with this aspect of the invention, by supplying gene targeting substrate to meiotic cells one may increase gene targeting frequency. Gene targeting has been successfully applied in a variety of eukaryotic species including fungi [101], plants [82;102-104] and lower [105;106] and higher animals [63;85;107]. However, these gene targeting strategies involve only vegetative/somatic cells undergoing mitosis.

In one aspect of the present invention, increasing gene targeting frequency by performing the process in meiotic cells may facilitate the rapid generation of homozygous lines with targeted changes. In this aspect, the gene targeting event may occur at meiosis I, resulting in four gametes, each of which may have the targeted change. In plants and other monoecious organisms where both male and female gametes are produced by the same individual, simply self-crossing the individual may result in a high frequency of diploid progeny which are homozygous for the targeted genetic change. In addition, in the case of plants, one may obtain individuals homozygous for the targeted genetic change by performing microspore culture after delivering gene targeting substrate to the meiotic cells or the microspores themselves. Microspores are haploid cells resulting from meiosis in the plant anther. These cells may be cultured to regenerate entire plants. The plants may be chemically treated to create a diploid chromosome content so that they are homozygous for all genetic information. Therefore, microspores carrying the targeted genetic change as a result of treating meiotic cells or microspores with gene targeting substrate may be cultured and converted into plants that are homozygous for the targeted change. Alternatively, where male and female gametes are produced by different individuals, the gene targeting process may be done simultaneously in both a male and female plant, so that the male and female plants may be crossed. The gene targeting methods of the invention may be contrasted with conventional gene targeting strategies in which transformed organisms are hemizygous for the targeted change resulting in a need for further crosses to generate homozygous progeny. Conventional gene targeting strategies also generally rely on methods for regenerating organisms from transformed totipotent cells [82;102-104].

In one aspect of the invention, targeted changes in either maternal or paternal chromosomes may be obtained by delivering gene targeting substrate specifically to either female or male reproductive organs. This is not possible with conventional strategies that target somatic cells. Specific targeting of maternal or paternal derived chromosomes may for example be used to investigate and exploit such epigenetic processes as parental genomic imprinting.

In some aspects of the invention, transformed plant cells may be cultured to regenerate whole plants having a transformed genotype and displaying a desired phenotype as, for example, modified by the expression of a protein encoded by a recombinant nucleic acid construct mediated by a transcriptional regulatory region of the invention. A variety of plant culture techniques may be used to regenerate whole plants, such as are described in Gamborg and Phillips, "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., *Ann. Rev. of Plant Phys.* 38:467 (1987). A cell, tissue, organ, or organism into which has been introduced a foreign nucleic acid, is considered "transformed", "transfected", or "transgenic". A transgenic or transformed cell or organism also includes progeny of the cell or organism and progeny produced from a breeding program employing a transgenic plant as a parent in a cross and exhibiting an altered phenotype resulting from the presence of a recombinant nucleic acid construct. A transgenic plant is therefore a plant that has been transformed with a recombinant nucleic acid construct, or the progeny of such a plant that includes the transgene.

The invention provides vectors, such as vectors for transforming plants or plant cells. The term "vector" in reference to nucleic acid molecule generally refers to a molecule that may be used to transfer a nucleic acid segment(s) from one cell to another. One of skill will recognize that after the nucleic acid is stably incorporated in transgenic plants and confirmed to be operable, it can be introduced into other plants by sexual crossing. Any of a number of standard breeding techniques may be used, depending upon the species to be crossed.

In various embodiments, the invention comprises plants or animals transformed with the nucleic acids of the invention. Accordingly, an aspect of the invention relates to transformed embodiments of all higher plants, including monocots and dicots, such as, non-exclusively, species from the genera *Brassica, Sinapis, Triticum, Zea, Hordeum, Avena, Oriza, Glycine, Linum, Medicago, Lens, Pisum, Cicer, Solanum, Lycopersicon, Secale, Populus, Gossypium, Raphanus, Triflorium, Phaseolus, Bromus, Phleum, Agropyron, Helianthus, Beta, Malus, Prunus, Cucurbita, Phoenix, Abies, Acer, Quercus, Olea, Allium, Washingtonia, Papaver, Rosa, Carthamus, Vicia, Fragaria, Lotus, Onobrychis, Trigonelia, Vigna, Citrus, Geranium, Manihot, Daucus, Arabidopsis, Atropa, Capsicum, Picea, Prunus, Pyrus, Pinus, Hyoscyamus, Nicotiana, Arachus, Asparagus, Heterocatlis, Nemesia, Pelargonium, Panicum, Penniserum, Ranunculus, Senecio, Salpiglossis, Cucarnis, Browallia, Cedrus, Lolium, Sorghum, Datura, Petunia, Digitalis, Majorana, Cichorium, Lactuca, Antirrhinum*, and *Manihot*.

In one aspect, the invention includes mechanisms for achieving meiosis-specific or preferentially-meiotic expression, or activity, of factors that modulate meiotic homologous recombination. In one aspect, this may involve the use of meiosis-specific or preferentially meiotic promoters (i.e. promoters that are expressed exclusively or primarily during meiosis, respectively) operably linked to a gene of interest for expression during meiosis. Examples of such promoters may be found in the meiotic recombination factor genes described herein, including homologues obtainable from species from yeast to plants and animals. Specific examples of published promoters tested to be meiosis-specific are DMC1 [138] and MSH4 [27]. Additional promoters may be obtainable from genes that are expressed in meiosis-specific manner (for example, see [21]) or genes that are induced during meiosis [137]. Preferentially-meiotic promoters may include promoters active in vegetative cells or germ-line cells which lead to meiotic cells, wherein expression is mediated sufficiently close to the onset of meiosis. New promoters may be engineered to be meiosis-specific or preferentially meiotic, such as promoters that are initially active in both mitotic and meiotic cells. Such promoters may be modified by deletion or inactivation of mitotic expression elements so that their expression becomes preferential or specific during meiosis.

Certain transcription factors (e.g. NDT80) and promoter consensus sequences (e.g. URS1) are understood to be responsible for meiosis-specific expression [137]. Constitutive or vegetatively active promoters may be converted to meiosis-specific or preferentially-meiotic promoters by modifying the promoter to contain the recognition sequences for meiosis-specific transcription factors and to be active only when the promoter binds these transcription factors.

Bipartite promoters may be used to provide meiosis-specific expression. Bipartite systems consists of 1) a minimal promoter containing a recognition sequence for 2) a specific transcription factor. The bipartite promoter is inactive unless it is bound by the transcription factor. The gene of interest may be placed behind the minimal promoter so that it is not expressed, and the transcription factor may be linked to a meiosis-specific promoter. The transcription factor may be a naturally occurring protein or a hybrid protein composed of a DNA-binding domain and a transcription-activating domain. Because the activity of the minimal promoter is dependent upon binding of the transcription factor, the operably-linked coding sequence will not be expressed in vegetative cells. In meiotic cells, the meiosis-specific promoter will be turned on facilitating expression of the transcription factor. The transcription factor will act in trans and bind to the DNA recognition sequence in the minimal promoter via the cognate DNA-binding domain. The activation domain of the transcription factor will then be in the appropriate context to aid recruitment of RNA polymerase and other components of the transcription machinery. This will cause transcription of the target gene. With this bipartite system, the gene of interest will only be expressed in cells entering or undergoing meiosis since the necessary transcription factor is linked to a meiosis-specific promoter and will only be expressed at the desired developmental stage (i.e. the target gene will be expressed in a spatial and temporal pattern mirroring the meiosis-specific promoter expressing the transcription factor). In addition, a bipartite system could be used to coordinate expression of more than one gene during meiosis. Different genes could be placed behind individual minimal promoters all of which have the same recognition sequence for a specific transcription factor and whose expression, therefore, is reliant upon the presence of the transcription factor. The transcription factor is linked to a meiosis-specific promoter. Therefore, when cells enter meiosis, the promoter expressed the transcription factor which then can coordinately activate expression of the suite of target genes. Use of a bipartite system may have the advantage that if expression of the target genes is no longer required in a particular plant or animal line, then the transcription factor may be bred out, so that without the transcription factor present, the target gene(s) will no longer be expressed in this line. If the target genes are desired to be expressed at a later stage, the promoter::transcription factor locus may be bred back into the line. In addition, the bipartite system may be used to modulate the level of expression of a target gene. Bipartite promoters may be operably linked to a variety of sequences, such as:

1) positive factors to increase homologous recombination frequency: wild-type endogenous genes to facilitate overexpression of particular homologous recombination enzymes or other catalytic proteins or structural proteins or regulatory proteins; heterologous genes which promote homologous recombination; or, 2) negative factors to decrease homologous recombination frequency: altered endogenous proteins or wild-type or altered heterologous proteins capable of causing dominant-negative effect; anti-sense RNA to target genes; antibodies which bind and inhibit action of target proteins.

Minimal promoter elements in bipartite promoters may include, for example:

1) truncated CaMV 35S (nucleotides −59 to +48 relative to the transcription start site) [139];

2) DNA recognition sequences: E. coli lac operator [140, 141], yeast GAL4 upstream activator sequence [139]; TATA BOX, transcription start site, and may also include a ribosome recruitment sequence.

Bipartite promoters may for example include transcription factors such as: the yeast GAL4 DNA-binding domain fused to maize C1 transcription activator domain [139]; E. coli lac repressor fused to yeast GAL4 transcription activator domain [140]; or the E. coli lac repressor fused to herpes virus VP16 transcription activator domain [141].

Meiosis-specific promoters may be used directly to express factors for promoting or suppressing meiotic homologous recombination frequency by fusing the factor coding sequence to the promoter. However, some meiosis-specific promoters may promote transcription at too low of a level (i.e. weakly expressed) or at too high of a level (i.e. strongly expressed) to achieve the desired effect on homologous recombination frequency. Therefore, for example, a weak meiosis-specific promoter may be used to express a transcription factor which can promote a high level of expression when it binds to the minimal promoter adjacent to the target gene. Thus while the target gene might only be expressed at a low level if it was directly fused to the meiosis-specific promoter, this promoter can indirectly facilitate high level expression of the target gene by expressing a very active transcription factor. The transcription factor may be present at low levels but because it is so effective at activating transcription at the minimal promoter fused to the target gene, a higher level of expression of the target gene will be achieved than if the gene was directly fused to the weak meiosis-specific promoter. In addition, the transcription factor may also be engineered so that its mRNA transcript is more stable or is more readily translated, or that the protein itself is more stable. Conversely, if the meiosis-specific promoter is too strong for a desired application, it may be used to express a transcription factor with low ability to promote transcription at the minimal promoter adjacent to the target gene.

In alternative aspects of the invention, inducible promoters may be provided. A sequence encoding an inhibitor or activator of meiotic homologous recombination may be cloned behind an inducible or repressible promoter. The promoter may then be induced (or de-repressed) by appropriate external treatment of the organism when organismal development proceeds to a point when meiosis is initiated. Regulation of such promoters may be mediated by environmental conditions such as heat shock [142], or chemical stimulus. Examples of chemically regulatable promoters active in plants and animals include the ecdysone, dexamethasone, tetracycline and copper systems [143; 144; 145; 146; 147; 148].

In alternative embodiments, a meiosis-specific promoter may be used to express a heterologous RNA-polymerase which recognizes specific sequences not naturally present in the cell. For example, T7 RNA Polymerase may be used in eukaryotes to specifically promote transcription of a target gene linked to the T7 RNA Pol recruitment DNA sequence [149]. Genes affecting homologous recombination may then be regulated by the expression of T7 RNA Polymerase.

In some aspects, the present invention provides meiosis-specific expression of inhibitors or activators of meiotic homologous recombination (meiosis recombination factors), which may avoid deleterious effects that may otherwise be caused by expression of such factors during vegetative/mitotic growth. Constitutive expression of recombination factors, as exemplified here by RAD51, was found to severely inhibit cell proliferation: the growth rate of cells expressing the recombinase was reduced by approximately 5-fold versus the control, a result that is in accordance with observations made in animal cells where overexpression of recombinases has been found to inhibit cell proliferation by arresting cell division [92].

In alternative embodiments, the invention provides isolated nucleic acids and proteins. By isolated, it is meant that the isolated substance has been substantially separated or purified away from other biological components with which it would otherwise be associated, for example in vivo. The term 'isolated' therefore includes substances purified by standard purification methods, as well as substances prepared by recombinant expression in a host, as well as chemically synthesized substances.

In the context of the present invention, "promoter" means a nucleotide sequence capable of mediating or modulating transcription of a nucleotide sequence of interest, when the transcriptional regulatory region is operably linked to the sequence of interest. A transcriptional regulatory region and a sequence of interest are "operably linked" when the sequences are functionally connected so as to permit transcription of the sequence of interest to be mediated or modulated by the transcriptional regulatory region. In some embodiments, to be operably linked, a transcriptional regulatory region may be located on the same strand as the sequence of interest. The transcriptional regulatory region may in some embodiments be located 5' of the sequence of interest. In such embodiments, the transcriptional regulatory region may be directly 5' of the sequence of interest or there may be intervening sequences between these regions. The operable linkage of the transcriptional regulatory region and the sequence of interest may require appropriate molecules (such as transcriptional activator proteins) to be bound to the transcriptional regulatory region, the invention therefore encompasses embodiments in which such molecules are provided, either in vitro or in vivo.

The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Recombinant nucleic acid constructs therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination events. Transformation techniques that may be employed include plant cell membrane disruption by electroporation, microinjection and polyethylene glycol based transformation (such as are disclosed in Paszkowski et al. *EMBO J.* 3:2717 (1984); Fromm et al., *Proc. Natl. Acad. Sci. USA* 82:5824 (1985); Rogers et al., *Methods Enzymol.* 118:627 (1986); and in U.S. Pat. Nos. 4,684,611; 4,801,540; 4,743,548 and 5,231,019), biolistic transformation such as DNA particle bombardment (for example as disclosed in Klein, et al., *Nature* 327: 70 (1987); Gordon-Kamm, et al. "The Plant Cell" 2:603 (1990); and in U.S. Pat. Nos. 4,945,050; 5,015,580; 5,149,655 and 5,466, 587); *Agrobacterium*-mediated transformation methods (such as those disclosed in Horsch et al. *Science* 233: 496 (1984); Fraley et al., *Proc. Nat'l Acad. Sci. USA* 80:4803 (1983); and U.S. Pat. Nos. 4,940,838 and 5,464,763).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

EXAMPLES

To demonstrate methods for increasing and decreasing homologous recombination frequency during meiosis in accordance with various aspects of the present invention, *Saccharomyces cerevisiae* was used as a eukaryote model system. To demonstrate mechanisms for engineering modified meiotic homologous recombination frequency, proteins involved in different steps of the homologous recombination pathway have been utilized, including:

a) SPO11, which catalyses formation of the initial double-strand break in one member of a pair of aligned homologous maternal and paternal chromosomes. The double-strand break is then processed to become recombinogenic and participate in a cross-over event. SPO11 is highly conserved amongst eukaryotic species from yeast to plants and humans [9-11].

b) DMC1, which is a meiosis-specific RecA homologue that acts on ssDNA resulting from the processing of double-strand breaks created by SPO11. DMC1 facilitates the paring of homologous sequences on paired homologous chromosomes and catalyses invasion of the ssDNA strand into the paired duplex DNA of a non-sister chromatid. DMC1 accumulates only in meiotic cells [20; 21; 22; 138;] and appears to have no function in homologous recombination occurring in mitotic cells [20;49;53-55]. DMC1 is highly conserved amongst eukaryotic species from yeast to plants and humans [20-22]. DMC1 acts in a unique but overlapping pathway regarding other RecA homologues functioning during meiosis [53]. DMC1 is unique from RAD51 in that it forms octameric complexes when it binds ssDNA [108]. DMC1 also has proteins that interact with it during homologous recombination which are unique from those interacting with other RecA homologues [49;53].

c) RAD51, which is a RecA homologue that also acts on ssDNA resulting from the processing of double-strand breaks created by SPO11. RAD51 functions in both meiotic and mitotic cells [23;53;58]. RAD51 is highly conserved amongst eukaryotic species from yeast to plants and humans [21;23-25]. It is unique from DMC1 in that it forms a hexameric complex like *E. coli* RecA when it binds ssDNA [109;110]. It acts in a unique pathway from DMC1 and has proteins that specifically interact with it and not DMC1 [49;53;56].

d) MRE11, which is a nuclease that acts in resection of double-strand breaks created by SPO11 to provide ssDNA ends which are acted upon by RAD51 and DMC1 [4]. MRE11 is highly conserved amongst eukaryotic species from yeast to plants and humans [12-15]. MRE11 functions in both meiotic and mitotic cells [13;93;111;112].

e) ssDNA-binding proteins, which act to maintain ssDNA ends created by MRE11 and associated proteins free of secondary structure [67]. By doing so, the ssDNA ends are in an optimum topology for the action of RecA homologues like RAD51 and DMC1. ssDNA-binding proteins are highly conserved from yeast to humans [26]. Eukaryotic ssDNA-binding protein function is facilitated by a heterotrimeic complex known as RPA [26]. The ssDNA-binding protein in *E. coli.*, known as SSB, is an ancestor of the eukaryotic proteins [74;113]. SSB binds ssDNA principally as a homotetramer, but may also bind as a monomer [76]. As a result, SSB provides an efficient system to test the effect of modifying the cellular level of ssDNA-binding proteins on homologous recombination, versus studying the effects of each individual subunit of the eukaryotic heterotrimeric RPA. A cloned *E. coli* SSB gene was evaluated for its effect on meiotic homologous recombination frequency. To assist movement of this prokaryotic protein into the eukaryotic nucleus, it was engineered to encode a nuclear localization sequence derived from Simian virus 40 T-antigen [114].

In alternative aspects of the invention, homologous recombination frequency is increased by increasing the amount of a limiting factor through increased expression of the cognate gene, enhanced translational capacity of the cognate mRNA, decreased turnover of the protein or cognate mRNA, or by expressing an altered form of the protein with enhanced activity potential.

To reduce meiotic homologous recombination frequency, expression of the cognate gene for a target protein may be reduced, for example by antisense or cosuppression of the gene, by reducing translation of the cognate mRNA or increasing degradation of the mRNA or protein. Alternatively, activity of the target wild-type protein may be inhibited through coexpression of an alternative form of the protein that acts in a 'dominant' fashion to inhibit (i.e. 'negatively' affect) the activity of the endogenous wild-type protein. This 'dominant-negative' effect may result by one or more modes of action. A non-exclusive list of possible modes of action includes:

1) Titration of substrate, in which an alternate form of the protein of interest binds to the target substrate of the wild-type endogenous protein, wherein the alternate-form protein cannot complete the catalytic or other normal functions performed by the wild-type protein. By binding the substrate, the alternate-form protein titrates the substrate thereby inhibiting access to the substrate by the endogenous wild-type protein. The functional activity of the endogenous wild-type protein is therefore inhibited.

2) Titration of cofactors or co-members of protein complexes, in which the alternate-form protein binds to cofactors required for full activity of the endogenous wild-type protein; the cofactors may be organic or inorganic compounds or other proteins which are co-members of heteromeric protein complexes (i.e. the complex is composed of more than one type of protein). For example, many proteins, including those involved in many DNA recombination processes, act in multi-protein heteromeric complexes. If one member of the complex is absent or in limiting amounts, the function and activity level of the entire complex is reduced. Therefore if an alternate-form of a target protein, which may be non-functional or having reduced function itself but still capable of interacting with members of its normal protein complex, is expressed in a cell it can reduce activity of the endogenous wild-type protein by binding with and titrating members of the protein complex. These members of the complex are then no longer available to form functional complexes with the wild-type protein and, therefore, the function of the endogenous wild-type protein is reduced.

3) Direct inhibition of endogenous wild-type protein, in which the alternate-form protein may bind with the wild-type protein directly to inhibit its activity. Many proteins, including those participating in different steps of DNA recombination, form homomeric protein complexes (i.e. the complex is composed of a single type of protein). If one member of the homomeric complex is inactive in the correct biochemical context, it may poison (i.e. inhibit) the activity of the entire complex. Therefore, if an alternate-form protein, which has reduced or absent activity itself but which can still interact with endogenous wild-type protein to form complexes, is expressed in a cell it can reduce activity of the entire complex. The cell therefore has a combination of complexes composed of the following:

a) the alternate-form protein (which may directly titrate substrate (see "1"));
   b) hybrid complexes of the alternate-form protein and the endogenous wild-type protein. These complexes may have reduced or absent activity.
   c) homogenous endogenous wild-type protein complexes wherein the activity level and function of the wild-type complexes is reduced because i) there is decreased number of functional form homogenous wild-type complexes because of titration of wild-type protein into the hybrid complexes composed of alternate-form and wild-type protein monomers, and ii) there is decreased function of homogenous wild-type complexes because they may interact with hybrid complexes or homogenous alternate-form complexes and/or lose the competition for substrate which is titrated by the hybrid complexes or homogenous alternate-form complexes.

To assess the effect of alternative forms of recombination proteins on meiotic homologous recombination frequency, heterologous proteins were expressed and mutant proteins engineered to have reduced or no function. To demonstrate the effect of heterologous protein expression, the DMC1 gene from *Arabidopsis thaliana* (AtDMC1) was expressed during meiosis in *S. cerevisiae*. AtDMC1 has approximately 40% similarity to ScDMC1. In alternative embodiments, heterologous expression of AtDMC1 may, therefore, function to promote homologous recombination frequency by compensating for a potentially limiting amount of endogenous ScDMC1, or it may decrease homologous recombination frequency by a dominant-negative effect, as outlined above, due to direct or indirect inhibition of endogenous ScDMC1 activity. To demonstrate the effect of altered forms of recombination proteins on meiotic homologous recombination frequency, novel forms of DMC1, RAD51 and SPO11, and MRE11 were created and assessed. a) RAD51, a RecA homologue that catalyses strand exchange between homologous DNA [52]. ATP-binding is necessary for full activity in DNA pairing and strand exchange in vitro [115-117]. ATP-binding is facilitated by protein motifs known as Walker A and Walker B boxes [118]. Mutations inhibiting ATP binding and/or hydrolysis decrease biological activity of RAD51 regarding its role in recombination-mediated repair of DNA damage caused by radiation [96]. ScRAD51 and AtRAD51 were cloned and it was found that their protein sequences have 62% similarity and the conserved Walker A and B Box motifs. We engineered the genes to encode proteins with decreased ability for ATP-binding and hydrolysis by changing a glycine residue within the Walker A box to aspartic acid (i.e. ScRAD51: G190D; AtRAD51: G135D). The effect of these mutant protein forms on meiotic homologous recombination was then demonstrated. This glycine and other amino acid residues essential for homologous recombination activity are highly conserved amongst the RAD51-like family of proteins in eukaryotes. Other amino acids in the Walker A and B Box motifs may be changed to affect ATP-binding.

b) DMC1, a RecA homologue that catalyses strand exchange between homologous DNA [51]. ATP-binding motifs, Walker A and B boxes, are conserved in this family of proteins [20]. Genetic analysis demonstrates that wild-type sequence in the Walker A Box is essential for wild-type activity in vivo [53]. A mutant form of DMC1, DMC1-G126D which has a similar amino acid change at a corresponding residue in the Walker A box as outlined above for RAD51, was created. ScDMC1 and AtDMC1 were cloned and it was found that their protein sequences have 40% similarity and the conserved Walker A and B Box motifs. The genes were engineered to encode proteins with decreased ATP-binding and hydrolysis ability by changing a glycine residue within the Walker A box to aspartic acid (i.e. ScDMC1: G190D; AtDMC1: G135D). The effect of these mutant protein forms on meiotic homologous recombination was then demonstrated. Other amino acids in the Walker A and B Box motifs may be changed to affect ATP-binding. In some embodiments, identification of candidate mutations for interfering with DMC1 function may be predicted by alignment of DMC1 with RAD51 and EcRecA protein sequences. The crystal structure for EcRecA has been determined [119;120] so protein domains responsible for intra-complex and inter-complex interactions may be determined Therefore, through sequence alignments between DMC1 with RAD51 and EcRecA, one may predict which domains of DMC1 are involved in intra- and inter-complex interactions. These regions are highly conserved amongst DMC1 genes from many diverse species from yeast to plants and animals, including humans. ScDMC1 was cloned and engineered to encode mutations potentially responsible for:

i) ATP-binding and hydrolysis with mutation G126D;
ii) ATP-induced conformational change with mutation N263Y; and,
iii) monomer-monomer interactions with mutation A288T.

Combinations of these mutations were also created to evaluate any synergistic or additive effects resulting from two or more mutations in the same protein.

c) SPO11, a Type II topoisomerase [121] that is responsible for double-strand break formation in meiotic homologous recombination [9;121]. Type II topoisomerases have five conserved motifs which are also present in SPO11 proteins from low and high eukaryotic species [121]. Mutation of key amino acids in these motifs can inactivate SPO11. When such a mutant is present in a homozygous state, double-strand break formation is prevented [121] thereby inhibiting meiotic homologous recombination. ScSPO11 and AtSPO11 were cloned to demonstrate the use and application of SPO11 in a dominant-negative approach to reduce meiotic homologous recombination. The two protein sequences have approximately 20% sequence similarity and possess the five characteristic Type II topoisomerase motifs including a key tyrosine residue essential for catalytic activity [121]. Genes were engineered to encode proteins with decreased ability to generate double-strand breaks by changing the tyrosine residue in "Motif 1" (i.e. ScSPO11: Y135F; AtSPO11: Y103F). The effect of these mutant protein forms on meiotic homologous recombination was then demonstrated.

Key Amino Acid Residues in the Five Conserved Motifs Present in SPO11 Proteins

| Motif | Amino acid in TOPVIA from S. Shibata[a] | Corresponding amino acid in SPO11 from A. thaliana (SEQ ID NO: 40)[b] |
|---|---|---|
| 1 | Thr 100 | Ser 97 |
|   | Arg 102 | Arg 99 |
|   | Tyr 106 | Tyr 103 |
| 2 | Arg 150 | Arg 130 |
|   | Gly 161 | Gly 141 |
| 3 | Glu 209 | Glu 189 |
|   | Phe 214 | Phe 194 |
|   | Leu 217 | Leu 197 |
| 4 | Gly 235 | Gly 215 |
|   | Pro 237 | Pro 217 |
|   | Thr 241 | Thr 221 |
|   | Arg 242 | Arg 222 |
| 5 | Asp 261 | Asp 241 |
|   | Asp 263 | Asp 243 |
|   | Pro 264 | Pro 244 |
|   | Gly 266 | Gly 246 |
|   | Ile 269 | Ile 249 |

[a]The amino acid numbering for TOPVIA from S. Shibata is taken from FIG. 1 of Bergerat et al. (Bergerat, A. et al. 1997 Nature 386: 414-417).
[b]The amino acid numbering for SPO11 from A. thaliana (SEQ ID NO: 40) is taken from Hartung, F. and Puchta, H. (2000 Nucl Acid Res 28: 1548-1554).

d) MRE11, a nuclease responsible for resection of double-strand breaks created by SPO11 to provide ssDNA ends which are acted upon by RAD51 and DMC1 [4]. Phophoesterase motifs are conserved in this family of proteins. Biochemical analysis demonstrates mutation of key amino acids within these motifs can inactivate the nuclease activity of this protein and impair its biological activity [111;112;122]. Conserved amino acids outside of the phosphoesterase domains can also affect function of MRE11 [111]. AtMRE11 and ScMRE11 were cloned to demonstrate the use of MRE11 in a dominant-negative approach to reduce homologous recombination. AtMRE11 was engineered to encode a protein defective for phosphoesterase activity by changing a key amino acid residue in Motif I from aspartate to alanine (i.e. AtMRE11: Motif I:D-A).

A. Cloning and Evaluation of Target Genes

Target genes were cloned using specific oligonucleotides designed to prime DNA synthesis in a PCR reaction with either cDNA or genomic DNA (gDNA) from the appropriate species as template. The primers were designed to incorporate convenient restriction sites into the amplicon to facilitate initial cloning of the gene and its subcloning into various expression vectors. Genes cloned and the oligo primers used to achieve this are described in TABLE 1. PCR conditions were as described [123] or as recommended by the supplier of the thermostable DNA polymerase Pfu (Stratagene) or Taq (Pharmacia). PCR reactions were conducted using a thermocycler (Perkin-Elmer Model 9700).

1) AtDMC1

Template DNA was derived from a commercially available cDNA library of *Arabidopsis thaliana* ecotype Columbia in the vector lambda ZAP II (Stratagene). The library was mass-excised following the protocol supplied by the manufacture. The resultant phagemid suspension was concentrated by a combination of precipitation with polyethylene glycol as described by Ausubel et al. (1998) and desiccation using a SpeedVac (Savant). In this manner, the phagemid suspension was concentrated at least 5-fold. One hundred microlitres of the concentrated phagemid suspension was extracted with phenol and chloroform following standard procedures to remove protein and other contaminants from DNA with subsequent precipitation using ethanol [123]. In this manner, DNA from approximately 2 ml of phagemid suspension was concentrated and resuspended in 20 µl of LTE ((1 mM Tris-HCl, 0.1 mM EDTA (pH 8.0)) with RNase A (20 µg/ml)).

A primary PCR reaction was performed with 1 µl *Arabidopsis* cDNA library phagemid, 0.5 pmole OL11434, 0.5 pmole OL11433, 0.2 mM dNTP's (i.e. dATP, dCTP, dGTP, dTTP; Pharmacia), 1.25 U Pfu (Stratagene) and Pfu buffer constituents recommended by the manufacturer in a volume of 25 µl. The PCR conditions were 5 min @ 94 C, followed by 25 cycles of 30 s @ 94 C, 45 s @ 60 C and 2 min @ 72 C, followed by 10 min @ 72 C and storage at 4 C or –20 C. A secondary PCR was then performed with 2 µl of the above reaction used as template with 1.0 pmol OL11434 and 1.0 pmol OL11435 and other constituents as above except using 2.5 U Pfu and a final volume of 50 µl Two independent secondary reactions were done with identical PCR conditions as above. The two reactions were pooled and DNA fragments were resolved by agarose electrophoresis using a 1% gel and following standard procedures [123]. A DNA fragment of ~1 kilobase pair (kb) expected to correspond to AtDMC1 was excised and the DNA recovered from the agarose using the Qiaquick Gel Extraction Kit (Qiagen) and protocol supplied by the manufacturer. DNA was digested with XhoI and phosphorylated with T4-polynucleotide kinase following standard procedures [123]. The plasmid cloning vector pBluescript II KS—(Stratagene) was digested with EcoRV and XhoI. The amplicon and vector DNA were purified by agarose electrophoresis and recovered as above. Amplicon and vector DNA were then mixed in the presence of T4 DNA ligase (Gibco-BRL) to covalently link the two molecules following standard procedures [123] in a final volume of 25 µl After 2 h at room temperature, 1 µl of glycogen (20 mg/ml) was added to the ligation mixture made up to 100 µl with distilled water. After precipitation with ethanol [123], the DNA was resuspended in 4 µl of distilled water. *E. coli* strain DH5alpha (Gibco-BRL) was transformed with 2.5 µl of the concentrated ligation following standard procedures [123] and plated on sterile TYS medium (per litre distilled water: 10 g Tryptone (Difco); 5 g yeast extract (Difco); 5 g NaCl (Sigma); 15 g agar (Sigma)) containing ampicillin (100 µg/ml). Putative clones were propagated in liquid TYS (i.e. without agar) and ampicillin (100 µg/ml). Plasmid DNA was isolated by standard alkaline-lysis "mini-prep" procedure [123]. The DNA sequence of the resultant clone, pKR225, was determined at a commercial sequencing facility (Plant Biotechnology Institute, Saskatoon, Canada). Cloning of all other genes in this invention followed the same principles as for pKR225 with noted exceptions.

2) AtSPO11

A primary PCR reaction was performed with 2 µl *Arabidopsis* cDNA library phagemid (isolated as described for cloning of AtDMC1), 0.5 pmole AtSPO11-5'Sma oligo, 0.5 pmole AtSPO11-3'X oligo, 0.2 mM dNTP's, 1.25 U Pfu (Stratagene) and Pfu buffer constituents recommended by the manufacturer in a volume of 25 µl. The PCR conditions were 5 min @ 94 C, followed by 30 cycles of 30 s @ 94 C, 30 s @ 60 C and 2.5 min @ 72 C, followed by 10 min @ 72 C and storage at 4 C or –20 C. A secondary PCR was then performed with 2 µl of the above reaction used as template with 1.0 pmol AtSPO11-5'Sma oligo and 1.0 pmol AtSPO11-3'PstNot oligo and other constituents as per the primary PCR reaction except using 2.5 U Pfu and a final volume of 50 µl. Two independent secondary reactions were done with identical PCR conditions as above except replacing the step at 60 C with 63 C. The two reactions were pooled and DNA was digested with PstI. The plasmid cloning vector pBluescript II SK— (Stratagene) was digested with EcoRV and PstI. DNA fragments of interest corresponding to AtSPO11 (~1.1 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pTK82, was determined to confirm it encoded AtSPO11.

3. AtRAD51

Template for use in amplifying AtRAD51 was obtained from cDNA generated from RNA isolated from *A. thaliana* ecotype Columbia total plant tissues treated with gamma radiation. Plants were grown in sterile culture as follows. Seeds of *A. thaliana* ec. Columbia were surface sterilized by first rinsing in 70% (v/v) ethanol for one minute followed by washing for 5-7 min with a solution of 50% (v/v) bleach, 0.05% (w/v) Tween 20 (Sigma). After rinsing three times with sterile distilled water, the seeds were resuspended in 0.1% (w/v) agarose. Seeds were then dispensed in a grid pattern (~30 seeds/plate) with 1-2 cm spacing on sterile growth medium (0.5× Mirashige and Skoog basal salt media (Sigma) containing 1% (w/v) sucrose, nicotinic acid (1 µg/ml), thiamine-HCl (10 µg/ml), pyridoxine-HCl (1 µg/ml), myo-inositiol (100 µg/ml) and solidified with 1.0% (w/v) agar in 100 mm×15 mm or 150 mm×15 mm petri plates (Fisher). The plates were then placed at 4 C for 48 h and transferred to a controlled environment chamber with temperature of 18-22 C and a light regime of 16 h light and 8 h dark. After approximately 3 weeks plants were treated with gamma radiation using a Gamma-Cell 40 irradiator with a $Co^{60}$ radiation source. Plates containing plants were placed in the irradiator and left for time periods corresponding to desired dosages estimated from the calibrated emission from the radiation source and accounting for decay over time. Plant tissues were collected after 5-10 min recovery time and rapidly frozen using liquid $N_2$. For RNA extraction, plant tissues were first ground to a fine powder in the presence of liquid N2 using a mortar and pestle, and then RNA was isolated using the Rneasy Plant Kit (Qiagen) following the instructions provided by the manufacturer. cDNA was prepared from total RNA extracted from the plants exposed to 20 or 40 krad of gamma radiation using a SuperScript Preamplification System for First Strand cDNA Synthesis following directions of the manufacturer (GIBCO-BRL). First strand cDNA from 5-10 µg total RNA from plants treated with 20 or 40 krad of gamma radiation was primed using oligo-dT supplied with the kit.

A primary PCR reaction was performed with 4 µl first-strand cDNA from either the 20 krad or 40 krad treated plants, 0.5 pmole AtRAD51-5'Bam oligo, 0.5 pmole AtRAD51-3'X oligo, 0.2 mM dNTP's, 2.5 U Taq (Pharmacia) and Taq buffer constituents recommended by the manufacturer in a volume of 25 µl. The PCR conditions were 5 min @ 94 C, followed by 25 cycles of 30 s @ 94 C, 30 s @ 55 C and 75 s @ 72 C, followed by 10 min @ 72 C and storage at 4 C or −20 C. Two secondary PCR reactions were then performed for each of the above reactions using either 5 or 10 µl of the primary reactions in separate reactions as template with 1.0 pmole AtRAD51-5'Bam oligo and 1.0 pmole AtRAD51-3'Pst oligo and other constituents as above except using 5 U Taq and a final volume of 50 µl. Two independent secondary reactions were done for each template sample with identical PCR conditions as above. The two respective reaction series were pooled and DNA fragments were digested with BamHI and PstI. The plasmid cloning vector pBluescript II KS—(Stratagene) was digested with BamHI and PstI. DNA fragments of interest corresponding to AtRAD51 (~1.2 kb) and the vector (~3 kb) were purified by agarose gel electrophoresis and recovered from the agarose as described above. The fragments were ligated together, transformed into *E. coli* and putative clones of the gene identified as described above. Two clones were selected: pRH2 and pRH7 derived from cDNA from plants treated with 20 or 40 krad of gamma radiation, respectively. Determination of the DNA sequence of these clones revealed both had mutations at different positions of the open reading frame. To resynthesize a gene encoding a wild-type AtRAD51, restriction fragments from pRH2 and pRH7 were combined as follows: pRH2 was digested with XbaI and BamHI and a ~400 bp fragment was purified; pRH7 was digested with PstI and XbaI and a ~770 bp fragment was purified; both fragments were combined and ligated into pBluescript II KS— (Stratagene) digested with BamHI and PstI. The resulting clone, pRH15, was sequenced and found to encode a wild-type AtRAD51.

3. AtMRE11

Using the first 1000 bp of hMRE11 cDNA sequence [124] to query public DNA sequence databanks with the BLAST search algorithm [125], an *Arabidopsis* genomic sequence (ACCESSION #AB010695) was identified with some sequence homology. Based on this genomic DNA sequence, oligonucleotide primers were designed to amplify a ~450 bp fragment that would encode the ~250 bp of the 5' region of the putative AtMRE11 coding sequence and ~200 bp of a potential intron sequence. The ~450 bp fragment was amplified by PCR using genomic DNA from *A. thaliana* ec. Columbia which was isolated following the method of Junghans and Mezlaff (1990) [126]. Plants from which DNA was isolated were first grown at 18-22 C with 16 h light and 8 h dark for 3-4 wk. Aerial tissues were collected and rapidly frozen with liquid $N_2$ before storage at −80 C until processing. For PCR a primary reaction included 1.2 µg of genomic DNA, 0.5 pmole OL12414 oligo, 0.5 pmole OL12413 oligo, 0.2 mM dNTP's, 1.25 U Taq (Pharmacia) and Taq buffer constituents recommended by the manufacturer in a volume of 25 µl. The PCR conditions were 5 min @ 94 C, followed by 30 cycles of 30 s @ 94 C, 30 s @ 58 C and 1.0 min @ 72 C, followed by 10 min @ 72 C and storage at 4 C or −20 C. A secondary PCR was then performed with 2 µl of the above reaction used as template with 1.0 pmol OL12414 oligo and 1.0 pmol OL12415 oligo and other constituents as per the primary PCR reaction except using 2.5 U Taq and a final volume of 50 µl. Two independent secondary reactions were done with identical PCR conditions as above. The 450 bp fragment was purified by agarose gel electrophoresis and recovered from the gel as described above. Approximately 100 ng of this DNA fragment was labeled with alpha-$^{32}$P-dCTP by random priming as per standard procedure [123]. A cDNA library of *A. thaliana* ec. Columbia obtained from a commercial supplier (Stratagene) was plated on 150 mm×15 mm petri plates (Fisher) at a plaque density approaching confluence, following directions of the manufacturer. Plaque lifts from six such plates were performed using Hybond-N membranes (Amersham) following directions of the supplier. Membranes were probed with the radiolabelled 450 bp fragment following the method of Church and Gilbert (1984), with ~1×10$^6$ cpm of probe per millilitre of hybridization solution. Hybridization was performed overnight at 60 C using a rotisserie incubator (Robbins Scientific). Non-specific binding of the probe was reduced by washing membranes following standard procedures [123] with two 10 min washes at 22 C with 60-80 ml of 4.73×SSC, 0.1% (w/v) SDS, followed by two 30 min washes at 50 C with 60-80 ml of the same solution prewarmed to 50 C. Filters were then transferred to a solid support, wrapped in plastic film and placed in an X-ray cassette. After overnight exposure at −80 C, the film was developed and twelve putative clones (C1-C12) were identified which hybridized to the 450 bp fragment. These clones were purified from contaminating phage following standard procedures [123] and using the 450 bp fragment as probe with identical conditions as above. One clone, phi-C7A, was characterized further. The insert was isolated by conversion to plasmid vector following directions of the manufacturer (Stratagene) resulting in pKR242. pKR242 was sequenced using primers flanking the multiple cloning site of the vector, as suggested by the manufacturer (Stratagene), and OL12779 and OL12780 (Table 1). The entire sequence of pKR242 was determined and shown to encode an homologue MRE11 genes from other species. The cDNA, encoding the coding region of the gene was compared to the genomic sequence in the public database (ACCESSION #AB010695) which disclosed that the gene contains twenty introns. Comparison of predicted amino acid sequence encoded by pKR242 with other MRE11 protein sequences illustrated it was not full-length. Comparison of genomic DNA sequence to genes from other species enabled prediction of a putative start codon for AtMRE11. To clone the 5' portion of AtMRE11 not present in pKR242 PCR was employed. First-strand cDNA was synthesized from total RNA isolated from *A. thaliana* ec. Columbia treated with 30 krad of gamma radiation as described above. A primary PCR reaction was performed with 2 µl first-strand cDNA, 0.5 pmole OL12414 oligo, 0.5 pmole OL12413 oligo, 0.2 mM dNTP's, 1.25 U Pfu (Stratagene) and Pfu buffer constituents recommended by the manufacturer in a volume of 25 µl. The PCR conditions were 5 min @ 94 C, followed by 25 cycles of 30 s @ 94 C, 30 s @ 55 C and 60 s @ 72 C, followed by 10 min @ 72 C and storage at 4 C or −20 C. Two secondary PCR reactions were then performed using 2 µl of the primary reaction as template with 1.0 pmole OL12414 oligo and 1.0 pmole Ol 12415 oligo and other constituents as above except using 2.5 U Pfu and a final volume of 50 µl. The two reactions were pooled and DNA was digested with EcoRI and XbaI. The plasmid cloning vector pBluescript II KS— (Stratagene) was digested with EcoRI and XbaI. DNA fragments of interest corresponding to the 5' end of AtMRE11 (~225 bp) and the vector (~3 kb) were purified by agarose gel electrophoresis and recovered from the agarose as described above. The fragments were ligated together, transformed into *E. coli* and putative clones of the DNA fragment identified as described above. One clone, pRH1 was sequenced to confirm it encodes the 5' end of AtMRE11. To resynthesize a gene encoding a full-length AtMRE11, restriction fragments from pRH1 and pKR242 were combined as follows: pRH1 was digested with HindIII and XbaI and a ~225 bp fragment was purified; pKR242 was digested with XbaI and XhoI and a ~2. kb fragment was purified; both fragments were combined and ligated into pSPORT2 (Gibco-BRL) digested with HindIII and SalI. The resulting clone, pNH2 was sequenced and found to encode a wild-type AtMRE11. Comparison of the conceptual protein encoded by the cloned AtMRE11 gene to other MRE11 proteins from other organisms confirms it is a homologue of this family of proteins. The conservation extends to phophoesterase motifs which have been determined to be essential for the function of this family of proteins [111;112;122]. Alternate forms of AtMRE11 may be engineered to confer a dominant-negative effect as described above for other proteins. For example, the phosphesterase motifs responsible for nuclease activity are highly conserved within the MRE11 family. Mutations of different amino acids within these motifs may inactivate MRE11 function [111; 112;122]. Mutations outside of these motifs may also suppress function of the protein [111].

6. ScDMC1 a) Genomic Clone

ScDMC1 gene in yeast contains a single intron which may be excised in a meiosis-specific manner [20]. Template for amplifying ScDMC1 was genomic DNA from *Saccharomyces cerevisiae* strain RK1308 [128] isolated by standard procedure [123]. Two PCR reactions were performed with approximately 1 µg of genomic DNA, 1.0 pmol yDMC-5'Bam oligo and 1.0 pmol yDMC-3'Pst oligo, 0.2 mM dNTP's, 2.5 U Pfu (Stratagene) and Pfu buffer constituents recommended by the manufacturer in a volume of 50 µl. The PCR conditions were 5 min @ 94 C, followed by 25 cycles of 30 s @ 94 C, 30 s @ 55 C and 2 min @ 72 C, followed by 10 min @ 72 C and storage at 4 C or −20 C. The two reactions were pooled and DNA was digested with PstI. The plasmid cloning vector pBluescript II KS—(Stratagene) was digested with SmaI and PstI. DNA fragments of interest corresponding to ScDMC1 (~1.1 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pMW13, was determined to confirm it encoded ScDMC1-genomic.

b) cDNA Clone

Template for use in amplifying ScDMC1-cDNA was obtained from cDNA generated from RNA isolated from *S. cerevisiae* cells undergoing meiosis. Strain RK1308 [128] was grown in YPD liquid medium (1% (w/v) yeast extract, 2% (w/v) peptone, 2% (w/v) glucose) to cell density of ~2×10$^7$ cells/ml at 30 C with shaking at 225 RPM. Cells were collected by centrifugation, washed and resuspended in SPM medium (0.3% (w/v) potassium acetate, 0.02% (w/v) raffinose, 5 µg/ml uracil, 5 µg/ml histidine, 25 µg/ml leucine) then cultured as above for 2.5 h. Cells from 10 ml of culture were collected by centrifugation, washed with sterile distilled water (SDW) and resuspended in 1 ml SDW before rapid freezing in a dry-ice/methanol bath and stored at −80 C. Total RNA was extracted from these cells following a standard protocol [123]. Approximately 4 µg of RNA was used to create cDNA primed with oligo-dT using the Superscript Preamplification System for First Strand cDNA Synthesis (Gibco/BRL) following directions of the manufacturer. Two PCR reactions were performed with 3 µl of first strand cDNA, 1.0 pmol yDMC-5'Bam oligo and 1.0 pmol yDMC-3'Pst oligo, 0.2 mM dNTP's, 2.5 U Pfu (Stratagene) and Pfu buffer constituents provided by the manufacturer in a volume of 50 µl. The PCR conditions were 5 min @ 94 C, followed by 25 cycles of 30 s @ 94 C, 30 s @ 55 C and 2 min @ 72 C, followed by 10 min @ 72 C and storage at 4 C or −20 C. The two reactions were pooled and DNA was digested with PstI. The plasmid cloning vector pBluescript II KS— (Stratagene) was digested with SmaI and PstI. DNA fragments of interest corresponding to ScDMC1-cDNA (~1.1 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pMW19, was determined to confirm it encoded ScDMC1-cDNA.

7. ScRAD51

Template for amplifying ScRAD51 was genomic DNA from *Saccharomyces cerevisiae* strain AB972 [129] isolated by standard procedure [123]. Two PCR reactions were performed with approximately 1 µg of genomic DNA, 1.0 pmol yR51-5'Bam oligo and 1.0 pmol yR51-3'Pst oligo, 0.2 mM dNTP's, 2.5 U Pfu (Stratagene) and Pfu buffer constituents provided by the manufacturer in a volume of 50 µl. The PCR conditions were 5 min @ 94 C, followed by 25 cycles of 30 s @ 94 C, 30 s @ 58 C and 2.5 min @ 72 C, followed by 10 min @ 72 C and storage at 4 C or −20 C. The two reactions were pooled and DNA was digested with BamHI and PstI. The plasmid cloning vector pBluescript II KS— (Stratagene) was digested with BamHI and PstI. DNA fragments of interest corresponding to ScRAD51 (~1.2 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pMW35, was determined to confirm it encoded ScRAD51.

8. ScRAD52

Template for amplifying ScRAD52 was genomic DNA from *Saccharomyces cerevisiae* strain AB972 [129] isolated by standard procedure [123]. Two PCR reactions were performed with approximately 1 µg of genomic DNA, 1.0 pmol yR52-5'Pme oligo and 1.0 pmol yR52-3'Not oligo, 0.2 mM dNTP's, 2.5 U Pfu (Stratagene) and Pfu buffer constituents recommended by the manufacturer in a volume of 50 µl. The PCR conditions were 5 min @ 94 C, followed by 25 cycles of 30 s @ 94 C, 30 s @ 60 C and 2 min @ 72 C, followed by 10 min @ 72 C and storage at 4 C or −20 C. The two reactions were pooled and DNA was digested with EcoRI and NotI. The plasmid cloning vector pBluescript II SK— (Stratagene) was digested with EcoRI and NotI. DNA fragments of interest corresponding to ScRAD52 (~1.5 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pTK50, was determined to confirm it encoded ScRAD52.

9. ScRAD54

Template for amplifying ScRAD54 was genomic DNA from *Saccharomyces cerevisiae* strain AB972 [129] isolated by standard procedure [123]. Two PCR reactions were performed with approximately 1 µg of genomic DNA, 1.0 pmol yR54-5'RI oligo and 1.0 pmol yR54-3'Pst oligo, 0.2 mM dNTP's, 2.5 U Pfu (Stratagene) and Pfu buffer constituents recommended by the manufacturer in a volume of 50 µl. The PCR conditions were 5 min @ 94 C, followed by 25 cycles of 30 s @ 94 C, 30 s @ 60 C and 5 min @ 72 C, followed by 10 min @ 72 C and storage at 4 C or −20 C. The two reactions were pooled and DNA was digested with PstI. The plasmid cloning vector pBluescript II KS— (Stratagene) was digested with SmaI and PstI. DNA fragments of interest corresponding to ScRAD54 (~2.7 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pMW34, was determined to confirm it encoded ScRAD54.

10. ScSPO11

Template for amplifying ScSPO11 was genomic DNA from *Saccharomyces cerevisiae* strain AB972 [129] isolated by standard procedure [123]. Two PCR reactions were performed with approximately 1 µg of genomic DNA, 1.0 pmol ySPO-5'Bam oligo and 1.0 pmol ySPO -3'Pst oligo, 0.2 mM dNTP's, 2.5 U Pfu (Stratagene) and Pfu buffer constituents recommended by the manufacturer in a volume of 50 µl. The PCR conditions were 5 min @ 94 C, followed by 25 cycles of 30 s @ 94 C, 30 s @ 63 C and 2.5 min @ 72 C, followed by 10 min @ 72 C and storage at 4 C or −20 C. The two reactions were pooled and DNA was digested with BamHI and PstI. The plasmid cloning vector pBluescript II KS— (Stratagene) was digested with BamHI and PstI. DNA fragments of interest corresponding to ScSPO11 (~1.2 kb) and the vector (~3 kb) were purified by agarose gel electrophoresis and recovered from the agarose as described above. The fragments were ligated together, transformed into *E. coli* and putative clones of the gene identified as described above. The DNA sequence of the resultant clone, pTK81, was determined to confirm it encoded ScSPO11.

11. EcSSB

Template for amplifying SSB was genomic DNA from *E. coli* strain CC106 [130]. Genomic DNA from the strain was isolated as follows: 1) cells were cultured to mid-log phase in TYS liquid medium at 37 C; 2) cells were pelleted by centrifugation and washed with sterile distilled water; 3) 20 ml of cell culture was centrifuged and the cell pellet resuspended in 0.5 ml TE/Tween buffer (10 mM Tris-HCl (pH 8.0), 1 mM EDTA, 0.01% (w/v) Tween 20); 4) cells were incubated at 85 C for 20-30 min and then pelleted by microcentrifugation for 5-10 mM; 5) the supernatant was collected and 50 µl of TE-RNase (RNase A 20 µg/ml) was added before incubation at room temperature for 30 mM; 6) the supernatant was extracted with phenol and chloroform and precipitated with ethanol as per standard procedure [123]. 7) the DNA was resuspended in 20 µl of LTE (TE diluted 1:10 with distilled water).

The SSB gene was amplified with two primer sets to create two clones of the gene with different restriction sites at the 5' end. PCR reactions were performed with 4 µl of genomic DNA, 1.0 pmol SSB-5'Bam oligo and 1.0 pmol SSB-3'Pst oligo, or 1.0 pmol SSB-Sma oligo and 1.0 pmol SSB-3'Pst oligo, plus 0.2 mM dNTP's, 2.5 U Pfu (Stratagene) and Pfu buffer constituents recommended by the manufacturer in a volume of 50 µl. The PCR conditions were 5 min @ 94 C, followed by 25 cycles of 30 s @ 94 C, 30 s @ 55 C and 1.0 min @ 72 C, followed by 10 min @ 72 C and storage at 4 C or −20 C. The amplified DNA from the PCR reactions using SSB-5'Bam oligo and SSB-3'Pst oligo or SSB-5'Sma oligo and SSB-3'Pst oligo was digested with BamHI and PstI or SmaI and PstI, respectively. The corresponding plasmid cloning vector pBluescript II KS— (Stratagene) was also digested with BamHI and PstI or SmaI and PstI, respectively. DNA fragments of interest corresponding to SSB (~0.55 kb) and the vector (~3 kb) were purified by agarose gel electrophoresis and recovered from the agarose as described above. The fragments were ligated together, transformed into *E. coli* and putative clones of the SSB gene identified as described above. The DNA sequence of the resultant clones, pTK27 and pTK28, were determined to confirm they encoded SSB with flanking restriction sites of BamHI and PstI or SmaI and PstI, respectively.

A SSB derivative was also created so that the resultant protein would encode a nuclear localization sequence (i.e. NLS-SSB). A synthetic oligonucleotide was created which encoded the nuclear localization sequence (NLS) corresponding to that found in simian virus 40 T-antigen[114]. The nucleotide sequence (GGATCCAAAAAAATGGCTC-CTAAGAAGAAG-AGAAAGGTTGGAGGAGGAC-CCGGG) (SEQ ID NO: 39) encodes a BamHI site, in-frame start codon, and SmaI site (italicized). A plasmid containing this cloned NLS sequence and derived from pBluescript II KS— (Stratagene) was digested with SmaI and PstI and the DNA fragment corresponding to the vector (~3 kb) was gel purified. pTK28 was also digested with SmaI and PstI and the DNA fragment corresponding to the SSB gene (~0.55 kb) was also gel purified. The DNA fragments were recovered from agarose, ligated together, transformed into *E. coli* and putative clones of the NLS-SSB gene identified as described above. The DNA sequence of the resultant clone, pTK29, was determined to confirm it encoded NLS-SSB.

B. Engineering and Cloning of Altered Forms of Target Genes

Altered forms of genes were engineered to encode proteins with altered amino acid sequences and modified function. Site-directed mutagenesis was performed using the QuickChange Site-Directed Mutagenesis Kit (Stratagene), unless otherwise stated, following directions of the manufacturer using a thermocycler (Perkin-Elmer Model 9700) and the thermostable DNA polymerase Pfu (Stratagene). Base-pair changes of interest were incorporated into oligonucleotides which were then used to prime replication of an altered form of the target gene. Oligonucleotides used to incorporate the desired base changes in target genes are listed in TABLE 1.

1. DMC1

ScDMC1 was engineered to encode mutations potentially responsible for:

i) ATP-binding and hydrolysis with mutation ScDMC1: G126D;

ii) ATP-induced conformational change with mutation ScDMC1:N263Y;

iii) monomer-monomer interactions with mutation ScDMC1:A288T.

To create these mutations the protocol of the QuickChange Site-Directed Mutagenesis Kit (Stratagene) was followed. The mutagenesis reactions contained ~50 ng of pMW13 as template, the appropriate oligonucleotides and reaction constituents and Pfu polymerase (Stratagene) as recommended by the manufacturer. The reactions were incubated in a thermocycler for 30 s @ 95 C followed by 12 cycles of 30 s @ 95 C, 1 min @ 55 C and 8 min 20 s @ 68 C before storage at 4 C or −20 C. ScDMC1:G126D was created using oligos yDMC-G126D-sense and yDMC-G126D-antisense resulting in the plasmid pTK68-3. ScDMC1:N263Y was created using oligos yDMC-N263Y-sense and yDMC-N263Y-antisense resulting in the plasmid pTK70-5. ScDMC1:A288T was created using oligos yDMC-A288T-sense and yDMC-A288T-antisense resulting in the plasmid pTK64-1. All clones were sequenced to confirm the presence of the mutation.

Combinations of these mutations were also created using two methods. Firstly, the QuickChange Site-Directed Mutagenesis Kit (Stratagene) and supplied protocol were used with the template being one of the mutant gene forms from above and a oligonucleotide pair which confers a mutation at a different site. ScDMC1:G126D+A288T was created in a reaction containing ~50 ng of pTK64-1 (i.e. ScDMC1: A288T) as template with oligonucleotides yDMC-G126D-sense and yDMC-G126D-antisense resulting in the plasmid pTK67-3. Likewise ScDMC1:N263Y+A288T was created in a reaction containing ~50 ng of pTK64-1 (i.e. ScDMC1: A288T) as template with oligonucleotides yDMC-N263Y- sense and yDMC-N263Y-antisense resulting in the plasmid pTK69-6. Secondly, a combination of restriction fragments from various constructs was used to create genes with multiple mutations. ScDMC1:G126D+N263Y was created by digesting pTK68-3 (i.e. ScDMC1:G126D) with NdeI and PstI, purifying ~3.5 kb fragment and ligating to this a ~550 bp fragment purified from pTK70-5 (i.e. ScDMC1:N263Y) digested with NdeI and PstI resulting in the plasmid pTK71-1. Likewise ScDMC1:G126D+N263Y+A288T was created by digesting pTK68-3 (i.e. ScDMC1:G126D) with NdEI and PstI, purifying ~3.5 kb fragment and ligating this to a ~550 bp fragment purified from pTK69-6 (i.e. ScDMC1:N263Y+A288T) digested with NdeI and PstI resulting in the plasmid pTK72-1. All clones were sequenced to confirm the presence of the mutation.

2. RAD51

ScRAD51 was engineered to encode mutations potentially responsible for ATP-binding and hydrolysis with mutation ScRAD51:G190D. Site-directed mutatgenesis was performed as above with the exception that pMW35 was used as template and the oligonucleotides were yRAD51-G190D-sense and yRAD51-G190D-antisense resulting in the plasmid pTK84. The clone was sequenced to confirm the presence of the mutation.

3. SPO11

ScSPO11 was engineered to encode mutations potentially responsible for topoisomerase-like DNA cleavage activity with mutation ScSPO11:Y135F. Site-directed mutatgenesis was performed as above with the exception that pTK81 was used as template and the oligonucleotides were ySPO-Y135F-sense and ySPO-Y135F-antisense resulting in the plasmid pTK83-3. The clone was sequenced to confirm the presence of the mutation.

4. MRE11

AtMRE11 was engineered to encode mutations responsible for nuclease activity with mutation AtMRE11: Motif I:D-A. This was done using PCR and an oligonucleotide that incorporates a base change into the gene resulting in the desired changed amino acid sequence. The insert of pNH2 corresponding to AtMRE11 was first isolated by digesting the plasmid with EcoRI and purifying the ~2.2 kb fragment corresponding to AtMRE11 bp agarose gel electrophoresis. This was ligated to pBluescript KS+ previously digested with EcoRI. The resultant clone of AtMRE11 was denoted pFO1. A primary PCR reaction was performed with ~30 ng of pFO1 as template DNA, 50 pmol MRE-F1 oligo and 50 pmol OL 12413 oligo, 0.2 mM dNTP's, 2.5 U PfuTurbo (Stratagene) and PfuTurbo buffer constituents recommended by the manufacturer in a volume of 50 μl. The PCR conditions were 3 min @ 94 C, followed by 25 cycles of 30 s @ 94 C, 1 min @ 52 C and 1 min @ 72 C, followed by 3 min @ 72 C and storage at 4 C or −20 C. A secondary PCR reaction was then performed using a 10 μl aliquot of the primary reaction as template and other conditions identical to above except that 25 pmol each of MRE-F2 oligo and OL 12415 oligo were used, and that the extension step was 45 s @ 72 C. A tertiary PCR reaction was then performed with a 5 μl aliquot of the secondary reaction as template and all other conditions identical to the secondary reaction except that the annealing step was 30 s @ 58 C. A quaternary PCR reaction was then performed using a 5 μl aliquot of the tertiary reaction as template and all other conditions identical to the tertiary reaction. The amplified DNA was digested with PstI and XbaI and a ~250 bp fragment corresponding to the 5' portion of AtMRE11 was gel-purified. The middle region of AtMRE11 was isolated by digestion of pFO1 with XbaI and AvaII, and a 1.3 kb fragment was gel-purified. The 3' end of AtMRE11 was amplified by PCR using 25 ng of pFO1 as template DNA, 50 pmol MRE-AVA oligo and 50 pmol MRE-R1 oligo, 0.2 mM dNTP's, 2.5 U cloned Pfu (Stratagene) and cloned Pfu buffer constituents recommended by the manufacturer in a volume of 50 μl. The PCR conditions were 3 min @ 94 C, followed by 10 cycles of 30 s @ 94 C, 30 s @ 52 C and 2 min @ 72 C, followed by 20 cycles of 30 s @ 94 C, 30 s @ 58 C and 2 min @ 72 C, followed by 2 min @ 72 C and storage at 4 C or −20 C. The amplified DNA was digested with AvaII and SalI, and a 650 bp DNA fragment was gel-purified. The plasmid cloning vector pBluescript KS+(Stratagene) was digested with PstI and SalI, and also gel-purified. To resynthesize a gene representing an open reading frame encoding AtMRE11: Motif I:D-A, the fragments prepared above were combined and ligated together, transformed into *E. coli*, and putative clones of the gene were identified as described above. The DNA sequence of the resulting clone, pFO12, was determined to confirm it encodes AtMRE11: Motif I:D-A, with the desired altered basepair mutation in the 5' region of AtMRE11, and that 5' and 3' ends amplified by PCR had the correct sequence of AtMRE11.

C. Genetic Assay

To demonstrate alternative mechanisms for increasing and decreasing meiotic homologous recombination, a genetic assay was employed to examine the effects of different proteins on meiotic homologous recombination and non-sister chromatid exchange. A diploid strain of *S. cerevisiae*, BR2495 [27] was used which possesses heteroalleles at genes essential for biosynthesis of different metabolites required for cell growth and/or division or viability. The allele for a particular gene carried on the maternal chromosome has a mutation and encodes a non-functional protein. The allele for the same gene on the paternal chromosome also has a mutation making its gene product non-functional. However, the mutation of the paternal allele is at a different position in the gene than the mutation in the maternal allele. Because both maternal and paternal alleles are both mutated, the diploid cell cannot make a functional gene product. After meiosis, gametes and progeny that inherit only the maternal or paternal allele also cannot make a functional gene product. However, if a recombination event occurs whereby genetic information is exchanged between maternal and paternal chromosomes within the DNA region between the mutations carried by the two alleles, then a functional allele can result. Progeny carrying this recombined allele resulting from exchange between non-sister chromatids may therefore encode a functional gene product. Thus we have a genetic assay to monitor exchange of genetic information between non-sister chromatids from homologous maternal and paternal chromosomes. The system used here employed *S. cerevisiae* BR2495 strain [27] with genotype as follows: Matα leu2-27 his4-280/Matα (Mat alpha) leu2-3,112 his4-260; ura3-1/ura3-1; trp1-289/trp1-1; CYH10/cyh10; arg4-8 thr1-1/ARG4 thr1-4; ade2-1/ade2-1. BR2495 has heteroalleles to conveniently assay for non-sister chromatid exchange at four loci:

i.) his4 which when functional encodes histidinol dehydrogenase which participates in biosynthesis of histidine enabling cells to grow in absence of external histidine;

ii.) leu2 which when functional encodes 3-isopropylmalate dehydrogenase which participates in biosynthesis of leucine enabling cells to grow in absence of external leucine;

iii.) trp1 which when functional encodes phosphoribosylanthranilate isomerase which participates in biosynthesis of tryptophan enabling cells to grow in absence of external tryptophan;

iv.) thr1 which when functional encodes homoserine kinase which participates in biosynthesis of threonine enabling cells to grow in absence of external threonine.

The strain or progeny carrying defective alleles are termed auxotrophic for histidine, leucine, tryptophan and threonine because they are unable to grow in the absence of these compounds being provided externally for them. Recombinants resulting in genetic exchange between non-sister chromatids of homologous maternal and paternal chromosomes leading to functional alleles are termed prototrophs because they can make their own histidine, leucine, tryptophan and threonine and do not require an external source of these compounds for growth and cell division.

The exemplified assay system involves growth of a BR2495 strain expressing the test gene of interest. The strain is induced to undergo meiosis. Progeny are assayed for viability and the ability to grow in the absence of histidine, leucine, tryptophan or threonine. By determining the number of prototrophic and viable progeny in a given treatment, recombination frequency can be determined (i.e. # prototrophic progeny per # viable progeny). By comparing recombination frequency between different test genes, the effect of the test gene being expressed on either increasing or decreasing meiotic homologous recombination can be determined.

D. Gene Expression

To test the effect of different genes in strategies to modulate meiotic homologous recombination frequency a gene expression system and plasmid vectors functional in *S. cerevisiae* were employed. The exemplified expression system used was based on the plasmids described by Gari et al. (1997). Briefly, a series of *S. cerevisiae* expression vectors were created with variation in vector copy-number per cell and variations in strength of transcription promoter. Therefore, by using different vectors combining different cell copy-number with different promoter strengths, the effect of expressing genes at different levels can be evaluated. The plasmids are based on pCM188 and pCM189 with copy-number of 1-2 plasmids per cell and pCM190 with copy-number of upto 40 plasmids per cell [131]. The transcription promoters on these plasmids is a hybrid system developed by Gari et al. (1997) which permits suppression or induction of gene expression by varying growth medium constituents. The promoter system employs a DNA-binding protein, tetR, fused to a transcription activator derived from the VP16 protein [132]. tetR us a natural component of the regulatory system controlling expression of tetracycline resistance in prokaryotes [132]. In the absence of tetracycline, tetR is bound to a defined DNA sequence, tetO, and prevents expression of tetracycline resistance genes. In the presence of tetracycline, tetR binds tetracycline resulting in a conformational change that causes it to release tetO and thereby permitting expression of tetracycline resistance. By fusing tetR with VP16 and incorporating tetO sites with basal transcription promoter sequences, Gari et al. (1997) created a regulatable transcription promoter system. In the presence of tetracycline or doxycycline, an analogue of tetracycline, transcription of the target gene is suppressed because the tetR-VP16 fusion cannot bind to the promoter to initiate transcription. Conversely, when tetracycline or doxycycline is absent the tetR-VP16 fusion protein can bind to tetO, recruit RNA polymerase and facilitate transcription of the target gene. By varying the number of tetO sites from two (pCM188) to seven (pCM189 and pCM190) the promoter strength can be increased ~2-fold [132]. The combination of vector copy number and promoter strength allows target gene expression to be varied ~5-fold (pCM188 versus pCM190).

The exemplified regulatable expression system discloses strategies to affect meiotic homologous recombination frequency by enabling the promotion of gene expression in cells preparing for and undergoing meiosis. By promoting transcription in cells specifically at this stage one suppresses the effects or any artifactual results due to constitutive expression of test genes during all stages of vegetative growth leading to meiosis. Alternatively, a promoter could be used which is expressed during meiosis or is meiosis-specific.

In summary, the exemplified system involves cloning genes of interest into pCM188 or pCM190. The cells are cultured in the presence of doxycycline to suppress expression of test genes during vegetative growth. The cells are prepared to undergo meiosis and the doxycyline is removed to enable expression of the test gene. The cells are induced to undergo meiosis and resulting progeny cells are tested for viability and frequency of prototrophy resulting from recombination between heteroalleles on non-sister chromatids. The frequency of meiotic homologous recombination can thus be determined for each test gene enabling evaluation and comparison of strategies to modify meiotic homologous recombination.

2. Single Gene Expression Constructs a) AtDMC1

To show the effect of heterologous expression of DMC1 genes on meiotic homologous recombination frequency, AtDMC1 was cloned and expressed in *S. cerevisiae* cells undergoing meiosis. AtDMC1 was cloned into the expression vectors pCM188, pCM189 and pCM190. All three vectors were digested with PmeI and the free ends were dephosphorylated using calf-intestinal phosphatase (New England BioLabs) following the protocol supplied by the manufacturer. pKR225 was digested with SmaI and XhoI and treated with the Klenow fragment of DNA polymerase (Gibco/BRL) following standard procedures [123]. The DNA fragment released from pKR225 corresponding to AtDMC1 (~1.1 kb) was purified by agarose gel electrophoresis and recovered from the agarose as described above. The AtDMC1 fragment was then ligated to the prepared vector fragments, transformed into *E. coli* and putative clones identified as described above. The resultant clones of AtDMC1 in pCM188, pCM189 and pCM190 were denoted pTK45, pTK5 and pTK6, respectively.

b) ScDMC1

To show the effect of increased expression of native DMC1 on meiotic homologous recombination frequency, ScDMC1 was cloned and expressed in *S. cerevisiae* cells undergoing meiosis. ScDMC1 was cloned into pCM190 by first digesting this vector with PmeI and PstI. pMW13 was digested with XbaI and treated with T4 DNA polymerase following standard procedures [123] before subsequent digestion with PstI. DNA fragments of interest corresponding to ScDMC1 (~1.1 kb) and pCM190 (~8 kb) were purified by agarose gel electrophoresis and recovered from the agarose as described above. The fragments were ligated together, transformed into *E. coli* and putative clones of the gene in the expression vector were identified. The resultant clone of ScDMC1 in pCM190 was denoted pTK58.

To show the effect of expression of mutant DMC1 on meiotic homologous recombination frequency, yDMC1:G126D was cloned and expressed in *S. cerevisiae* cells undergoing meiosis. yDMC1:G126D was cloned into pTK77, a derivative of pCM190 containing the additional restriction sites SmaI, EcoRV, FseI and SwaI, in 5'-3' order, located adjacent to but 5' of the unique HindIII site of pCM190 and 3' of the CYC1 terminator of the vector. The pTK77 vector was digested with PmeI and PstI. pTK68-3 was digested with XbaI and treated with Klenow polymerase following standard procedures [123] before subsequent digestion with PstI. DNA fragments of interest corresponding to yDMC1:G126D (~1.1 kb) and pTK77 (~8 kb) were purified by agarose gel electrophoresis and recovered from the agarose as described above.

The fragments were ligated together, transformed into *E. coli* and putative clones of the gene in the expression vector were identified. The resultant clone of yDMC1:G126D in the pCM190 derived pTK77 was denoted pTK85.

c) ScRAD51

To show the effect of increased expression of native RAD51 on meiotic homologous recombination frequency, ScRAD51 was cloned and expressed in *S. cerevisiae* cells undergoing meiosis. ScRAD51 was cloned into pCM190 by first digesting this vector with BamHI and PstI. pMW35 was also digested with BamHI and PstI. DNA fragments of interest corresponding to ScRAD51 (~1.2 kb) and pCM190 (~8 kb) were purified by agarose gel electrophoresis and recovered from the agarose as described above. The fragments were ligated together, transformed into *E. coli* and putative clones of the gene in the expression vector were identified. The resultant clone of ScRAD51 in pCM190 was denoted pTK53.

To show the effect of expression of mutant RAD51 on meiotic homologous recombination frequency, yRAD51:G190D was cloned and expressed in *S. cerevisiae* cells undergoing meiosis. yRAD51:G190D was cloned into pCM190 by first digesting this vector with BamHI and PstI. pTK84 was also digested with BamHI and PstI. DNA fragments of interest corresponding to yRAD51:G190D (~1.2 kb) and pCM190 (~8 kb) were purified by agarose gel electrophoresis and recovered from the agarose as described above. The fragments were ligated together, transformed into *E. coli* and putative clones of the gene in the expression vector were identified. The resultant clone of yRAD51:G190D in pCM190 was denoted pTK95.

d) EcSSB

To show the effect of increased ssDNA-binding protein on meiotic homologous recombination frequency, SSB and NLS-SSB were cloned and expressed in *S. cerevisiae* cells undergoing meiosis. SSB and NLS-SSB were cloned individually into pCM190 [132] by first digesting this vector with BamHI and PstI. pTK27 (SSB) and pTK29 (NLS-SSB) were also digested with BamHI and PstI. DNA fragments of interest corresponding to SSB or NLS-SSB (~0.6 kb) and pCM190 (~8 kb) were purified by agarose gel electrophoresis and recovered from the agarose as described above. The SSB and NLS-SSB DNA fragments were ligated independently to the DNA fragment corresponding to pCM190, transformed into *E. coli* and putative clones of the genes in the expression vector were identified. The resultant clones of SSB and NLS-SSB in pCM190 were denoted pTK35 and pTK36, respectively.

e) ScSPO11

To show the effect of increased expression of native SPO11 on meiotic homologous recombination frequency, ScSPO11 was cloned and expressed in *S. cerevisiae* cells undergoing meiosis. ScSPO11 was cloned into pCM190 by first digesting this vector with BamHI and PstI. pTK81 was also digested with BamHI and PstI. DNA fragments of interest corresponding to ScSPO11 (~1.2 kb) and pCM190 (~8 kb) were purified by agarose gel electrophoresis and recovered from the agarose as described above. The fragments were ligated together, transformed into *E. coli* and putative clones of the gene in the expression vector were identified. The resultant clone of ScSPO11 in pCM190 was denoted pTK89.

To show the effect of expression of mutant SPO11 on meiotic homologous recombination frequency ySPO11:Y135F was cloned and expressed in *S. cerevisiae* cells undergoing meiosis. ySPO11:Y135F was cloned into pCM190 by first digesting this vector with BamHI and PstI. pTK83-3 was also digested with BamHI and PstI. DNA fragments of interest corresponding to ySPO11:Y135F (~1.2 kb) and pCM190 (~8 kb) were purified by agarose gel electrophoresis and recovered from the agarose as described above. The fragments were ligated together, transformed into *E. coli* and putative clones of the gene in the expression vector were identified. The resultant clone of ySPO11:Y135F in pCM190 was denoted pTK94.

E. Biological Assay

To demonstrate the effect of different genes on meiotic homologous recombination frequency, plasmids containing the candidate genes were first created, as described above, and then introduced into *S. cerevisiae* BR2495 to create different strains. These strains were then grown, induced to undergo meiosis and the resultant progeny scored for phenotypic markers to determine meiotic homologous recombination frequency. Comparison of the homologous recombination frequency in the various strains to control strains containing only the corresponding parental vector containing no test gene enabled assessment of the genetic and biological effects of the test genes.

Expression vectors containing the test genes were introduced into *S. cerevisiae* BR2495 cells following the method of Geitz et al. [133]. Exemplified genes and the corresponding expression plasmids are outlined in TABLE 2. Cell lines carrying these plasmid constructs were selected for by culturing cells in minimal medium lacking uracil (i.e. SC-URA; [134]): BR2495 is homozygous for the defective ura3-1 allele [27] and therefore cannot synthesize this essential metabolite; expression plasmids based on pCM188, pCM189 and pCM190 have a functional URA3 gene and therefore BR2495 cells possessing such plasmids will be able to synthesize uracil and be able to grow on medium lacking uracil. Cells were cultured in the presence of doxycycline (10 μg/ml for solid media; 5 μg/ml for liquid media) to suppress expression of test genes until desired growth stages.

To assay meiotic homologous recombination frequency, single colonies from each test strain were used to first inoculate 3 ml of SC-URA+DOX (i.e. SC-URA containing doxycycline at 5 μg/ml) in a 15 ml tube (Falcon) which was then incubated at 30 C with shaking (200 RPM) for ~1.5 d. Ten cultures were prepared for each test strain, including BR2495 possessing the parental expression vector without a test gene and BR2495 possessing the various expression plasmids containing the test genes. Cells from 1 ml of culture were pelleted by centrifugation at 9000 RPM for 2 min in a standard microcentrifuge (Brinkman) and resuspended in 1 ml of sterile-distilled water (SDW). The cells were used to inoculate 5 ml of SC-A pre-meiosis medium (per litre: 1.7 g yeast nitrogen free base (Difco), 5 g ammonium acetate (Sigma), 20 g potassium acetate (Sigma), 2 g amino acid drop out mix [134]; and in some experiments doxycycline at 5 μg/ml) in a 50 ml tube (Falcon) at a 1:50 dilution. The cultures were then incubated at 30 C with shaking (225 RPM) for 2 d. Aliquots of cells from each culture were then collected to assay for mitotic homologous recombination frequency occurring during vegetative growth. Dilutions of these cells were plated on YPD medium (per litre: 10 g Bacto-yeast extract, 20 g Bacto-peptone, 20 g glucose, 20 g Bacto-agar; [134]) to determine viable cell number, and plated on minimal media lacking particular amino acids so as to examine homologous recombination at different test genomic loci in BR2495 (i.e. SC minus histidine (SC-his), leucine (SC-leu), threonine (SC-thr), or tryptophan (SC-trp) [134]). These plates were incubated at 30 C for 2-4 d and then colonies were counted. The remaining cells in each culture in pre-meiosis medium were pelleted by centrifugation at 4000 RPM for 10 min at 4 C. For cultures containing doxycyline in the pre-meiosis medium, the pellet was resuspended in 5 ml of SC-A pre-meiosis medium and incubated at room temperature for 3 h. These cells, and those cells incubated in pre-meiosis medium without doxycycline, were then pelleted by centrifugation at 4000 RPM for 10 min at 4 C and resuspended in 4 ml SPM meiosis-induction medium (0.3% (w/v) potassium acetate, 0.02% (w/v) raffinose, 5 µg/ml histidine, 25 µg/ml leucine, 5 µg/ml tryptophan, 50 µg/ml threonine, 5 µg/ml adenine). The cells were again pelleted by centrifugation at 4000 RPM for 10 min at 4 C and resuspended in 3.5 ml SPM meiosis-induction medium. Cultures were then incubated at 30 C with shaking (225 RPM) for 2 d to enable cells to undergo meiosis. Dilutions of the cells were made using SDW and cells were then plated on YPD to determine viable cell number, and on minimal media lacking particular amino acids so as to examine meiotic homologous recombination at different test genomic loci in BR2495, as described above. Duplicate dilutions and plating of each culture were performed. Plates were incubated at 30 C for 2-4 d and then colonies were counted. Frequency of recombinants for each culture was determined by dividing the number of prototrophs conferred by restoration of function for a particular test locus heteroallele by the viable cell number, taking into consideration the dilution factors. Meiotic homologous recombination frequency for each culture was corrected when necessary for background recombinants resulting during vegetative growth by subtraction of the mitotic homologous recombination frequency determined prior to placing the cells in SPM meiosis-induction medium. Mean values for the 10 replicates of each test strain were determined using the corrected values. Inclusion of the values from all 10 replicates in determining the mean was evaluated by the Q-test [135] and values from individual replicates were excluded from the final mean if the statistic indicated a significant deviation from the values of other replicates. Comparison of means of meiotic homologous recombination frequency from test genes to that from control strains was done to determine the effect of the test gene. Statistical significance of the differences between these values was confirmed by evaluation using the t-test [136].

Results

As shown in TABLE 2, results from the exemplified embodiments demonstrate modification of meiotic homologous recombination frequency and non-sister chromatid exchange (increases and decreases) through modifying the expression and activity of components of the DNA recombination process. The genetic evidence shows that non-sister chromatid exchange during meiosis is modified by the exemplified embodiments.

1. Reduced Meiotic Homologous Recombination Frequency

Meiotic homologous recombination may for example be reduced by a dominant-negative effect conferred by heterologous expression of a protein or expression of a mutant form of a native protein. This reduction occurs at different genomic loci both on the same and different chromosomes. In the exemplified embodiments, heterologous expression of AtDMC1 in *S. cerevisiae* results in up to a 34% reduction in meiotic homologous recombination. The suppression is found at three different genetic loci, his4 and leu2, located on chromosome III, and trp1, located on chromosome IV. The level of suppression of meiotic homologous recombination may also be regulatable by controlling the level of expression of the inhibitory factor, as demonstrated by the estimated 3-fold difference in expression between pTK5 and pTK6 resulting in ~20% difference in inhibiting meiotic homologous recombination frequency. ScDMC1 expressed in plants or animals may also be used to decrease meiotic homologous recombination or an animal protein may be used to decrease meiotic homologous recombination in plants, or an animal protein may be used to decrease meiotic homologous recombination in an evolutionarily distant animal species. These results also demonstrate the efficacy of a dominant-negative effect to reduce meiotic homologous recombination frequency. In alternative embodiments, this may also be achieved by expressing an altered form of a native protein. In the exemplified embodiments, expression of a mutant form of ScDMC1 results in up to a 24% reduction in meiotic homologous recombination frequency; expression of a mutant form of ScRAD51 results in up to a 44% reduction in meiotic homologous recombination frequency; and expression of a mutant form of ScSPO11 results in up to a 48% reduction in meiotic homologous recombination frequency. The suppression is found at different genetic loci and on different chromosomes demonstrating the effect is general to the whole genome. The results demonstrate how affecting the activity level of proteins involved in meiotic homologous recombination can be used to reduce homologous recombination frequency. These results also demonstrate the efficacy of using a dominant-negative effect to reduce meiotic homologous recombination frequency. Mutant forms of proteins involved in meiotic recombination and non-sister chromatid exchange may also be used in plant and animal species to modulate meiotic homologous recombination frequency.

2. Increased Meiotic Homologous Recombination Frequency

In the exemplified embodiments, meiotic homologous recombination frequency occurs at different genomic loci both on the same and different chromosomes. Increased expression of either ScDMC1 or ScRAD51 or ScSPO11 is shown to increase meiotic homologous recombination frequency by up to ~5-fold, ~3-fold, or ~2-fold, respectively. The increase is shown at three different genetic loci, his4 and leu2, located on chromosome III, and trp1, located on chromosome IV demonstrating the effect is general to the whole genome. Increased expression or activity level of proteins involved in meiotic recombination and non-sister chromatid exchange may also be used in plant and animal species to modulate meiotic homologous recombination frequency.

In alternative exemplified embodiments, expression of prokaryotic proteins is shown to increase or decrease homologous meiotic recombination. Heterologous expression of a ssDNA-binding protein, SSB, is shown to decrease or increase homologous recombination frequency depending upon the genomic locus. A dominant-negative effect results at some loci to suppress homologous recombination, as shown at the leu2 locus where a reduction of homologous recombination frequency by ~40% was shown. In contrast, a stimulation of homologous recombination occurs at some loci, as shown by the his4 locus where homologous recombination frequency was enhanced by 13%. In both cases, the action of SSB in eukaryotes was promoted ~10% by addition of a nuclear localization sequence to the protein (i.e. NLS-SSB). In alternative embodiments, modifying the function or expression of endogenous native ssDNA-binding proteins may also be used to modify meiotic homologous recombination frequency.

TABLE 1

Oligonucleotides for amplifying and modifying target genes

| Oligo name | Target Gene | Sequence (5'-3') |
| --- | --- | --- |
| OL11434 | AtDMC1 | CATATGATGGCTTCTCTTAAGGCTG (SEQ ID NO: 2) |
| OL11433 | AtDMC1 | GACATATAAAAGAGTTCGCTCC (SEQ ID NO: 3) |
| OL11435 | AtDMC1 | AAACTCGAGCTAATCCTTCGCGTCAGCAATG (SEQ ID NO: 4) |
| AtSPO-5'Sma | AtSPO11 | GGGTATGGAGGGAAAATTCGCTAG (SEQ ID NO: 5) |
| AtSPO-3'X | AtSPO11 | CCTTGAGTTGGAGACTAGTTATC (SEQ ID NO: 6) |
| AtSPO-3'PstNot | AtSPO11 | ATCCTGCAGGCGGCCGCTCATCAAGGAGAGCTTACTTCACG (SEQ ID NO: 7) |
| AtRAD51-5'Bam | AtRAD51 | GGGGGATCCAAAAAAATGACGACGATGGAGCAGCG (SEQ ID NO: 8) |
| AtRAD51-3'X | AtRAD51 | GAAGCAAGGCATTGTTGTGG (SEQ ID NO: 9) |
| AtRAD51-3'Pst | AtRAD51 | AACTGCAGTTATCAATCCTTGCAATCTGTTACAC (SEQ ID NO: 10) |
| OL12414 | AtMRE11 | CGGAATTCATGATTGTAAAACTTGACAGGG (SEQ ID NO: 11) |
| OL12413 | AtMRE11 | GGTCGCTGACTACTTGAAAC (SEQ ID NO: 12) |
| OL12415 | AtMRE11 | TCATTCAGACAGTGGCGACG (SEQ ID NO: 13) |
| OL12779 | AtMRE11 | GGCCTGAAGTTCAAGAAG (SEQ ID NO: 14) |
| OL12780 | AtMRE11 | GCTCGACTTCTTCGCTTG (SEQ ID NO: 15) |
| MRE-F1 | AtMRE11 | GCGCTGCAGCATATGCCCGGGGAATTCATGTCTAGGGAGGATTTTAGTGATACACTT (SEQ ID NO: 16) |
| MRE-F2 | AtMRE11 | GCGCTGCAGCATATGCCCGGGGAATTCATGTCTAGGGAGGATTTTAGTGATACACTTCGAGTACTTGTTGCAACTGCTTGCCACTTGGGCTAC (SEQ ID NO: 17) |
| MRE-R1 | AtMRE11 | CGCGTCGACCCCGGGTTAAGGCGCGCCTCTTCTTAGAGCTCCATAG (SEQ ID NO: 18) |
| MRE-AVA | AtMRE11 | GATAGGTCCACTCGACCCACTGG (SEQ ID NO: 19) |
| YDMC-5'Bam | ScDMC1 | GGGGGATCCAAAAAAATGTCTGTTACAGGAACTGAG (SEQ ID NO: 20) |
| YDMC-3'Pst | ScDMC1 | AACTGCAGCTACTAGTCACTTGAATCGGTAATACC (SEQ ID NO: 21) |
| YDMC-G126D-sense | ScDMC1 | GGTGAATTTAGGTGTGATAAGACACAGATGTCTC (SEQ ID NO: 22) |
| YDMC-G126D-antisense | ScDMC1 | GAGACATCTGTGTCTTATCACACCTAAATTCACC (SEQ ID NO: 23) |
| YDMC-N263Y-sense | ScDMC1 | GCAGTATTTCTGACATACCAAGTTCAATCAGAC (SEQ ID NO: 24) |
| YDMC-N263Y-antisense | ScDMC1 | GTCTGATTGAACTTGGTATGTCAGAAATACTGC (SEQ ID NO: 25) |
| YDMC-A288T-sense | ScDMC1 | GAGGGCACGTTCTGACACATGCGTCAGC (SEQ ID NO: 26) |
| YDMC-A288T-antisense | ScDMC1 | GCTGACGCATGTGTCAGAACGTGCCCTC (SEQ ID NO: 27) |
| YR51-5'Bam | ScRAD51 | GGGGGATCCAAAAAAATGTCTCAAGTTCAAGAACAAC (SEQ ID NO: 28) |
| YR51-3'Pst | ScRAD51 | AACTGCAGTTACTACTCGTCTTCTTCTCTGGGG (SEQ ID NO: 29) |

TABLE 1-continued

Oligonucleotides for amplifying and modifying target genes

| Oligo name | Target Gene | Sequence (5'-3') |
|---|---|---|
| YRAD51-G190D-sense | ScRAD51 | CGGTGAATTCAGGACAGATAAGTCCCAGCTATGTC (SEQ ID NO: 30) |
| YR52-5'Pme | ScRAD52 | AAAGAATTCGTTTAAACATGGCGTTTTTAAGCTATTTTG (SEQ ID NO: 31) |
| YR52-3'Not | ScRAD52 | ATCGCGGCCGCTCATCAAGTAGGCTTGCGTGCA (SEQ ID NO: 32) |
| YR54-5'RI | ScRAD54 | GGGGAATTCAAAAAAATGGCAAGACGCAGATTAC (SEQ ID NO: 33) |
| YR54-3'Pst | ScRAD54 | AAACTGCAGTCATCAATGTGAAATATATTGAAATGC (SEQ ID NO: 34) |
| YSPO-5'Bam | ScSPO11 | ATCGGATCCAAAAAAATGGCTTTGGAGGGATTG (SEQ ID NO: 35) |
| Yspo-3'Pst | ScSPO11 | GGGCTGCAGTCATCATTTGTATTCAAAAATTCTGG (SEQ ID NO: 36) |
| YSPO-Y135F-sense | ScSPO11 | GTGAGAGATATCTTCTTCTCCAACGTGGAATTG (SEQ ID NO: 37) |
| YSPO-Y135F-antisense | ScSPO11 | CAATTCCACGTTGGAGAAGAAGATATCTCTCAC (SEQ ID NO: 38) |

TABLE 2

| | | Expression Plasmid | | | | His4 | | | Leu2 | |
|---|---|---|---|---|---|---|---|---|---|---|
| Gene | Experiment | Plasmid Construct | Vector | Promoter[b] | Copy Number[c] | Prototroph Frequency | Ratio of HR[e] | Mean Ratio of HR | Prototroph Frequency | Ratio of HR |
| AtDMC1 | 1 | control[a] | pCM188 | Weak | Low | $6.26 \times 10^{-3}$ | 0.68 | $0.70 \pm 0.02$ | | |
| | | pTK45 | pCM188 | Weak | Low | $4.23 \times 10^{-3}$ | | | | |
| | 2 | control | pCM188 | Weak | Low | $5.57 \times 10^{-3}$ | 0.72 | | | |
| | | pTK45 | pCM188 | Weak | Low | $4.01 \times 10^{-3}$ | | | | |
| | 1 | control | pCM189 | Strong | Low | $5.86 \times 10^{-3}$ | 0.62 | $0.73 \pm 0.11$ | $1.44 \times 10^{-4}$ | 0.76 |
| | | pTK5 | pCM189 | Strong | Low | $3.61 \times 10^{-3}$ | | | $1.09 \times 10^{-4}$ | |
| | 2 | control | pCM189 | Strong | Low | $3.95 \times 10^{-3}$ | 0.83 | | $1.20 \times 10^{-4}$ | 0.91 |
| | | pTK5 | pCM189 | Strong | Low | $3.29 \times 10^{-3}$ | | | $1.09 \times 10^{-4}$ | |
| | 1 | control | pCM190 | Strong | High | $1.30 \times 10^{-2}$ | 0.82 | $0.73 \pm 0.13$ | $3.60 \times 10^{-4}$ | 0.61 |
| | | pTK6 | pCM190 | Strong | High | $1.06 \times 10^{-2}$ | | | $2.20 \times 10^{-4}$ | |
| | 2 | control | pCM190 | Strong | High | $1.47 \times 10^{-2}$ | 0.63 | | $2.30 \times 10^{-4}$ | 0.70 |
| | | pTK6 | pCM190 | Strong | High | $9.28 \times 10^{-3}$ | | | $1.60 \times 10^{-4}$ | |
| ScDMC1 | 1 | control | pCM190 | Strong | High | $1.81 \times 10^{-3}$ | 2.59 | 2.59 | $5.25 \times 10^{-5}$ | 2.26 |
| | | pTK58 | pCM190 | Strong | High | $4.70 \times 10^{-3}$ | | | $1.19 \times 10^{-4}$ | |
| | 2 | control | pCM190 | Strong | High | | | | $2.69 \times 10^{-5}$ | 8.22 |
| | | pTK58 | pCM190 | Strong | High | | | | $2.21 \times 10^{-4}$ | |
| ScRAD51 | 1 | control | pCM190 | Strong | High | $1.81 \times 10^{-3}$ | 1.87 | 1.87 | $2.69 \times 10^{-5}$ | 2.07 |
| | | pTK53 | pCM190 | Strong | High | $3.39 \times 10^{-3}$ | | | $5.58 \times 10^{-5}$ | |
| SSB | 1 | control | pCM190 | Strong | High | $6.96 \times 10^{-3}$ | 1.13 | 1.13 | $1.58 \times 10^{-4}$ | 0.61 |
| | | pTK35 | pCM190 | Strong | High | $7.89 \times 10^{-3}$ | | | $9.58 \times 10^{-5}$ | |
| NLS-SSB | 1 | control | pCM190 | Strong | High | $6.96 \times 10^{-3}$ | 1.29 | 1.29 | $1.58 \times 10^{-4}$ | 0.54 |
| | | pTK36 | pCM190 | Strong | High | $9.00 \times 10^{-3}$ | | | $8.61 \times 10^{-5}$ | |
| yDMC1: G126D | 1 | control | pCM190 | Strong | High | $8.81 \times 10^{-3}$ | 0.76 | 0.76 | $1.69 \times 10^{-4}$ | 0.91 |
| | | pTK85 | pCM190 | Strong | High | $6.72 \times 10^{-3}$ | | | $1.53 \times 10^{-4}$ | |
| yRAD51: G190D | 1 | control | pCM190 | Strong | High | $8.81 \times 10^{-3}$ | 0.39 | $0.56 \pm 0.17$ | $1.69 \times 10^{-4}$ | 0.39 |
| | | pTK95 | pCM190 | Strong | High | $3.43 \times 10^{-3}$ | | | $6.58 \times 10^{-5}$ | |
| | 2 | control | pCM190 | Strong | High | $5.21 \times 10^{-3}$ | 0.73 | | $1.23 \times 10^{-4}$ | 0.78 |
| | | pTK95 | pCM190 | Strong | High | $3.82 \times 10^{-3}$ | | | $9.58 \times 10^{-5}$ | |
| ScSPO11 | 1 | control | pCM190 | Strong | High | $4.37 \times 10^{-3}$ | 1.80 | 1.80 | $6.14 \times 10^{-5}$ | 1.87 |
| | | pTK89 | pCM190 | Strong | High | $7.87 \times 10^{-3}$ | | | $1.15 \times 10^{-4}$ | |
| ySPO11: Y135F | 1 | control | pCM190 | Strong | High | $6.93 \times 10^{-3}$ | 0.65 | 0.65 | $1.23 \times 10^{-4}$ | 0.52 |
| | | pTK94 | pCM190 | Strong | High | $4.53 \times 10^{-3}$ | | | $6.41 \times 10^{-5}$ | |

TABLE 2-continued

| Gene | Experiment | Expression Plasmid | | | | Leu2 | Trp1 | | |
| | | Plasmid Construct | Vector | Promoter[b] | Copy Number[c] | Mean Ratio of HR | Prototroph Frequency | Ratio of HR | Mean Ratio of HR |
|---|---|---|---|---|---|---|---|---|---|
| AtDMC1 | 1 | control[a] | pCM188 | Weak | Low | | | | |
| | | pTK45 | pCM188 | Weak | Low | | | | |
| | 2 | control | pCM188 | Weak | Low | | $5.33 \times 10^{-5}$ | 0.84 | 0.84 |
| | | pTK45 | pCM188 | Weak | Low | | $4.49 \times 10^{-5}$ | | |
| | 1 | control | pCM189 | Strong | Low | $0.84 \pm 0.08$ | | | |
| | | pTK5 | pCM189 | Strong | Low | | | | |
| | 2 | control | pCM189 | Strong | Low | | | | |
| | | pTK5 | pCM189 | Strong | Low | | | | |
| | 1 | control | pCM190 | Strong | High | $0.66 \pm 0.05$ | | | |
| | | pTK6 | pCM190 | Strong | High | | | | |
| | 2 | control | pCM190 | Strong | High | | | | |
| | | pTK6 | pCM190 | Strong | High | | | | |
| ScDMC1 | 1 | control | pCM190 | Strong | High | $5.24 \pm 2.98$ | $3.64 \times 10^{-5}$ | 1.42 | $1.72 \pm 0.30$ |
| | | pTK58 | pCM190 | Strong | High | | $5.15 \times 10^{-5}$ | | |
| | 2 | control | pCM190 | Strong | High | | $4.14 \times 10^{-5}$ | 2.02 | |
| | | pTK58 | pCM190 | Strong | High | | $8.36 \times 10^{-5}$ | | |
| ScRAD51 | 1 | control | pCM190 | Strong | High | 2.07 | $3.39 \times 10^{-5}$ | 1.83 | 1.83 |
| | | pTK53 | pCM190 | Strong | High | | $6.22 \times 10^{-5}$ | | |
| SSB | 1 | control | pCM190 | Strong | High | 0.61 | | | |
| | | pTK35 | pCM190 | Strong | High | | | | |
| NLS-SSB | 1 | control | pCM190 | Strong | High | 0.54 | | | |
| | | pTK36 | pCM190 | Strong | High | | | | |
| yDMC1: G126D | 1 | control | pCM190 | Strong | High | 0.91 | | | |
| | | pTK85 | pCM190 | Strong | High | | | | |
| yRAD51: G190D | 1 | control | pCM190 | Strong | High | $0.59 \pm 0.20$ | $7.64 \times 10^{-5}$ | 0.38 | $0.66 \pm 0.28$ |
| | | pTK95 | pCM190 | Strong | High | | $2.88 \times 10^{-5}$ | | |
| | 2 | control | pCM190 | Strong | High | | $5.12 \times 10^{-5}$ | 0.94 | |
| | | pTK95 | pCM190 | Strong | High | | $4.83 \times 10^{-5}$ | | |
| ScSPO11 | 1 | control | pCM190 | Strong | High | 1.87 | $4.90 \times 10^{-5}$ | 1.64 | 1.64 |
| | | pTK89 | pCM190 | Strong | High | | $8.04 \times 10^{-5}$ | | |
| ySPO11: Y135F | | control | pCM190 | Strong | High | 0.52 | $5.72 \times 10^{-5}$ | 0.79 | 0.79 |
| | | pTK94 | pCM190 | Strong | High | | $4.49 \times 10^{-5}$ | | |

[a]Control plasmid contained no gene for expression.
[b]Promoter strength was indicated as "weak" for plasmids containing 2 copies of tetO and "strong" for plasmids containing 7 copies of tetO.
[c]Plasmid copy number was "low" with 1-2 copies per cell and "high" for plasmids with upto 40 copies per cell.
[d]Prototroph frequency determined as the number of prototrophs per viable cell number. Value represents the mean from 10 independent cultures.
[e]Meiotic homologous recombination frequency determined by dividing the prototroph frequency of the strain with the test gene with that of the control.

REFERENCES

The following documents, to which reference may be made elsewhere herein by number, are incorporated herein by reference.

1. Hall, R M, Collis, C M: Mobile gene cassettes and integrons: capture and spread of genes by site-specific recombination. Mol. Microbiol. 15: 593-600 (1995).
2. Critchlow, S E, Jackson, S P: DNA end-joining: from yeast to man. Trends Biochem. Sci. 23: 394-398 (1998).
3. Lindahl, T, Wood, R D: Quality control by DNA repair. Science 286: 1897-1905 (1999).
4. Roeder, G S: Meiotic chromosomes: it takes two to tango. Genes Dev. 11: 2600-2621 (1997).
5. Paques, F, Haber, J E: Multiple pathways of recombination induced by double-strand breaks in *Saccharomyces cerevisiae*. Microbiol. Mol. Biol. Rev. 63: 349-404 (1999).
6. Kowalczykowski, S C, Dixon, D A, Eggleston, A K, Lauder, S D, Rehrauer, W M: Biochemistry of homologous recombination in *Escherichia coli*. Microbiol. Rev. 58: 401-465 (1994).
7. Haber, J E: DNA recombination: the replication connection. Trends Biochem. Sci. 24: 271-275 (1999).
8. Strickberger, M W: Genetics. Macmillan Publishing Company, New York (1985).
9. Keeney, S, Giroux, C N, Kleckner, N: Meiosis-specific DNA double-strand breaks are catalysed by Spo11, a member of a widely conserved protein family. Cell 88: 375-384 (1997).
10. Cha, R S, Weiner, B M, Keeney, S, Dekker, J, Kleckner, N: Progression of meiotic DNA replication is modulated by interchromosomal interaction proteins, negatively by Spo11p and positively by Rec8p. Genes Dev. 14: 493-503 (2000).
11. Hartung, F, Puchta, H: Molecular characterisation of two paralogous SPO11 homologues in *Arabidopsis thaliana*. Nucleic Acids Res. 28: 1548-1554 (2000).
12. Johzuka, K, Ogawa, H: Interaction of Mre11 and Rad50: two proteins required for DNA repair and meiosis-specific double-strand break formation in *Saccharomyces cerevisiae*. Genetics 139: 1521-1532 (1995).
13. Rozwadowski, K, Kreiser, T, Hasnadka, R, Lydiate, D. AtMRE11: a component of meiotic recombination and DNA repair in plants. 10th International Conference on *Arabidopsis* Research, Melbourne, Australia, Jul. 4-8, 1999. 1999. Ref Type: Abstract
14. Hartung, F, Puchta, H: Isolation of the complete cDNA of the Mre11 homologue of *Arabidopsis* indicates conservation of DNA recombination mechanisms between plants and other eukaryotes. Plant Physiol. 121: 312 (1999).
15. Petrini, J H, Walsh, M E, DiMare, C, Chen, X N, Korenberg, J R, Weaver, D T: Isolation and characterization of the human MRE11 homologue. Genomics 29: 80-86 (1995).
16. Alani, E, Subbiah, S, Kleckner, N: The yeast RAD50 gene encodes a predicted 153-kD protein containing a purine nucleotide-binding domain and two large heptad-repeat regions. Genetics 122: 47-57 (1989).
17. Dolganov, G M, Maser, R S, Novikov, A, Tosto, L, Chong, S, Bressan, D A, Petrini, J H: Human Rad50 is physically associated with human Mre11: identification of a conserved multiprotein complex implicated in recombinational DNA repair. Mol. Cell Biol. 16: 4832-4841 (1996).
18. Ivanov, E L, Sugawara, N, White, C I, Fabre, F, Haber, J E: Mutations in XRS2 and RAD50 delay but do not prevent mating-type switching in *Saccharomyces cerevisiae*. Mol. Cell Biol. 14: 3414-3425 (1994).
19. Carney, J P, Maser, R S, Olivares, H, Davis, E M, Le Beau, M, Yates, J R, III, Hays, L, Morgan, W F, Petrini, J H: The hMre11/hRad50 protein complex and Nijmegen breakage syndrome: linkage of double-strand break repair to the cellular DNA damage response. Cell 93: 477-486 (1998).
20. Bishop, D K, Park, D, Xu, L, Kleckner, N: DMC1: a meiosis-specific yeast homolog of *E. coli* recA required for recombination, synaptonemal complex formation, and cell cycle progression. Cell 69: 439-456 (1992).
21. Kobayashi, T, Kobayashi, E, Sato, S, Hotta, Y, Miyajima, N, Tanaka, A, Tabata, S: Characterization of cDNAs induced in meiotic prophase in lily microsporocytes. DNA Res. 1: 15-26 (1994).
22. Habu, T, Taki, T, West, A, Nishimune, Y, Morita, T: The mouse and human homologs of DMC1, the yeast meiosis-specific homologous recombination gene, have a common unique form of exon-skipped transcript in meiosis. Nucleic Acids Res. 24: 470-477 (1996).
23. Shinohara, A, Ogawa, H, Ogawa, T: Rad51 protein involved in repair and recombination in *S. cerevisiae* is a RecA-like protein. Cell 69: 457-470 (1992).
24. Doutriaux, M P, Couteau, F, Bergounioux, C, White, C: Isolation and characterisation of the RAD51 and DMC1 homologs from *Arabidopsis thaliana*. Mol. Gen. Genet. 257: 283-291 (1998).
25. Shinohara, A, Ogawa, H, Matsuda, Y, Ushio, N, Ikeo, K, Ogawa, T: Cloning of human, mouse and fission yeast recombination genes homologous to RAD51 and recA. Nat. Genet. 4: 239-243 (1993).
26. Wold, M S: Replication protein A: a heterotrimeric, single-stranded DNA-binding protein required for eukaryotic DNA metabolism. Annu. Rev. Biochem. 66: 61-92 (1997).
27. Ross-Macdonald, P, Roeder, G S: Mutation of a meiosis-specific MutS homolog decreases crossing over but not mismatch correction. Cell 79: 1069-1080 (1994).
28. Paquis-Flucklinger, V, Santucci-Darmanin, S, Paul, R, Saunieres, A, Turc-Carel, C, Desnuelle, C: Cloning and expression analysis of a meiosis-specific MutS homolog: the human MSH4 gene. Genomics 44: 188-194 (1997).
29. Hollingsworth, N M, Ponte, L, Halsey, C: MSH5, a novel MutS homolog, facilitates meiotic reciprocal recombination between homologs in *Saccharomyces cerevisiae* but not mismatch repair. Genes Dev. 9: 1728-1739 (1995).
30. Winand, N J, Panzer, J A, Kolodner, R D: Cloning and characterization of the human and *Caenorhabditis elegans* homologs of the *Saccharomyces cerevisiae* MSH5 gene. Genomics 53: 69-80 (1998).
31. Hunter, N, Borts, R H: Mlh1 is unique among mismatch repair proteins in its ability to promote crossing-over during meiosis. Genes Dev. 11: 1573-1582 (1997).
32. Kolodner, R D, Hall, N R, Lipford, J, Kane, M F, Morrison, P T, Finan, P J, Burn, J, Chapman, P, Earabino, C, Merchant, E: Structure of the human MLH1 locus and analysis of a large hereditary nonpolyposis colorectal carcinoma kindred for mlh1 mutations. Cancer Res. 55: 242-248 (1995).
33. Jean, M, Pelletier, J, Hilpert, M, Belzile, F, Kunze, R: Isolation and characterization of AtMLH1, a MutL homologue from *Arabidopsis thaliana*. Mol. Gen. Genet. 262: 633-642 (1999).
34. Milne, G T, Weaver, D T: Dominant negative alleles of RAD52 reveal a DNA repair/recombination complex including Rad51 and Rad52. Genes Dev. 7: 1755-1765 (1993).
35. Muris, D F, Bezzubova, O, Buerstedde, J M, Vreeken, K, Balajee, A S, Osgood, C J, Troelstra, C, Hoeijmakers, J H, Ostermann, K, Schmidt, H: Cloning of human and mouse genes homologous to RAD52, a yeast gene involved in DNA repair and recombination. Mutat. Res. 315: 295-305 (1994).
36. Emery, H S, Schild, D, Kellogg, D E, Mortimer, R K: Sequence of RAD54, a *Saccharomyces cerevisiae* gene involved in recombination and repair. Gene 104: 103-106 (1991).
37. Kanaar, R, Troelstra, C, Swagemakers, S M, Essers, J, Smit, B, Franssen, J H, Pastink, A, Bezzubova, O Y, Buerstedde, J M, Clever, B, Heyer, W D, Hoeijmakers, J H: Human and mouse homologs of the *Saccharomyces cerevisiae* RAD54 DNA repair gene: evidence for functional conservation. Curr. Biol. 6: 828-838 (1996).
38. Lovett, S T: Sequence of the RAD55 gene of *Saccharomyces cerevisiae*: similarity of RAD55 to prokaryotic RecA and other RecA-like proteins. Gene 142: 103-106 (1994).
39. Dosanjh, M K, Collins, D W, Fan, W, Lennon, G G, Albala, J S, Shen, Z, Schild, D: Isolation and characterization of RAD51C, a new human member of the RAD51 family of related genes. Nucleic Acids Res. 26: 1179-1184 (1998).
40. Kans, J A, Mortimer, R K: Nucleotide sequence of the RAD57 gene of *Saccharomyces cerevisiae*. Gene 105: 139-140 (1991).
41. Bai, Y, Symington, L S: A Rad52 homolog is required for RAD51-independent mitotic recombination in *Saccharomyces cerevisiae*. Genes Dev. 10: 2025-2037 (1996).
42. Benson, F E, Baumann, P, West, S C: Synergistic actions of Rad51 and Rad52 in recombination and DNA repair. Nature 391: 401-404 (1998).
43. Kleff, S, Kemper, B, Sternglanz, R: Identification and characterization of yeast mutants and the gene for a cruciform cutting endonuclease. EMBO J. 11: 699-704 (1992).
44. Kupfer, C, Kemper, B: Reactions of mitochondrial cruciform cutting endonuclease 1 (CCE1) of yeast *Saccharomyces cerevisiae* with branched DNAs in vitro. Eur. J. Biochem. 238: 77-87 (1996).
45. Trelles-Sticken, E, Loidl, J, Scherthan, H: Bouquet formation in budding yeast: initiation of recombination is not required for meiotic telomere clustering. J. Cell Sci. 112 (Pt 5): 651-658 (1999).
46. Scherthan, H, Weich, S, Schwegler, H, Heyting, C, Harle, M, Cremer, T: Centromere and telomere movements during early meiotic prophase of mouse and man are associated with the onset of chromosome pairing. J. Cell Biol. 134: 1109-1125 (1996).

47. Bass, H W, Marshall, W F, Sedat, J W, Agard, D A, Cande, W Z: Telomeres cluster de novo before the initiation of synapsis: a three-dimensional spatial analysis of telomere positions before and during meiotic prophase. J. Cell Biol. 137: 5-18 (1997).
48. Bishop, D K: RecA homologs Dmc1 and Rad51 interact to form multiple nuclear complexes prior to meiotic chromosome synapsis. Cell 79: 1081-1092 (1994).
49. Arbel, A, Zenvirth, D, Simchen, G: Sister chromatid-based DNA repair is mediated by RAD54, not by DMC1 or TID1. EMBO J. 18: 2648-2658 (1999).
50. Roeder, G S: Chromosome synapsis and genetic recombination: their roles in meiotic chromosome segregation. Trends Genet. 6: 385-389 (1990).
51. Li, Z, Golub, E I, Gupta, R, Radding, C M: Recombination activities of HsDmc1 protein, the meiotic human homolog of RecA protein. Proc. Natl. Acad. Sci. U.S.A 94: 11221-11226 (1997).
52. Sung, P, Robberson, D L: DNA strand exchange mediated by a RAD51-ssDNA nucleoprotein filament with polarity opposite to that of RecA. Cell 82: 453-461 (1995).
53. Dresser, M E, Ewing, D J, Conrad, M N, Dominguez, A M, Barstead, R, Jiang, H, Kodadek, T: DMC1 functions in a *Saccharomyces cerevisiae* meiotic pathway that is largely independent of the RAD51 pathway. Genetics 147: 533-544 (1997).
54. Couteau, F, Belzile, F, Horlow, C, Grandjean, O, Vezon, D, Doutriaux, M P: Random chromosome segregation without meiotic arrest in both male and female meiocytes of a dmc1 mutant of *Arabidopsis*. Plant Cell 11: 1623-1634 (1999).
55. Pittman, D L, Cobb, J, Schimenti, K J, Wilson, L A, Cooper, D M, Brignull, E, Handel, M A, Schimenti, J C: Meiotic prophase arrest with failure of chromosome synapsis in mice deficient for Dmc1, a germline-specific RecA homolog. Mol. Cell 1: 697-705 (1998).
56. Johnson, R D, Symington, L S: Functional differences and interactions among the putative RecA homologs Rad51, Rad55, and Rad57. Mol. Cell Biol. 15: 4843-4850 (1995).
57. Basile, G, Aker, M, Mortimer, R K: Nucleotide sequence and transcriptional regulation of the yeast recombinational repair gene RAD51. Mol. Cell Biol. 12: 3235-3246 (1992).
58. Ogawa, T, Yu, X, Shinohara, A, Egelman, E H: Similarity of the yeast RAD51 filament to the bacterial RecA filament. Science 259: 1896-1899 (1993).
59. Sugawara, N, Ivanov, E L, Fishman-Lobell, J, Ray, B L, Wu, X, Haber, J E: DNA structure-dependent requirements for yeast RAD genes in gene conversion. Nature 373: 84-86 (1995).
60. Rockmill, B, Sym, M, Scherthan, H, Roeder, G S: Roles for two RecA homologs in promoting meiotic chromosome synapsis. Genes Dev. 9: 2684-2695 (1995).
61. Clever, B, Interthal, H, Schmuckli-Maurer, J, King, J, Sigrist, M, Heyer, W D: Recombinational repair in yeast: functional interactions between Rad51 and Rad54 proteins. EMBO J. 16: 2535-2544 (1997).
62. Jiang, H, Xie, Y, Houston, P, Stemke-Hale, K, Mortensen, U H, Rothstein, R, Kodadek, T: Direct association between the yeast Rad51 and Rad54 recombination proteins. J. Biol. Chem. 271: 33181-33186 (1996).
63. Shcherbakova, O G, Lanzov, V A, Ogawa, H, Filatov, M V: Overexpression of bacterial RecA protein stimulates homologous recombination in somatic mammalian cells. Mutat. Res. 459: 65-71 (2000).
64. Milne, gene targeting, Weaver, D T: Dominant negative alleles of RAD52 reveal a DNA repair/recombination complex including Rad51 and Rad52. Genes Dev. 7: 1755-1765 (1993).
65. Muris, D F, Bezzubova, O, Buerstedde, J M, Vreeken, K, Balajee, A S, Osgood, C J, Troelstra, C, Hoeijmakers, J H, Ostermann, K, Schmidt, H: Cloning of human and mouse genes homologous to RAD52, a yeast gene involved in DNA repair and recombination. Mutat. Res. 315: 295-305 (1994).
66. Petukhova, G, Stratton, S, Sung, P: Catalysis of homologous DNA pairing by yeast Rad51 and Rad54 proteins. Nature 393: 91-94 (1998).
67. Sugiyama, T, Zaitseva, E M, Kowalczykowski, S C: A single-stranded DNA-binding protein is needed for efficient presynaptic complex formation by the *Saccharomyces cerevisiae* Rad51 protein. J. Biol. Chem. 272: 7940-7945 (1997).
68. Golub, E I, Gupta, R C, Haaf, T, Wold, M S, Radding, C M: Interaction of human rad51 recombination protein with single-stranded DNA binding protein, RPA. Nucleic Acids Res. 26: 5388-5393 (1998).
69. Gasior, S L, Wong, A K, Kora, Y, Shinohara, A, Bishop, D K: Rad52 associates with RPA and functions with rad55 and rad57 to assemble meiotic recombination complexes. Genes Dev. 12: 2208-2221 (1998).
70. Baumann, P, West, S C: Heteroduplex formation by human Rad51 protein: effects of DNA end-structure, hRP-A and hRad52. J. Mol. Biol. 291: 363-374 (1999).
71. Mazin, A V, Zaitseva, E, Sung, P, Kowalczykowski, S C: Tailed duplex DNA is the preferred substrate for Rad51 protein-mediated homologous pairing. EMBO J. 19: 1148-1156 (2000).
72. Kleckner, N: Meiosis: how could it work? Proc. Natl. Acad. Sci. U.S.A 93: 8167-8174 (1996).
73. Shalev, G, Sitrit, Y, Avivi-Ragolski, N, Lichtenstein, C, Levy, A A: Stimulation of homologous recombination in plants by expression of the bacterial resolvase ruvC. Proc. Natl. Acad. Sci. U.S.A 96: 7398-7402 (1999).
74. Philipova, D, Mullen, J R, Maniar, H S, Lu, J, Gu, C, Brill, S J: A hierarchy of SSB protomers in replication protein A. Genes Dev. 10: 2222-2233 (1996).
75. Alani, E, Thresher, R, Griffith, J D, Kolodner, R D: Characterization of DNA-binding and strand-exchange stimulation properties of y-RPA, a yeast single-strand-DNA-binding protein. J. Mol. Biol. 227: 54-71 (1992).
76. Meyer, R R, Laine, P S: The single-stranded DNA-binding protein of *Escherichia coli*. Microbiol. Rev. 54: 342-380 (1990).
77. Citovsky, V, Wong, M L, Zambryski, P: Cooperative interaction of *Agrobacterium VirE2* protein with single-stranded DNA: implications for the T-DNA transfer process. Proc. Natl. Acad. Sci. U.S.A 86: 1193-1197 (1989).
78. Gutierrez, C, Martin, G, Sogo, J M, Salas, M: Mechanism of stimulation of DNA replication by bacteriophage phi 29 single-stranded DNA-binding protein p5. J. Biol. Chem. 266: 2104-2111 (1991).
79. Williams, K R, LoPresti, M B, Setoguchi, M: Primary structure of the bacteriophage T4 DNA helix-destabilizing protein. J. Biol. Chem. 256: 1754-1762 (1981).
80. Monaghan, A, Webster, A, Hay, R T: Adenovirus DNA binding protein: helix destabilising properties. Nucleic Acids Res. 22: 742-748 (1994).

81. Citovsky, V, Knorr, D, Schuster, G, Zambryski, P: The P30 movement protein of tobacco mosaic virus is a single-strand nucleic acid binding protein. Cell 60: 637-647 (1990).
82. Reiss, B, Schubert, I, Kopchen, K, Wendeler, E, Schell, J, Puchta, H: RecA stimulates sister chromatid exchange and the fidelity of double-strand break repair, but not gene targeting, in plants transformed by *Agrobacterium*. Proc. Natl. Acad. Sci. U.S.A 97: 3358-3363 (2000).
83. Shao, R G, Cao, C X, Zhang, H, Kohn, K W, Wold, M S, Pommier, Y: Replication-mediated DNA damage by camptothecin induces phosphorylation of RPA by DNA-dependent protein kinase and dissociates RPA:DNA-PK complexes. EMBO J. 18: 1397-1406 (1999).
84. Biswas, E E, Zhu, F X, Biswas, S B: Stimulation of RTH1 nuclease of the yeast *Saccharomyces cerevisiae* by replication protein A. Biochemistry 36: 5955-5962 (1997).
85. Yanez, R J, Porter, A C: Gene targeting is enhanced in human cells overexpressing hRAD51. Gene Ther. 6: 1282-1290 (1999).
86. Rubin, B P, Ferguson, D O, Holloman, W K: Structure of REC2, a recombinational repair gene of *Ustilago maydis*, and its function in homologous recombination between plasmid and chromosomal sequences. Mol. Cell Biol. 14: 6287-6296 (1994).
87. Asleson, E N, Okagaki, R J, Livingston, D M: A core activity associated with the N terminus of the yeast RAD52 protein is revealed by RAD51 overexpression suppression of C-terminal rad52 truncation alleles. Genetics 153: 681-692 (1999).
88. Reiss, B, Klemm, M, Kosak, H, Schell, J: RecA protein stimulates homologous recombination in plants. Proc. Natl. Acad. Sci. U.S.A 93: 3094-3098 (1996).
89. Schild, D: Suppression of a new allele of the yeast RAD52 gene by overexpression of RAD51, mutations in srs2 and ccr4, or mating-type heterozygosity. Genetics 140: 115-127 (1995).
90. Arnaudeau, C, Helleday, T, Jenssen, D: The RAD51 protein supports homologous recombination by an exchange mechanism in mammalian cells. J. Mol. Biol. 289: 1231-1238 (1999).
91. Vispe, S, Cazaux, C, Lesca, C, Defais, M: Overexpression of Rad51 protein stimulates homologous recombination and increases resistance of mammalian cells to ionizing radiation. Nucleic Acids Res. 26: 2859-2864 (1998).
92. Havre, P A, Rice, M C, Noe, M, Kmiec, E B: The human REC2/RAD51B gene acts as a DNA damage sensor by inducing G1 delay and hypersensitivity to ultraviolet irradiation. Cancer Res. 58: 4733-4739 (1998).
93. Ajimura, M, Leem, S H, Ogawa, H: Identification of new genes required for meiotic recombination in *Saccharomyces cerevisiae*. Genetics 133: 51-66 (1993).
94. Takanami, T, Sato, S, Ishihara, T, Katsura, I, Takahashi, H, Higashitani, A: Characterization of a *Caenorhabditis elegans* recA-like gene Ce-rdh-1 involved in meiotic recombination. DNA Res. 5: 373-377 (1998).
95. Tsuzuki, T, Fujii, Y, Sakumi, K, Tominaga, Y, Nakao, K, Sekiguchi, M, Matsushiro, A, Yoshimura, Y, MoritaT: Targeted disruption of the Rad51 gene leads to lethality in embryonic mice. Proc. Natl. Acad. Sci. U.S.A 93: 6236-6240 (1996).
96. Chanet, R, Heude, M, Adjiri, A, Maloisel, L, Fabre, F: Semidominant mutations in the yeast Rad51 protein and their relationships with the Srs2 helicase. Mol. Cell Biol. 16: 4782-4789 (1996).
97. Sonoda, E, Sasaki, M S, Buerstedde, J M, Bezzubova, O, Shinohara, A, Ogawa, H, Takata, M, Yamaguchi-Iwai, Y, Takeda, S: Rad51-deficient vertebrate cells accumulate chromosomal breaks prior to cell death. EMBO J. 17: 598-608 (1998).
98. Primrose, S B: Principles of Genome Analysis. Blackwell Science Ltd., Oxford (1995).
99. Kumar, L S: DNA markers in plant improvement: An overview. Biotechnol. Adv. 17: 143-182 (1999).
100. Paterson, A H, Tanksley, S D, Sorrells, M E: DNA markers in plant improvement. Advances in Agronomy 46: 39-90 (1997).
101. Rothstein, R: Targeting, disruption, replacement, and allele rescue: integrative DNA transformation in yeast. Methods Enzymol. 194: 281-301 (1991).
102. Offringa, R, De Groot, M J, Haagsman, H J, Does, M P, van den Elzen, P J, Hooykaas, P J: Extrachromosomal homologous recombination and gene targeting in plant cells after *Agrobacterium* mediated transformation. EMBO J. 9: 3077-3084 (1990).
103. Miao, Z H, Lam, E: Targeted disruption of the TGA3 locus in *Arabidopsis thaliana*. Plant J. 7: 359-365 (1995).
104. Zhu, T, Mettenburg, K, Peterson, D J, Tagliani, L, Baszczynski, C L: Engineering herbicide-resistant maize using chimeric RNA/DNA oligonucleotides. Nat. Biotechnol. 18: 555-558 (2000).
105. Broverman, S, MacMorris, M, Blumenthal, T: Alteration of *Caenorhabditis elegans* gene expression by targeted transformation. Proc. Natl. Acad. Sci. U.S.A 90: 4359-4363 (1993).
106. Rong, Y S, Golic, K G: Gene targeting by homologous recombination in drosophila. Science 288: 2013-2018 (2000).
107. Thompson, S, Clarke, A R, Pow, A M, Hooper, M L, Melton, D W: Germ line transmission and expression of a corrected HPRT gene produced by gene targeting in embryonic stem cells. Cell 56: 313-321 (1989).
108. Passy, S I, Yu, X, Li, Z, Radding, C M, Masson, J Y, West, S C, Egelman, E H: Human Dmc1 protein binds DNA as an octameric ring. Proc. Natl. Acad. Sci. U.S.A 96: 10684-10688 (1999).
109. Baumann, P, Benson, F E, Hajibagheri, N, West, S C: Purification of human Rad51 protein by selective spermidine precipitation. Mutat. Res. 384: 65-72 (1997).
110. Yu, X, Egelman, E H: The RecA hexamer is a structural homologue of ring helicases. Nat. Struct. Biol. 4: 101-104 (1997).
111. Tsubouchi, H, Ogawa, H: A novel mre11 mutation impairs processing of double-strand breaks of DNA during both mitosis and meiosis. Mol. Cell Biol. 18: 260-268 (1998).
112. Furuse, M, Nagase, Y, Tsubouchi, H, Murakami-Murofushi, K, Shibata, T, Ohta, K: Distinct roles of two separable in vitro activities of yeast Mre11 in mitotic and meiotic recombination. EMBO J. 17: 6412-6425 (1998).
113. Chedin, F, Seitz, E M, Kowalczykowski, S C: Novel homologs of replication protein A in archaea: implications for the evolution of ssDNA-binding proteins. Trends Biochem. Sci. 23: 273-277 (1998).
114. Kalderon, D, Roberts, B L, Richardson, W D, Smith, A E: A short amino acid sequence able to specify nuclear location. Cell 39: 499-509 (1984).

115. Gupta, R C, Bazemore, L R, Golub, E I, Radding, C M: Activities of human recombination protein Rad51. Proc. Natl. Acad. Sci. U.S.A 94: 463-468 (1997).
116. Zaitseva, E M, Zaitsev, E N, Kowalczykowski, S C: The DNA binding properties of *Saccharomyces cerevisiae* Rad51 protein. J. Biol. Chem. 274: 2907-2915 (1999).
117. Sung, P, Stratton, S A: Yeast Rad51 recombinase mediates polar DNA strand exchange in the absence of ATP hydrolysis. J. Biol. Chem. 271: 27983-27986 (1996).
118. Walker, J E, Saraste, M, Runswick, M J, Gay, N J: Distantly related sequences in the alpha- and beta-subunits of ATP synthase, myosin, kinases and other ATP-requiring enzymes and a common nucleotide binding fold. EMBO J. 1: 945-951 (1982).
119. Story, R M, Weber, I T, Steitz, T A: The structure of the *E. coli* recA protein monomer and polymer. Nature 355: 318-325 (1992).
120. Story, R M, Steitz, T A: Structure of the recA protein-ADP complex. Nature 355: 374-376 (1992).
121. Bergerat, A, de Massy, B, Gadelle, D, Varoutas, P C, Nicolas, A, Forterre, P: An atypical topoisomerase II from Archaea with implications for meiotic recombination. Nature 386: 414-417 (1997).
122. Bressan, D A, Olivares, H A, Nelms, B E, Petrini, J H: Alteration of N-terminal phosphoesterase signature motifs inactivates *Saccharomyces cerevisiae* Mre11. Genetics 150: 591-600 (1998).
123. Current Protocols in Molecular Biology. Ausubel, F M, Brent, R, Kingston, R E, Moore, D D, Seidman, J G, Smith, J A, Struhl, K eds. 1987. John Wiley and Sons, Inc. Ref Type: Serial (Book, Monograph)
124. Chamankhah, M, Wei, Y F, Xiao, W: Isolation of hMRE11B: failure to complement yeast mre11 defects due to species-specific protein interactions. Gene 225: 107-116 (1998).
125. Altschul, S F, Gish, W, Miller, W, Myers, E W, Lipman, D J: Basic local alignment search tool. J. Mol. Biol. 215: 403-410 (1990).
126. Junghans, H, Metzlaff, M: A simple and rapid method for the preparation of total plant DNA. Biotechniques 8: 176 (1990).
127. Hebsgaard, S M, Korning, P G, Tolstrup, N, Engelbrecht, J, Rouze, P, Brunak, S: Splice site prediction in *Arabidopsis thaliana* pre-mRNA by combining local and global sequence information. Nucleic Acids Res. 24: 3439-3452 (1996).
128. Tishkoff, D X, Johnson, A W, Kolodner, R D: Molecular and genetic analysis of the gene encoding the *Saccharomyces cerevisiae* strand exchange protein Sep1. Mol. Cell Biol. 11: 2593-2608 (1991).
129. Link, A J, Olson, M V: Physical map of the *Saccharomyces cerevisiae* genome at 110-kilobase resolution. Genetics 127: 681-698 (1991).
130. Cupples, C G, Miller, J H: A set of lacZ mutations in *Escherichia coli* that allow rapid detection of each of the six base substitutions. Proc. Natl. Acad. Sci. U.S.A 86: 5345-5349 (1989).
131. Schneider, J C, Guarente, L: Vectors for expression of cloned genes in yeast: regulation, overproduction, and underproduction. Methods Enzymol. 194: 373-388 (1991).
132. Gari, E, Piedrafita, L, Aldea, M, Herrero, E: A set of vectors with a tetracycline-regulatable promoter system for modulated gene expression in *Saccharomyces cerevisiae*. Yeast 13: 837-848 (1997).
133. Gietz, R D, Schiestl, R H, Willems, A R, Woods, R A: Studies on the transformation of intact yeast cells by the LiAc/S S-DNA/PEG procedure. Yeast 11: 355-360 (1995).
134. Adams, A, Gottschling, D E, Kaiser, C A, Stearns, T: Mehods in Yeast Genetics. Cold Spring Harbor Laboratory Press, (1997).
135. Dean, R B, Dixon, W: Simplified statistics for small numbers of observations. Anal. Chem. 23: 636-638 (1951).
136. Devore, J L: Probability and Statistics. Duxbury Press, (1995).
137. Chu, S, DeRisi, J, Eisen, M, Mulholland, J, Botstein, D, Brown, P O, Herskowitz, I: The transcriptional program of sporulation in budding yeast. Science 282: 699-705 (1998).
138. Klimyuk, V I, Jones, J D: AtDMC1, the *Arabidopsis* homologue of the yeast DMC1 gene: characterization, transposon-induced allelic variation and meiosis-associated expression. Plant J. 11: 1-14 (1997).
139. Guyer, D, Tuttle, A, Rouse, S, Volrath, S, Johnson, M, Potter, S, Gorlach, J, Goff, S, Crossland, L, Ward, E: Activation of latent transgenes in *Arabidopsis* using a hybrid transcription factor. Genetics 149: 633-639 (1998).
140. Moore, I, Galweiler, L, Grosskopf, D, Schell, J, Palme, K: A transcription activation system for regulated gene expression in transgenic plants. Proc. Natl. Acad. Sci. U.S.A 95: 376-381 (1998).
141. Labow, M A, Baim, S B, Shenk, T, Levine, A J: Conversion of the lac repressor into an allosterically regulated transcriptional activator for mammalian cells. Mol. Cell Biol. 10: 3343-3356 (1990).
142. Ainley, W M, Key, J L: Development of a heat shock inducible expression cassette for plants: characterization of parameters for its use in transient expression assays. Plant Mol. Biol. 14: 949-967 (1990).
143. Martinez, A, Sparks, C, Hart, C A, Thompson, J, Jepson, I: Ecdysone agonist inducible transcription in transgenic tobacco plants. Plant J. 19: 97-106 (1999).
144. Bohner, S, Lenk, I, Rieping, M, Herold, M, Gatz, C: Technical advance: transcriptional activator TGV mediates dexamethasone-inducible and tetracycline-inactivatable gene expression. Plant J. 19: 87-95 (1999).
145. Gatz, C, Kaiser, A, Wendenburg, R: Regulation of a modified CaMV 35S promoter by the Tn10-encoded Tet repressor in transgenic tobacco. Mol. Gen. Genet. 227: 229-237 (1991).
146. Weinmann, P, Gossen, M, Hillen, W, Bujard, H, Gatz, C: A chimeric transactivator allows tetracycline-responsive gene expression in whole plants. Plant J. 5: 559-569 (1994).
147. Mett, V L, Podivinsky, E, Tennant, A M, Lochhead, L P, Jones, W T, Reynolds, P H: A system for tissue-specific copper-controllable gene expression in transgenic plants: nodule-specific antisense of aspartate aminotransferase-P2. Transgenic Res. 5: 105-113 (1996).
148. Mett, V L, Lochhead, L P, Reynolds, P H: Copper-controllable gene expression system for whole plants. Proc. Natl. Acad. Sci. U.S.A 90: 4567-4571 (1993).
149. Benton, B M, Eng, W K, Dunn, J J, Studier, F W, Sternglanz, R, Fisher, P A: Signal-mediated import of bacteriophage T7 RNA polymerase into the *Saccharomyces cerevisiae* nucleus and specific transcription of target genes. Mol. Cell Biol. 10: 353-360 (1990).
150. Church, G. M., Gilbert, W.:Genomic sequencing. Proc. Natl. Acad. Sci. U.S.A 81: 1991-1995 (1984).

151. Ohta K, Shibata T, Nicolas A.: Changes in chromatin structure at recombination initiation sites during yeast meiosis. EMBO J. 13:5754-63 (1994).
152. Peterson C L.: ATP-dependent chromatin remodeling: going mobile. FEBS Lett. 476:68-72 (2000).
153. Peterson C L, Logie C.: Recruitment of chromatin remodeling machines. J Cell Biochem. 78:179-85 (2000).
154. Sterner D E, Berger S L.: Acetylation of histones and transcription-related factors. Microbiol Mol Biol Rev. 64:435-59 (2000).
155. Cress W D, Seto E.: Histone deacetylases, transcriptional control, and cancer. J Cell Physiol. 184:1-16 (2000).
156. Hollingsworth, N M, Goetsch, L, Byers, B: The HOP1 gene encodes a meiosis-specific component of yeast chromosomes. Cell 61: 73-84 (1990).
157. Rockmill, B, Roeder, G S: A meiosis-specific protein kinase homolog required for chromosome synapsis and recombination. Genes Dev. 5: 2392-2404 (1991).
158. Roeder, G S: Sex and the single cell: meiosis in yeast. Proc Natl Acad Sci USA 92: 10450-10456 (1995).
159. Chen, Q, Pearlman, R E, Moens, P B: Isolation and characterization of a cDNA encoding a synaptonemal complex protein. Biochem Cell Biol 70: 1030-1038 (1992).
160. Schmekel, K, Meuwissen, R L, Dietrich, A J, Vink, A C, van Marle, J, van Veen, H, Heyting, C: Organization of SCP1 protein molecules within synaptonemal complexes of the rat. Exp Cell Res 226: 20-30 (1996).
161. Hyde, H, Davies, A A, Benson, F E, West, S C: Resolution of recombination intermediates by a mammalian activity functionally analogous to *Escherichia coli* RuvC resolvase. J. Biol. Chem. 269: 5202-5209 (1994).
162. Vispe, S, Cazaux, C, Lesca, C, Defais, M: Overexpression of Rad51 protein stimulates homologous recombination and increases resistance of mammalian cells to ionizing radiation. Nucleic Acids Res. 26: 2859-2864 (1998).
163. Xu, Y, Ashley, T, Brainerd, E E, Bronson, R T, Meyn, M S, Baltimore, D: Targeted disruption of ATM leads to growth retardation, chromosomal fragmentation during meiosis, immune defects, and thymic lymphoma. Genes Dev. 10: 2411-2422 (1996).
164. Rockmill, B, Roeder, G S: RED1: a yeast gene required for the segregation of chromosomes during the reductional division of meiosis. Proc Natl Acad Sci USA 85: 6057-6061 (1988).
165. Sym, M, Roeder, G S: Zip1-induced changes in synaptonemal complex structure and polycomplex assembly. J Cell Biol 128: 455-466 (1995).

What is claimed is:

1. A eukaryotic cell, wherein the cell is a yeast cell or a plant cell, the cell comprising a nucleic acid encoding a recombinant protein that is homologous to an endogenous protein of the yeast cell or the plant cell, wherein the recombinant protein is a DMC1 protein or a RAD51 protein, wherein the nucleic acid is operably linked to a promoter, wherein expression of the recombinant protein in the cell during meiosis increases the frequency of homologous non-sister chromatid exchange during meiosis compared to a eukaryotic cell that does not comprise the nucleic acid.

2. A eukaryotic cell, wherein the cell is a yeast cell or a plant cell, the cell comprising a nucleic acid encoding a recombinant protein that has a dominant negative effect on meiotic homologous recombination, wherein the recombinant protein is a heterologous DMC1 protein, a mutant DMC1 protein, a heterologous RAD51 protein, or a mutant RAD51 protein, wherein the nucleic acid is operably linked to a promoter, wherein expression of the recombinant protein in the cell during meiosis decreases the frequency of homologous non-sister chromatid exchange during meiosis compared to a eukaryotic cell that does not comprise the nucleic acid.

3. The eukaryotic cell of claim 2, wherein the mutant DMC1 protein includes an aspartate at a position corresponding to glycine 126 of *Saccharomyces cerevisiae* DMC1.

4. The eukaryotic cell of claim 2, wherein the mutant RAD51 protein includes an aspartate at a position corresponding to glycine 190 of *Saccharomyces cerevisiae* RAD51.

5. A method of increasing meiotic homologous recombination in a yeast or a plant, comprising:
    transforming the yeast cell or the plant cell with a nucleic acid encoding a recombinant protein that is homologous to an endogenous protein of the yeast cell or the plant cell, wherein the recombinant protein is a DMC1 protein or a RAD51 protein, wherein the nucleic acid is operably linked to a promoter, to form a transformed cell capable of expressing the recombinant protein during meiosis; and
    allowing the transformed cell, or a descendant of the transformed cell, to undergo meiosis to produce a viable gamete, wherein expression of the recombinant protein in the cell undergoing meiosis increases the frequency of homologous non-sister chromatid exchange during the meiosis.

6. The method of claim 5, wherein the promoter is inducible or repressible, wherein induction of the promoter increases expression of the nucleic acid, or wherein repression of the promoter inhibits expression of the nucleic acid.

7. The method of claim 5, wherein the gamete is crossed with a second gamete to obtain a progeny cell.

8. The method of claim 5, wherein the promoter is meiosis-specific.

9. A method of decreasing meiotic homologous recombination in a yeast or a plant, comprising:
    transforming the yeast cell or the plant cell with a nucleic acid encoding a recombinant protein that is a heterologous protein or a mutant protein that is homologous to an endogenous protein of the yeast cell or the plant cell, wherein the recombinant protein has a dominant negative effect on meiotic homologous recombination, wherein the recombinant protein is a heterologous DMC1 protein, a mutant DMC1 protein, a heterologous RAD51 protein or a mutant RAD51 protein, wherein the nucleic acid is operably linked to a promoter, to form a transformed cell capable of expressing the recombinant protein during meiosis; and
    allowing the transformed cell, or a descendant of the transformed cell, to undergo meiosis to produce a viable gamete, wherein expression of the recombinant protein in the cell undergoing meiosis decreases the frequency of homologous non-sister chromatid exchange during the meiosis.

10. The method of claim 9, wherein the mutant DMC1 protein includes an aspartate at a position corresponding to glycine 126 of *Saccharomyces cerevisiae* DMC1.

11. The method of claim 9, wherein the mutant RAD51 protein includes an aspartate at a position corresponding to glycine 190 of *Saccharomyces cerevisiae* RAD51.

12. The method of claim 9, wherein the transformed cell is a yeast cell and the heterologous protein is *Arabidopsis thaliana* DMC1 protein.

13. The method of claim 9, wherein the promoter is inducible or repressible, wherein induction of the promoter increases expression of the nucleic acid, or wherein repression of the promoter inhibits expression of the nucleic acid.

14. The method of claim 9, wherein the gamete is crossed with a second gamete to obtain a progeny cell.

15. The method of claim 9, wherein the promoter is meiosis-specific.

* * * * *